(12) United States Patent
Motkuri et al.

(10) Patent No.: US 12,319,594 B2
(45) Date of Patent: *Jun. 3, 2025

(54) COMPOSITION AND METHOD FOR CAPTURE AND DEGRADATION OF PFAS

(71) Applicant: Battelle Memorial Institute, Richland, WA (US)

(72) Inventors: Radha K. Motkuri, Richland, WA (US); Sayandev Chatterjee, Richland, WA (US); Dushyant Barpaga, Richland, WA (US); Bernard P. McGrail, Pasco, WA (US)

(73) Assignee: Battelle Memorial Institute, Richland, WA (US)

( * ) Notice: Subject to any disclaimer, the term of this patent is extended or adjusted under 35 U.S.C. 154(b) by 337 days.

This patent is subject to a terminal disclaimer.

(21) Appl. No.: 17/979,454

(22) Filed: Nov. 2, 2022

(65) Prior Publication Data

US 2023/0089418 A1 Mar. 23, 2023

Related U.S. Application Data

(63) Continuation of application No. 16/869,471, filed on May 7, 2020, now Pat. No. 11,518,689.

(60) Provisional application No. 62/980,681, filed on Feb. 24, 2020, provisional application No. 62/942,637, filed on Dec. 2, 2019, provisional application No. 62/851,854, filed on May 23, 2019.

(51) Int. Cl.
| | |
|---|---|
| C02F 1/28 | (2023.01) |
| A62D 3/115 | (2007.01) |
| A62D 3/38 | (2007.01) |
| A62D 3/40 | (2007.01) |
| B01J 20/22 | (2006.01) |
| B01J 27/188 | (2006.01) |
| B01J 27/19 | (2006.01) |
| B01J 27/195 | (2006.01) |
| B01J 27/198 | (2006.01) |
| B01J 31/24 | (2006.01) |
| B01J 35/39 | (2024.01) |
| C02F 1/30 | (2023.01) |
| C02F 1/32 | (2023.01) |
| C02F 1/58 | (2023.01) |
| C02F 1/72 | (2023.01) |
| G01N 27/07 | (2006.01) |
| G01N 27/22 | (2006.01) |
| G01N 27/48 | (2006.01) |
| G01N 33/18 | (2006.01) |
| A62D 101/22 | (2007.01) |
| C02F 101/36 | (2006.01) |
| C02F 103/06 | (2006.01) |

(52) U.S. Cl.
CPC ............ *C02F 1/288* (2013.01); *A62D 3/115* (2013.01); *A62D 3/38* (2013.01); *A62D 3/40* (2013.01); *B01J 20/226* (2013.01); *B01J 27/188* (2013.01); *B01J 27/19* (2013.01); *B01J 27/195* (2013.01); *B01J 27/198* (2013.01); *B01J 31/24* (2013.01); *B01J 35/39* (2024.01); *C02F 1/283* (2013.01); *C02F 1/30* (2013.01); *C02F 1/32* (2013.01); *C02F 1/583* (2013.01); *C02F 1/725* (2013.01); *G01N 27/07* (2013.01); *G01N 27/226* (2013.01); *G01N 27/48* (2013.01); *G01N 33/1886* (2013.01); *A62D 2101/22* (2013.01); *B01J 2231/005* (2013.01); *B01J 2531/74* (2013.01); *C02F 1/281* (2013.01); *C02F 1/285* (2013.01); *C02F 2101/36* (2013.01); *C02F 2103/06* (2013.01); *C02F 2209/001* (2013.01); *C02F 2209/003* (2013.01); *C02F 2209/40* (2013.01); *C02F 2303/16* (2013.01); *C02F 2305/08* (2013.01); *C02F 2305/10* (2013.01)

(58) Field of Classification Search
CPC .. C02F 1/28; C02F 1/288; C02F 1/283; C02F 1/30; C02F 1/32; C02F 1/583; C02F 1/725; C02F 1/281; C02F 1/285; C02F 2101/36; C02F 2103/06; C02F 2209/001; C02F 2209/003; C02F 2209/40; C02F 2303/16; C02F 2305/08; C02F 2305/10; B01J 35/39; B01J 20/226; B01J 27/188; B01J 27/19; B01J 27/195; B01J 27/198; B01J 31/24; B01J 2231/005; B01J 2531/74; G01N 27/48; G01N 33/1886; A62D 3/115; A62D 3/38
USPC ......................................................... 502/303
See application file for complete search history.

(56) References Cited

U.S. PATENT DOCUMENTS

| | | | |
|---|---|---|---|
| 8,771,938 B2 | 7/2014 | Chang et al. | |
| 11,518,689 B2 * | 12/2022 | Motkuri | ............ G01N 33/1826 |

OTHER PUBLICATIONS

Barpaga et al., "Probing the Sorption of Perfluorooctanesulfonate Using Mesoporous Metal-Organic Frameworks from Aqueous Solutions," *Inorg. Chem.*, May 8, 2019, vol. 58, pp. 8339-8346.

(Continued)

*Primary Examiner* — Edward M Johnson
(74) *Attorney, Agent, or Firm* — Klarquist Sparkman, LLP

(57) ABSTRACT

Materials for binding per- and polyfluoroalkyl substances (PFAS) are disclosed. A fluidic device comprising the materials for detection and quantification of PFAS in a sample is disclosed. The fluidic device may be configured for multiplexed analyses. Also disclosed are methods for sorbing and remediating PFAS in a sample. The sample may be groundwater containing, or suspected of containing, one or more PFAS.

20 Claims, 34 Drawing Sheets

(56) References Cited

OTHER PUBLICATIONS

Cheng et al. "Metal-Organic Framework-Based Microfluidic Impedance Sensor Platform for Ultrasensitive Detection of Perfluorooctanesulfonate," *ACS Appl. Mater. Interfaces*, Feb. 7, 2020, 12:10503-10514 and supplemental information.

Diaz et al., "Ordered covalent organic frameworks, COFs and PAFs. From preparations to Applications," 2015, 68 pages.

Moreton et al., "Liquid-Phase Applications of Metal-Organic Framework Mixed-Matrix Membranes Prepared from Poly(ethylene-co-vinyl acetate)," *ACS Appl. Polym. Mater.* Mar. 20, 2020, abstract only.

Ozdemir et al., "A Novel, Nanostructured, Metal-Organic Frameworks-Based Pretreatment Technology for the Remediation of PFAS in Industrial Wastewater," *TechConnect Briefs* 2019, pp. 213-216.

Sini et al., "Metal-Organic Framework Sorbents for the Removal of Perfluorinated Compounds in an Aqueous Environment," *New Journal of Chemistry*, Sep. 21, 2018, vol. 42, No. 22, pp. 17889-17894.

Zheng et al., "Molecular Insight into Fluorocarbon Adsorption in Pore Expanded Metal-Organic Framework Analogs," *Journal of the American Chemical Society*, Jan. 22, 2020, vol. 142, pp. 3002-3012.

\* cited by examiner

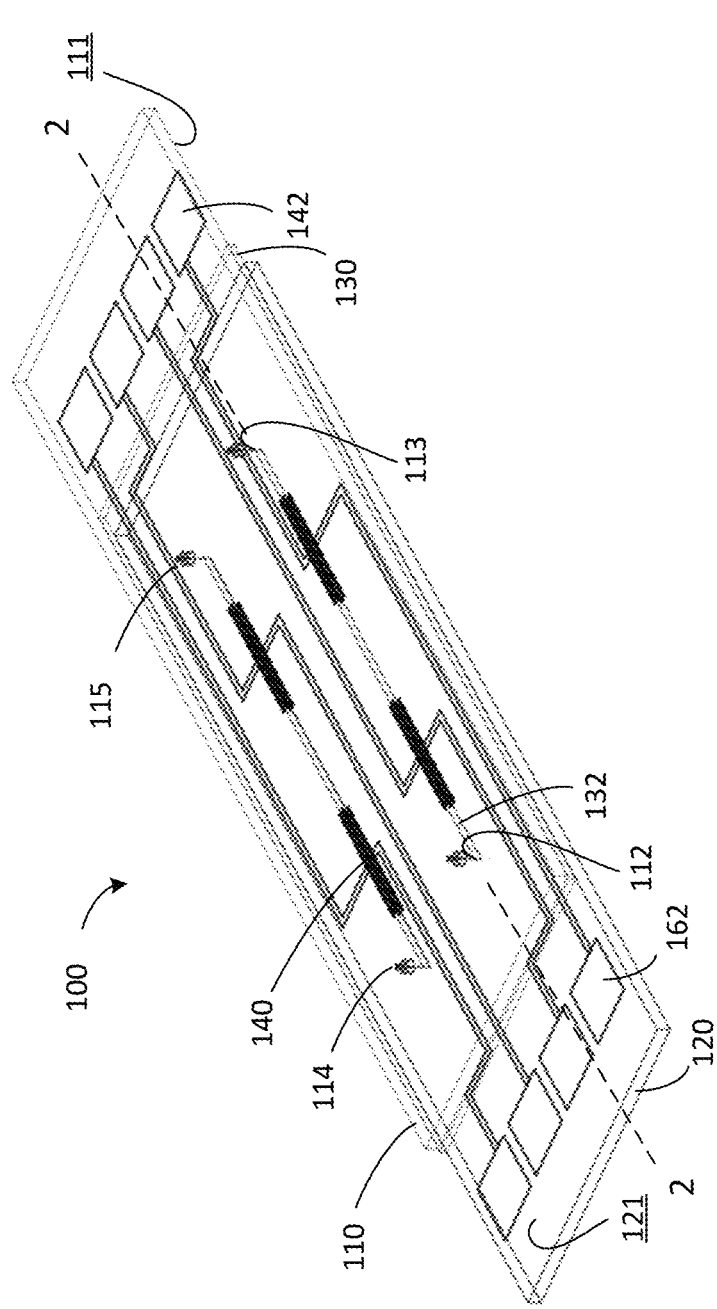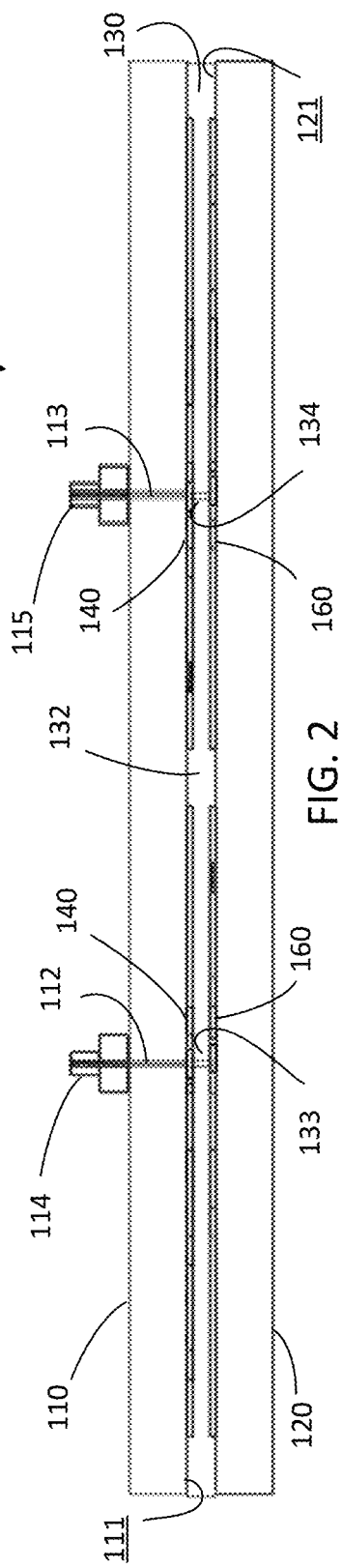
FIG. 1
FIG. 2

FIG. 20A
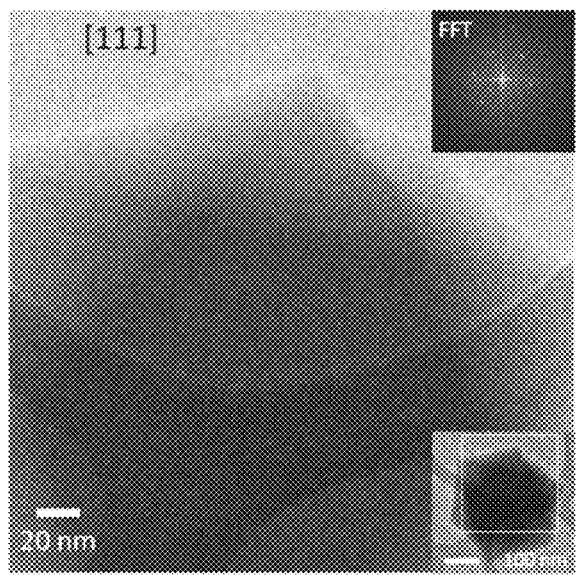
FIG. 20B
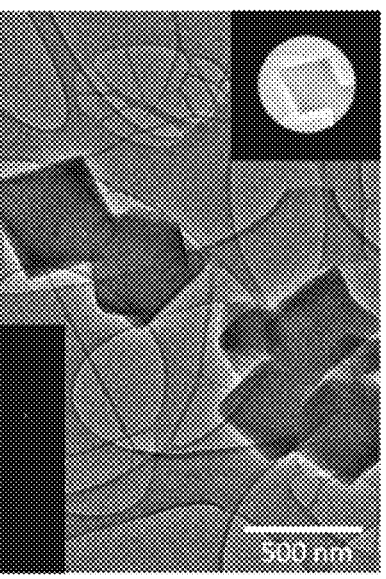
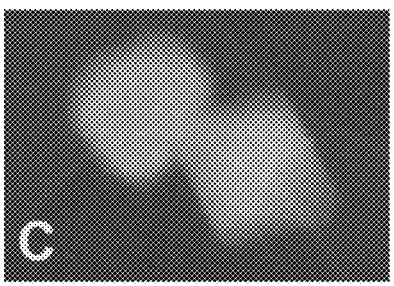
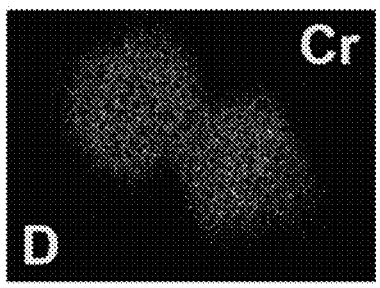
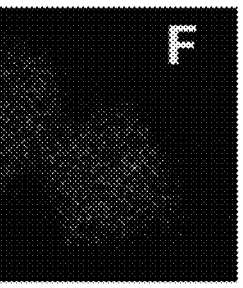
FIG. 20C   FIG. 20D   FIG. 20E
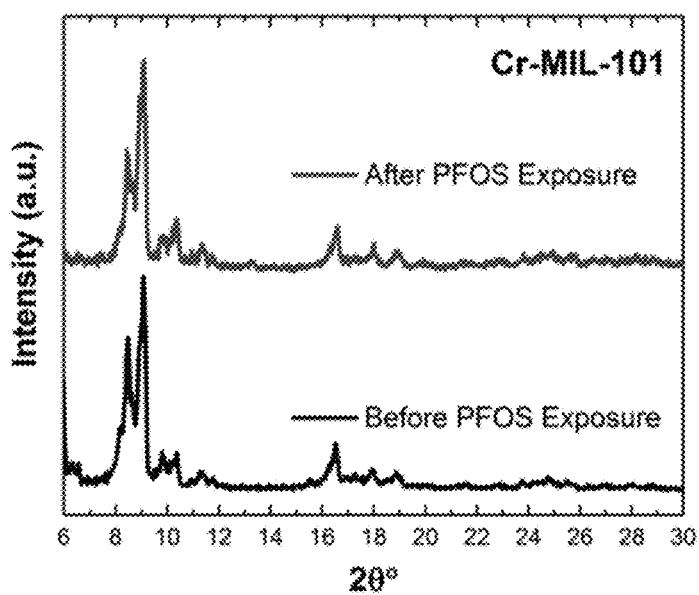
FIG. 21

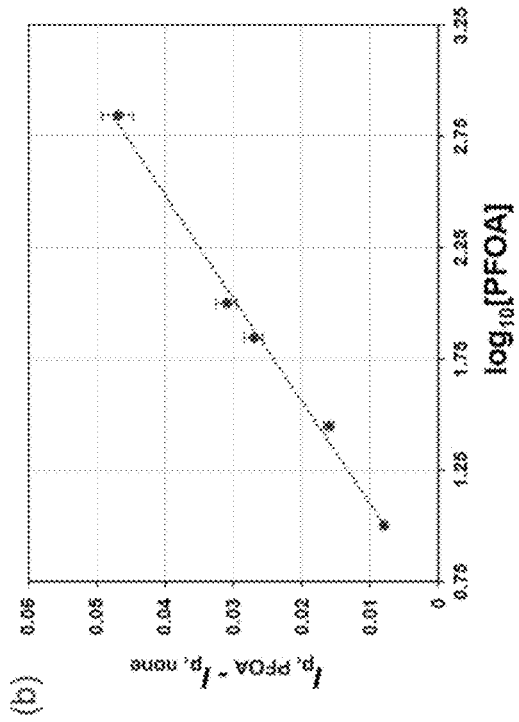
FIG. 59A
FIG. 59B
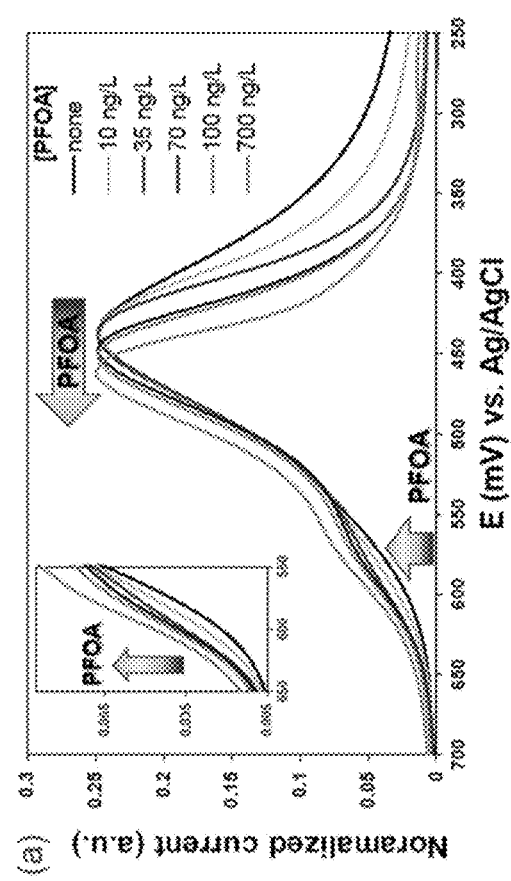
FIG. 60A
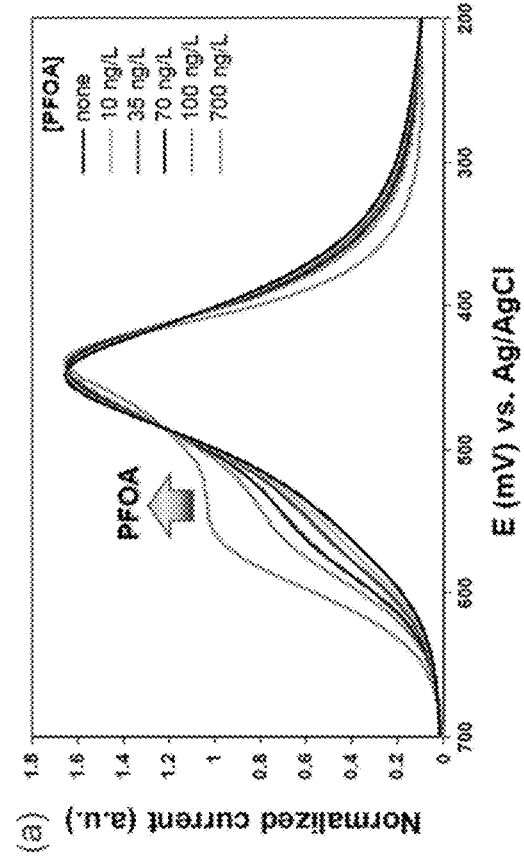
FIG. 60B

COMPOSITION AND METHOD FOR CAPTURE AND DEGRADATION OF PFAS

CROSS REFERENCE TO RELATED APPLICATIONS

This application is a continuation of U.S. application Ser. No. 16/869,471, filed May 7, 2020, now U.S. Pat. No. 11,518,689, issued Dec. 6, 2022, which claims the benefit of the earlier priority dates of U.S. Provisional Application No. 62/980,681, filed Feb. 24, 2020, U.S. Provisional Application No. 62/942,637, filed Dec. 2, 2019, and U.S. Provisional Application No. 62/851,854, filed May 23, 2019, each of which is incorporated by reference herein in its entirety.

ACKNOWLEDGMENT OF GOVERNMENT SUPPORT

This invention was made with Government support under Contract DE-AC05-76RL01830 awarded by the U.S. Department of Energy. The Government has certain rights in the invention.

FIELD

This invention discloses embodiments of materials, a device, and methods for detecting per- and polyfluoroalkyl substances (PFAS). Also disclosed are embodiments of a method for binding and remediating PFAS.

BACKGROUND

PFAS (per- or polyfluoroalkyl substance(s)) is a name used to describe a family of potentially thousands of synthetic chemicals that are extremely persistent in the environment and in our bodies. The term PFAS includes, among others, chemicals commonly known as PFOS, PFOA and GenX. Aqueous film forming foams (AFFF) which are widely used to fight hydrocarbon fuel fires on military sites contain PFAS chemicals. The use of these foams has resulted in raised PFAS concentrations around these sites that are several orders of magnitude higher than the US EPA health advisory level (HAL) for drinking water. Other PFAS sources include the semiconductor, electronics, oil recovery, and photolithography industries, as well as fire extinguishers, firefighting foams, fabric protectors, nonstick products, polishes, paints, cleaning products, and packaged foods. PFAS include about 6500 environmentally stable and biopersistent anthropogenic fluorinated compounds. At least 240 compounds belonging to 57 classes have been detected in AFFF, of which 24 to date have been determined to be toxic by the Environmental Protection Agency. PFAS are highly mobile in the environment and groundwater. PFAS diffusion and speciation depend at least in part on commingled contaminants (mixed plume and multiple influents), hydrophobic partitioning to soil organic matter (shorter chains are more water soluble, while longer chains adsorb and partition to soil more), electrostatic interactions between PFAS molecules and charged soil/mineral surfaces, and pH, among others.

Extensive commercial and industrial PFAS-based applications spanning the past ~60 years have further contributed to their occurrence, while their high aqueous solubility and extreme resistance to degradation have made them ubiquitous in the environment. PFAS can bioaccumulate in the environment and in the body. Recent studies linking human exposure to PFAS to health issues including elevated cholesterol, obesity, immune suppression, endocrine disruption, liver damage, kidney damage, pregnancy-induced hypertension, increased risk of thyroid disease, increased risk of decreased fertility, increased risk of asthma, decreased vaccine response, and cancer, helped dictate setting the federal lifetime HAL for the most commonly studied PFAS, (i.e. perfluorooctanoic acid [PFOA] and perfluorooctanesulfonate [PFOS]) as low as 70 ng/L (either individually or cumulatively).

SUMMARY

Embodiments of compositions and methods to capture PFAS from a sample are disclosed. The captured PFAS may subsequently be degraded.

Some embodiments of a method for removing a PFAS from a sample include (i) combining the sample with a composite sorbent, thereby sorbing the PFAS to the sorbent to form a PFAS-sorbent, the composite sorbent comprising at least two different materials selected from (a) a metal-organic framework (MOF), a covalent organic framework (COF), a covalent organic polymer (COP), zeolites, mesoporous silica, hierarchical porous carbon in combination with (b) at least one of a polymer, a zeolite, a covalent organic framework, mesoporous silica, a hierarchical porous carbon, a photocatalyst, a carbon nanotube, graphite, graphene, graphene oxide, a Prussian blue analog, or a metal oxide; and (ii) separating the PFAS-sorbent from the sample. In certain embodiments, (i) the MOF, if present, does not comprise $[Zr_6O_4(OH)_4]$ and 1,4-benzodicarboxylic acid (UiO-66), and/or (ii) the polymer, if present, is not poly(ethylene-co-vinyl acetate). In some embodiments, combining the sample with the composite sorbent comprises flowing the sample through a bed of a column, the bed comprising the composite sorbent.

In any of the foregoing embodiments, the method may further include heating the PFAS-sorbent to a temperature $T_1$ sufficient to thermally degrade the PFAS. In some embodiments, the temperature $T_1$ is less than a temperature $T_2$ sufficient to thermally degrade the PFAS when not sorbed to the composite sorbent. In certain embodiments, the temperature $T_1$ is within a range of from 50-200° C. In any of the foregoing embodiments, the method may further include heating the PFAS-sorbent in a solution comprising $H_2SO_4$, $NaHSO_5$, $Na_2S_2O_8$, $FeSO_4$, $H_2O_2$, $Na_2S_2O_4$, $NaClO_3$, $NaClO_4$, $Na_2S_2O_5$, HCl, KI, $NaNO_3$, $HNO_3$, Fe(O), Zn, Ni, $Na_2SO_3$, NaClO, $Ca(OH)_2$, $K_2CrO_4$, $Na_2S_2O_3$, $Na_2CO_3$, $KMnO_4$, $K_2FeO_4$, $NaBH_4$, NaOH, KOH, or any combination thereof.

In some embodiments, the composite sorbent comprises a photocatalyst, and the method further includes exposing the PFAS-sorbent to light having a wavelength effective to excite the photocatalyst, thereby degrading the PFAS. Exemplary photocatalysts include, but are not limited to rhenium (II) dimethylphosphinoethane and salts thereof, and polyoxometalates.

Some embodiments of a method for detecting presence of PFAS in a sample include combining a sample with a sorbent comprising a redox-active metal-organic framework (MOF) to sorb PFAS present in the sample to the MOF to form a PFAS-sorbent; measuring a redox signal of the combined sample and MOF using voltammetry; and comparing the redox signal to a redox signal of the MOF in a sample that does not comprise a PFAS, wherein a difference between the redox signals indicates presence of PFAS in the sample. In one embodiment, the method further includes heating the PFAS-sorbent to a temperature $T_1$ sufficient to thermally degrade the PFAS. In an independent embodiment, the method further includes applying an oxidizing potential to the PFAS-sorbent, where the oxidizing potential is effective to oxidatively degrade the PFAS.

The foregoing and other objects, features, and advantages of the invention will become more apparent from the following detailed description, which proceeds with reference to the accompanying figures.

BRIEF DESCRIPTION OF THE DRAWINGS

FIG. 1 is a perspective view of an exemplary fluidic device.

FIG. 2 is a cross-sectional view of the exemplary fluidic device of FIG. 1 taken along line 2-2.

FIGS. 20A-20E are transmission electron micrographs of Cr-MIL-101 before (20A) and after (20B) PFOS exposure. The top right inset of FIG. 20A represents a Fast Fourier transform image while the bottom right inset shows a zoomed-out image of a Cr-MIL-101 particle before PFOS exposure. The top right inset of FIG. 20B shows a magnified image of Cr-MIL-101 particle post PFOS exposure while the bottom left inset shows the electron diffraction map. FIG. 20C is a magnified image of the PFOS exposed particles. FIGS. 20D-20E are overlays of elemental maps showing Cr distribution (20D) and F distribution (20E) on the PFOS-exposed particles.

FIG. 21 shows powder X-ray diffraction spectra of Cr-MIL-101 before and after exposure to PFOS.

FIGS. 59A-59B show linear sweep voltammograms (sweep rate=50 mV/s) of NiFe coated ITO electrode (vs. Ag/AgCl) in presence of 0-700 ng/L of PFOA, inset shows magnification of the 550-650 mV potential region (59A); and a calibration curve of $I_{p,\ PFOA}-I_{p,\ none}$ versus the logarithm of PFOA concentrations (59B). The equation of the line $I_{p,\ PFOA}-I_{p,\ none}=0.0216\ \log_{10}[PFOA]-0.0137$, $R^2=0.9937$.

FIGS. 60A-60B show differential pulse voltammograms of NiFe coated ITO electrode (vs. Ag/AgCl) in presence of 0-700 ng/L of PFOA (60A); and a calibration curve of $I_{p,\ PFOA}-I_{p,\ none}$ versus the logarithm of PFOA concentrations (60B). The equation of the line $I_{p,\ PFOA}-I_{p,\ none}=0.316\ \log_{10}[PFOA]-0.346$, $R^2=0.981$.

DETAILED DESCRIPTION

Figure 3:
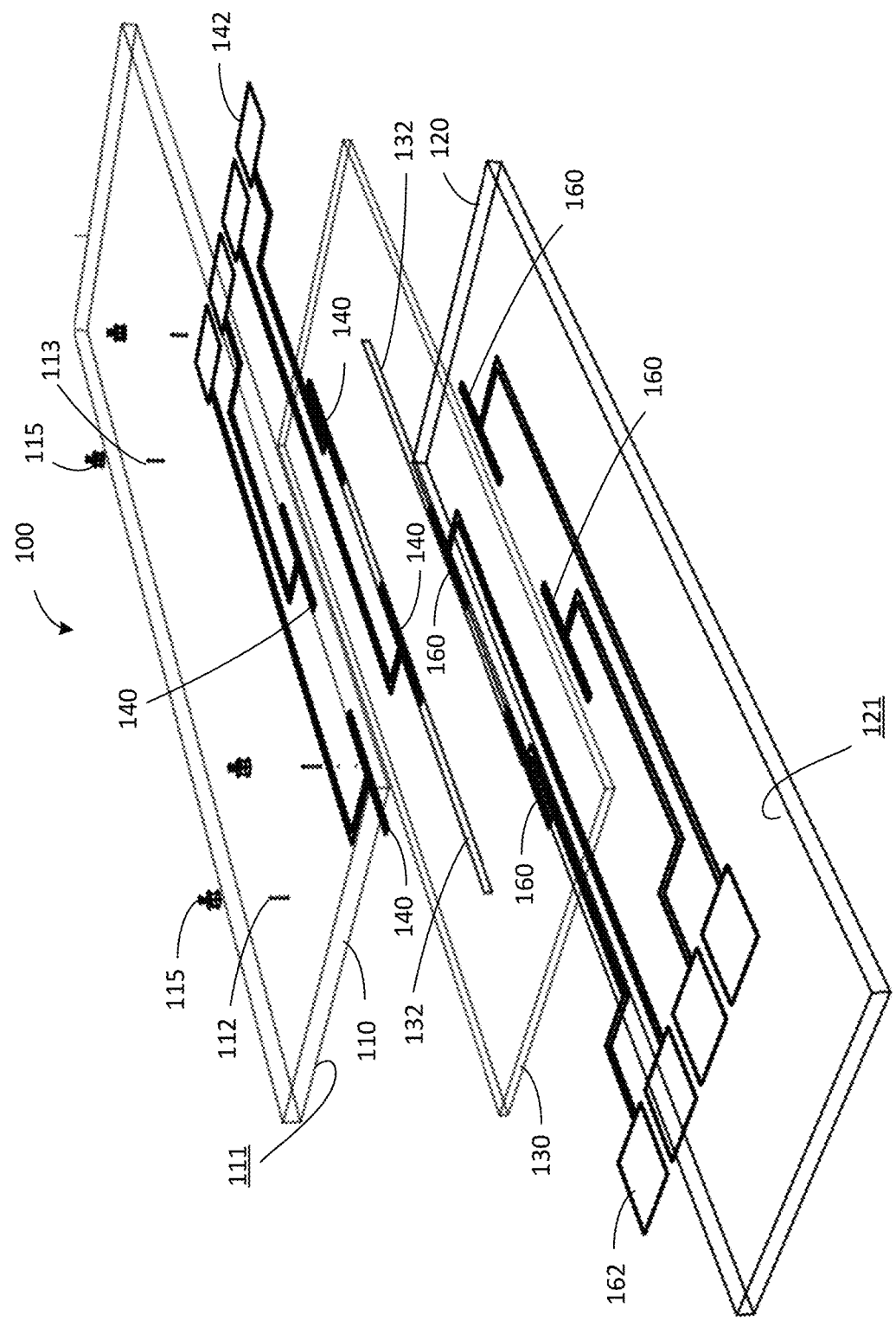
FIG. 3 is an exploded perspective view of the exemplary fluidic device of FIG. 1.

Current PFAS analysis methods are poorly suited for field deployment due in part to requirements such as of derivatization prior to analyses, lengthy sample preparation, cost, and instrument maintenance. Predominant methods include mass spectrometry (MS)-based ex-situ laboratory techniques. Commonly used modes include analytical scale extraction and subsequent analysis by liquid chromatography tandem mass spectrometry (LC-MS/MS) and total oxidizable precursor (TOP). An alternative approach to MS involves the analyses of total fluorine by particle induced gamma ray emission (PIGE) spectroscopy. However, these methods are poorly suited to use in the field.

Additionally, prior probes and sorbents for PFAS capture and detection have exhibited poor uptake, slow kinetics, and/or poor selectivity. Some prior probes have been based on a general electronic affinity for electron rich hydrophobic groups (e.g., perfluoroalkyl or similar species). While prior sensors were able detect PFOS and PFOA in simple matrices (DI water and drinking water), the nonspecific binding limited both selectivity and sensitivity in practical matrices, due to the inability to screen out interferences with similar electronic properties and hydrophobicity. To improve selectivity, prior molecularly imprinted polymer (MIP)-based probes were prepared in the presence of specific guest templates followed by the removal of the template molecule, leaving complementary cavities behind. These polymers showed affinity for the template molecule due to steric complementarity. While this by itself could lead to high sensitivity in simple matrices, the absence of any nonspecific electronic interactions prevented it from screening out the smaller congeners or other isostructural organics that could fit within the cavity spaces and produced false responses. In addition, the physical MIP coating on the electrode resulted in poor communication between the MIP probe and the electrode, resulting in low signal to noise ratio (SNR) and poor reliability.

For at least these reasons, a portable, field-deployable technique for rapid, reliable and accurate detection and quantification of PFAS is needed for rapid field-screening purposes. Embodiments of the disclosed sorbent materials, devices, and methods solve these problems. Additionally, some embodiments of the disclosed sorbent materials and methods are also useful for PFAS remediation. Table 1 is a representative, non-exhaustive list of PFAS compounds provided by the United States Environmental Protection Agency.

TABLE 1

| | |
|---|---|
| N-Ethyl-N-(2-hydroxyethyl)perfluorooctanesulfonamide | N-Methyl-N-(2-hydroxyethyl)perfluorooctanesulfonamide |
| 8:2 Fluorotelomer alcohol | 10:2 Fluorotelomer alcohol |
| Perfluorodecanoic acid | Perfluorododecanoic acid |
| Perfluorononanoic acid | Perfluorooctanesulfonic acid |
| Lithium perfluorooctanesulfonate | N-Ethylperfluorooctanesulfonamide |
| Potassium perfluorooctanesulfonate | Potassium perfluorobutanesulfonate |
| Potassium perfluorohexanesulfonate | 10:2 Fluorotelomer acrylate |
| Fluorotelomer alcohol | Perfluorobutanesulfonic acid |
| Perfluorohexanoic acid | Ammonium perfluorooctanoate |
| Perfluorooctanoic acid | 6:2 Fluorotelomer acrylate |
| Perfluoroheptanoic acid | Perfluorohexanesulfonic acid |
| Perfluorooctanesulfonamide | Perfluorodecanesulfonic acid |
| 6:2 Fluorotelomer sulfonamide betaine | Trifluoroacetic acid |
| 6:2 Fluorotelomer alcohol | Perfluoro(4-methyl-3,6-dioxaoct-7-ene)sulfonyl fluoride |
| 6:2 Fluorotelomer methacrylate | Perfluoro-3-(1H-perfluoroethoxy)propane |
| 7:1 Fluorotelomer alcohol | Perfluorobutanoic acid |
| Perfluorotetradecanoic acid | Perfluoropropanoic acid |
| Perfluoroundecanoic acid | Perfluoroheptanesulfonic acid |
| Sodium perfluorohexanoate | 8:2 Fluorotelomer methacrylate |
| 4:2 Fluorotelomer alcohol | 10:2 Fluorotelomer methacrylate |
| Perfluoropentanesulfonic acid | 2-(N-Ethylperfluorooctanesulfonamido)acetic acid |
| Perfluorooctane sulfonamido amine | Perfluorooctadecanoic acid |
| 6:2 Fluorotelomer sulfonic acid | 8:2 Fluorotelomer acrylate |
| N-Methylperfluorooctanesulfonamide | Perfluorohexane sulfonamido amine |
| Perfluoroheptane sulfonamido amine | Perfluorohexadecanoic acid |
| Perfluoropentanoic acid | Ammonium perfluorooctanesulfonate |
| Potassium perfluoropentanesulfonate | Potassium perfluoroheptanesulfonate |
| Ammonium perfluorononanesulfonate | Ammonium perfluorodecanesulfonate |
| Ammonium perfluoroheptanesulfonate | Ammonium perfluorohexanesulfonate |
| Ammonium perfluorobutanesulfonate | Perfluorononanesulfonic acid |
| Perfluoropentane sulfonamido amine | Lithium perfluoroheptanesulfonate |
| Perfluorooctanesulfonate | Trifluoroacetate |
| Perfluoro-3-methoxypropanoic acid | 8:2 Fluorotelomer sulfonic acid |
| Perfluoro-4-(perfluoroethyl)cyclohexylsulfonic acid | Perfluoro-(2,5,8-trimethyl-3,6,9-trioxadodecanoic)acid |
| Ammonium perfluoropentanesulfonate | 6:1 Fluorotelomer alcohol |
| Perfluorobutane sulfonamido amine | 8:2 Fluorotelomer phosphate diester |
| Ammonium perfluoro-2-methyl-3-oxahexanoate | 8:1 Fluorotelomer alcohol |
| 9:1 Fluorotelomer alcohol | 11:1 Fluorotelomer alcohol |
| 10:1 Fluorotelomer alcohol | Perfluoro-3,6,9-trioxadecanoic acid |
| Perfluoro-3,6-dioxaheptanoic acid | 5:1 Fluorotelomer alcohol |
| Difluoro(perfluoromethoxy)acetic acid | 2-Perfluorooctyl ethanoic acid |
| Perfluoro(4-methoxybutanoic) acid | 7:2 sFluorotelomer alcohol |
| 6:2 Fluorotelomer phosphate monoester | 6:2 Fluorotelomer phosphate diester |
| Perfluoro-3,6,9-trioxatridecanoic acid | 2-Perfluorohexyl ethanoic acid |
| Perfluoro-3,6-dioxadecanoic acid | Perfluoro-2-(perfluoromethoxy)propanoic acid |
| 3-Perfluoroheptylpropanoic acid | 2-(N-Methylperfluorooctanesulfonamido)-acetic acid |
| Sodium perfluorooctanesulfonate | Perfluoro-4-isopropoxybutanoic acid |
| | Perfluorooctanesulfonamido amine oxide |
| Perfluoro-3,5,7,9,11-pentaoxadodecanoic acid | 2H-Perfluoro-2-decenoic acid |
| Perfluorooctanesulfonamido ammonium | 8-Fluorosulfonylperfluoro(2,5-dimethyl-3,6-dioxaoctanoyl) fluoride |
| Perfluoroethanesulfonic acid | Perfluoropropanesulfonic acid |
| Perfluorohexanesulfonate | Perfluorodecanesulfonate |
| 6:2/8:2 Fluorotelomer phosphate diester | 8:2 Fluorotelomer sulfonate |
| Ammonium 4,8-dioxa-3H-perfluorononanoate | 8:2 Fluorotelomer phosphate monoester |
| Perfluoro-3,5,7,9-butaoxadecanoic acid | Perfluorononanesulfonate |
| Difluoro(perfluoropropoxy)acetic acid | Perfluorobutanesulfonate |
| Perfluorotridecanoic acid | 6:2 Fluorotelomer sulfonate |
| Ammonium perfluorodecanoate | 2H,2H,3H,3H-Perfluorooctanoic acid |
| Sodium perfluorooctanoate | Potassium perfluorooctanoate |
| Sodium perfluorodecanoate | Silver perfluorooctanoate |
| Sodium perfluoropentanoate | Ammonium 2-(N-ethylperfluorooctanesulfonamido)acetate |

TABLE 1-continued

| | |
|---|---|
| Sodium perfluorobutanoate | Ammonium perfluoro-9-(methyl)decanoate |
| Silver perfluorobutanoate | Sodium 2-(N-ethylperfluorooctanesulfonamido)acetate |
| Ammonium perfluoroheptanoate | Perfluoro-2-methyl-3-oxahexanoic acid |
| Ammonium perfluorohexanoate | 8:2 Fuorotelomer sulfonamide betaine |
| Lithium perfluorohexanesulfonate | Ammonium perfluoropentanoate |
| 4,8-Dioxa-3H-perfluorononanoic acid | Perfluorosulfonic acid, PTFE copolymer |
| Perfluorooctanesulfonamido betaine | 4:2 Fluorotelomer sulfonic acid |
| 2-Perfluorodecyl ethanoic acid | 2H-Perfluoro-2-octenoic acid |
| Perfluorooctanesulfonamido ethanol | 6:2 Fluorotelomer thioether amido sulfonic acid |
| Ammonium perfluorononanoate | 4:2 Fluorotelomer thioether amido betaine |
| Sodium perfluoroheptanoate | 4:2 Fluorotelomer sulfonate |
| 10:2 Fluorotelomer sulfonamide betaine | Perfluoro-4-(perfluoroethyl)cyclohexylsulfonate |
| Potassium 9-chlorohexadecafluoro-3-oxanonane-1-sulfonate | 6:2 Fluorotelomer thioether amido sulfonate |
| 8:2 Fluorotelomer thioether amido sulfonic acid | 8:2 Fluorotelomer thioether amido sulfonate |
| Perfluoro-3,5,7-trioxaoctanoic acid | Perfluoro-3,5-dioxahexanoic acid |
| Perfluoro-3,6-dioxa-4-methyl-7-octene-1-sulfonic acid | Perfluoro-2-(perfluoropropoxy)-2-(perfluoromethyl)propanoic acid |
| Perfluoro-2-(perfluorobutoxy)-2-(perfluoromethyl)propanoic acid | Perfluoro-3-ethoxypropanoic acid |
| Perfluoro-2,5-dimethyl-3,6-dioxanonanoic acid | Sodium perfluorodecanesulfonate |
| Potassium 11-chloroeicosafluoro-3-oxaundecane-1-sulfonate | Sodium 4,8-dioxa-3H-perfluorononanoate |
| 5:3 Fluorotelomer betaine | Perfluoro(2,5,8,10-tetramethyl-3,6,9-trioxaundecanoic) acid |
| Perfluoro-2-{[perfluoro-3-(perfluoroethoxy)-2-propanyl]oxy}ethanesulfonic acid | Perfluoro(2,5,8,11,14-pentamethyl-3,6,9,12,15-pentaoxaoctadecanoic) acid |
| Perfluoro-2-[(perfluoropentyl)oxy]propanoic acid | Perfluoroundecanoate |
| Sodium perfluorohexanesulfonate | Perfluoropropanoate |
| Perfluorobutanoate | Perfluorodecanoate |
| Perfluoroheptanoate | Perfluorohexanoate |
| Perfluorooctanoate ion(1−) | Perfluoropentanoate |
| Perfluorotridecanoate | 2-(N-Methylperfluorooctanesulfonamido)acetate |
| Perfluoroheptanesulfonate | 5:1:2 Fluorotelomer betaine |
| Perfluoropentanesulfonate | Perfluorotetradecanoate |
| Perfluorododecanoate | 2-(N-Ethyl-perfluorooctanesulfonamido)acetate |
| Perfluorononanoate | 7:1:2 Fluorotelomer betaine |
| 7:3 Fluorotelomer betaine | 9:1:2 Fluorotelomer betaine |
| 8:2 Fluorotelomer sulfonamido N,N-dimethyl amine ion | 6:2 Fluorotelomer sulfonamido N,N-dimethyl amine |
| 4:2 Fluorotelomer thioether amido sulfonate | 4:2 Fluorotelomer thioether amido sulfonic acid |
| Perfluorobutane sulfonamide amino carboxylates | Perfluoroheptane sulfonamide amino carboxylates |
| Perfluorooctane sulfonamide amino carboxylates | Perfluoropentane sulfonamide amino carboxylates |
| Perfluorooctaneamido ammonium | |
| 12:2 Fluorotelomer sulfonamido betaine | Perfluorohexane sulfonamide amino carboxylates |
| 6:2 Fluorotelomer thioether hydroxyammonium | Perfluorooctaneamido amine oxide |
| 9:3 Fluorotelomer betaine | |

I. Definitions and Abbreviations

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

The disclosure of numerical ranges should be understood as referring to each discrete point within the range, inclusive of endpoints, unless otherwise noted. Unless otherwise indicated, all numbers expressing quantities of components, molecular weights, percentages, temperatures, times, and so forth, as used in the specification or claims are to be understood as being modified by the term "about." Accordingly, unless otherwise implicitly or explicitly indicated, or unless the context is properly understood by a person of ordinary skill in the art to have a more definitive construction, the numerical parameters set forth are approximations that may depend on the desired properties sought and/or limits of detection under standard test conditions/methods as known to those of ordinary skill in the art. When directly and explicitly distinguishing embodiments from discussed prior art, the embodiment numbers are not approximates unless the word "about" is recited.

Although there are alternatives for various components, parameters, operating conditions, etc. set forth herein, that does not mean that those alternatives are necessarily equivalent and/or perform equally well. Nor does it mean that the alternatives are listed in a preferred order unless stated otherwise.

Definitions of common terms in chemistry may be found in Richard J. Lewis, Sr. (ed.), *Hawley's Condensed Chemical Dictionary*, published by John Wiley & Sons, Inc., 2016 (ISBN 978-1-118-13515-0).

In order to facilitate review of the various embodiments of the disclosure, the following explanations of specific terms are provided:

Absorption: The incorporation of a substance in one state into another of a different state, e.g., a liquid absorbed by a solid.

Activated carbon: An internally porous, microcrystalline, non-graphitic form of carbon.

Adsorption: The physical adherence or bonding of ions and molecules onto the surface of another molecule. An ion or molecule that adsorbs is referred to as an adsorbate. Adsorption can be characterized as chemisorption or physisorption, depending on the character and strength of the bond between the adsorbate and the substrate surface.

Channel: A substantially bound space in a fluidic device that allows the flow of a fluid. In some embodiments, the channel is a microchannel, wherein the substantially bound space has at least one dimension less than 1000 μm. Typically, the space has a width of less than 1000 μm and a depth of less than 1000 μm. A through-cut channel refers to a channel with a depth equal to the thickness of material in which it is formed.

Composite: A solid material composed of two or more constituent materials having different physical and/or chemical characteristics that, when combined, produce a material in which each substance retains its identity while contributing desirable properties to the whole. By "retains its identity" is meant that the individual materials remain separate and distinct within the composite structure. A composite is not a solid solution or a simple physical mixture of the constituent materials. In other words, each particle of the composite includes regions or domains of the two or more constituent materials. A core-shell composite may have a core comprising one material and a surrounding shell comprising another material. A yolk-shell composite is similar, but differs in having a space between the yolk (core) and the surrounding shell.

Covalent organic framework (COF) and covalent organic polymer (COP): A two- or three-dimensional crystalline organic structure having a plurality of organic ligands covalently bonded to one another. Covalent organic polymers (COPs) are a class of nanoporous materials constructed using reticular chemistry with organic moieties linked by strong covalent bonds similar to COFs. Some COFs are formed by self-assembly upon condensation between poly boronic acids or poly boronic acids and poly diol compounds forming boronate ester linking bonds. Examples include, but are not limited to COF-1 formed by condensation of three boronic acid molecules (below) and COF-10, a multi-ringed structure formed from condensation of boronic acid building blocks, such as 1,3,5-benzenetriboronic acid, 1,3,5-benzenetris(4-phenyboronic acid), and 4,4'-biphenyldiboronic acid, with 2,3,6,7,10,11-hexhydroxytriphenylene. Another example is COF-202, a molecular cage formed by condensation of tert-butylsilane triol with monotopic boronic acid and divergent boronic acid.

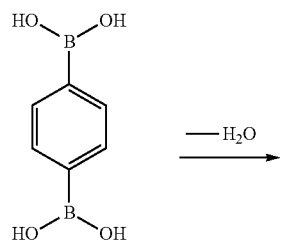

-continued

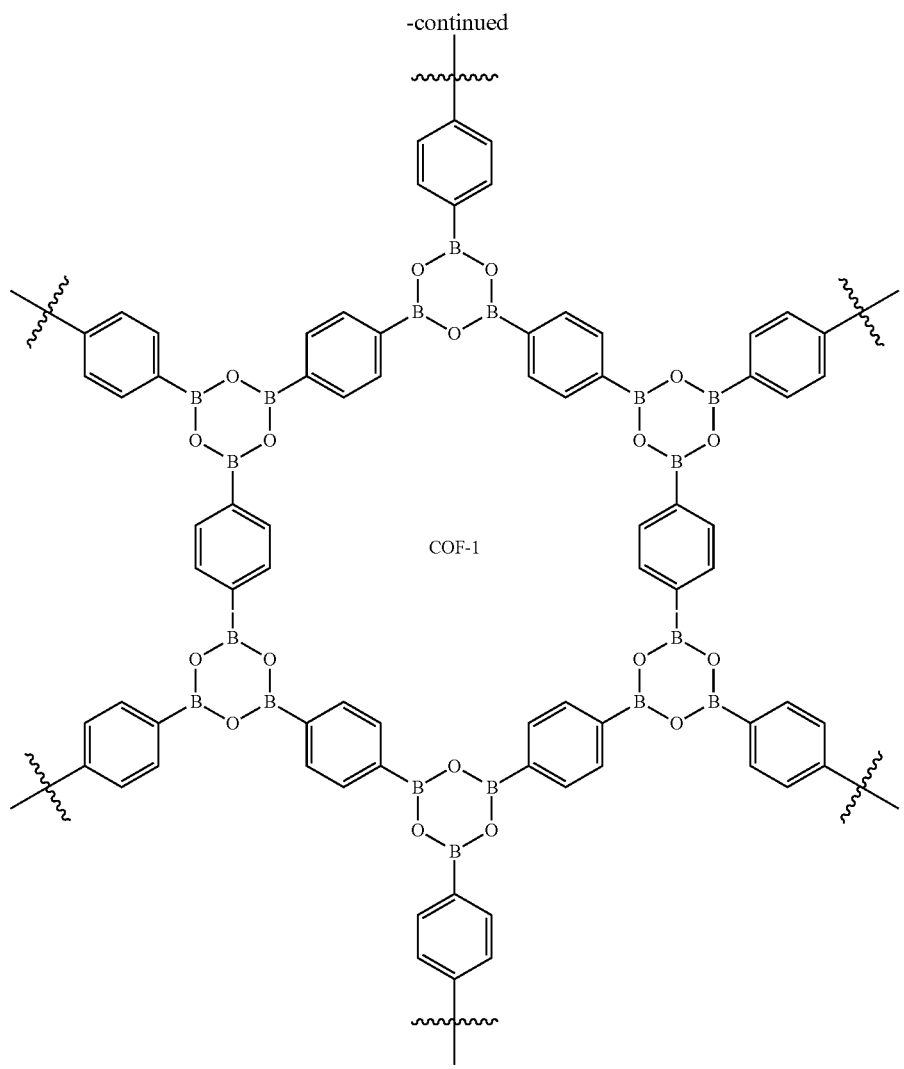

COF-1

Degrade: As used here, the term "degrade" refers to breaking one or more chemical bonds of a substance. Thermal degradation refers to breaking chemical bonds using heat.

Fluidic device: A device including one or more channels that allow flow of a fluid. A microfluidic device includes one or more microchannels that allow flow of a fluid.

GAC: granulated activated carbon

GenX: The term "GenX" refers to a technology and chemicals used to make certain fluoropolymers without the use of perfluorooctanoic acid. The technology relies on hexafluoropropylene oxide (HFPO) dimer acid and its ammonium salt. An exemplary GenX compound is undecafluoro-2-methyl-3-oxahexanoic acid (or perfluoro-2-methyl-3-oxahexanoic acid).

Hierarchical porous carbon (HPC): Three-dimensional porous carbon structures having a multimodal pore size distribution of micro-, meso-, and/or macropores.

Metal organic framework (MOF): A plurality of metal ions or clusters coordinated to polydentate organic ligands to form porous crystalline one-, two-, or three-dimensional structures. Common metals include Cr, Fe, Co, Zn, Zr, Cu, In, Ni, Ca, Al, and Mg. The organic units often are based on phenyl and polyphenyl molecules.

PFAS: per- or polyfluoroalkyl substance(s)

PFOA: perfluorooctanoic acid or perfluorooctanoate anion

PFOS: perfluorooctane sulfonate (or perfluorooctane sulfonic acid)

Pore: One of many openings or void spaces in a solid substance of any kind. Pores are characterized by their diameters. The term nanopore generally refers to pores having an average diameter of 100 nm or less. Nanopores may be further divided into micropores, mesopores, and some macropores. According to IUPAC notation, micropores are small pores with diameters less than 2 nm. Mesopores are mid-sized pores with diameters from 2 nm to 50 nm. Macropores are large pores with diameters within a range of 50-1000 nm. Porosity is a measure of the void spaces or openings in a material, and is measured as a fraction, between 0-1, or as a percentage between 0-100%.

Probe: As used herein, the term "probe" refers to a substance used to, bind, detect, and/or identify another substance in a sample.

Redox active: As used herein, the term "redox active" refers to an element, an ion, a group, or a compound, that has multiple oxidation states.

Sorption: To take up and hold by either adsorption or absorption.

Zeolite: A porous aluminosilicate mineral. Zeolites may be natural or synthetic. Zeolites may have different structures, such as fibrous zeolites, chains of single connected 4-membered rings, chains of double connected 4-membered rings, chains of 6-membered rings, and chains of tetrahedra, among others.

II. Sorbent Materials

Embodiments of the disclosed sorbent materials provide highly selective and sensitive capture and detection of PFAS. Some of the sorbent materials further are useful for remediation, or degradation, of PFAS molecules. In some embodiments, the materials include metal organic frameworks (MOFs), covalent organic frameworks (COFs), hierarchical porous carbons (HPCs), nanoporous silica, zeolites, redox-active compounds, and/or carbon supports. The sorbent material may be a composite, such as a core-shell composite, a yolk-shell composite, or a mixed composite. In certain embodiments the framework structure, functionality, pore size and volume, surface area, and open metal center densities are tailored to fine-tune the unique selectivity between the nanoporous materials and PFAS. In some examples, further selectivity is achieved when the sorbent materials are used in a flow-based detection approach as discussed infra.

In some embodiments, the sorbent material comprises a metal organic framework (MOF). The MOF may be mesoporous, microporous, or nanoporous. In some embodiments, the metal is a transition metal, a lanthanide, or an actinide. Suitable transition metals include Sc, Y, Ti, Zr, Hf, V, Nb, Ta, Cr, Mo, W, Mn, Tc, Re, Fe, Ru, Os, Co, Rh, Ir, Ni, Pd, Pt, Cu, Ag, Au, Zn, Cd, Hg, In, Ca and mixtures thereof. Suitable lanthanides and actinides include La, Ce, Pr, Nd, Pm, Sm, Eu, Gd, Tb, Dy, Ho, Er, Tm, Yb, Lu, Ac, Th, Pa, U and mixtures thereof. Nanoporous MOFs as sorbents may provide (i) selectivity due to steric and electronic recognition, (ii) high sensitivity due to their ultrahigh surface areas and/or (iii) effective transduction by using the MOFs directly on the electrodes as electrode extensions. In some embodiments, the MOF is redox-active. In certain embodiments, MOFs with immense surface areas and reactive metal centers allow for highly sensitive detection of trace quantities of target analytes, such as PFAS.

Suitable MOFs include, but are not limited to, chromium, iron, nickel, zinc, zirconium, and thorium-based MOFs. In some embodiments, the MOF comprises a chromium, iron, or zirconium terephthalate MOF (e.g., Cr-MIL-101, Fe-MIL-101, Fe-MIL-100, UiO-66, UiO-67), a zirconium fumarate MOF (e.g., MOF-801, MOF-808), a zeolitic imidazolate framework (e.g., ZIF-8, $C_8H_{10}N_4Zn$), UiO-67-BPYDC (UiO-67 functionalized with bipyridine coordination complexes), M-MOF-74 (M=Ni Co, or Zn, a MOF with 2,5-dihydroxyterephthalic acid (dhtp) ligands—$M_2$(dhtp)$(H_2O)_2 \cdot 8H_2O$), Co-MOF-74, and SCU-8 ([$TH_3$(bptc)$_3O$ $(H_2O)_{3.78}Cl \cdot (C_5H_{14}N_3Cl) \cdot 8H_2O$; $H_3$bptc=[1,1'-biphenyl]-3, 4',5-tricarboxylic acid). In some embodiments, the MOF comprises $M_3X(H_2O)_2O(BDC)_3 \cdot nH_2O$ where M is Cr or Fe, X is OH or F, BDC is 1,4-benzenedicarboxylate, and n is about 25. The MIL-101 structure contains two types of mesoporous cages (~25-29 Å) connected through microporous pentagonal (~11.7 Å) and hexagonal windows (~16 Å). Advantageously, the structural integrity of the MIL-101 MOF is preserved upon PFAS exposure, and the receptor shows high electronic affinity toward certain PFAS. For example Cr-MIL-101 exhibits high affinity for PFOS.

In any of the foregoing embodiments, the MOF may include defects or post-synthetic modifications. Defects can develop when metals or metal clusters and/or ligand linkers are missing. These unsaturated coordination sites are defects in structures behaving as acidic defects (Lewis and Bronsted) or basic defects (Lewis and Bronsted). Post synthetic modifications may be used to introduce new functional groups, such as $NH_2$, OH, $SO_3H$, SH, diamines, triamines, and combinations thereof. MOFs also, or alternatively, can be functionalized to provide redox, optical, photoactive, photocatalytic, oleophilic, oleophobic, lipophilic, lipophobic, or biocatalytic activity materials.

In some embodiments, the sorbent comprises a covalent organic framework (COF) or covalent organic polymer (COP), a class of nanoporous materials constructed using reticular chemistry with organic moieties linked by strong covalent bonds. Suitable COFs, include, but are not limited to, COFs formed from condensation between poly boronic acids or poly boronic acids and poly diol compounds. Exemplary COFs include COF-3, COF-4, COF-5, PAF-1, PAF-2, PAF-6, PAF-32, PPN-3. Suitable COPs include, but are not limited to, COP structures assembled using linkers such as boronates, imines, borosilicates, triazines, hydrazones, and other monomers and appropriate polymerization reactions using with/without catalysts.

In some embodiments, the sorbent comprises a hierarchical porous carbon (HPC). Suitable HPCs include, but are not limited to activated carbons such as granular activated carbon, Ketjen black, Norit® carbon (Sigma-Aldrich, USA), Calgon carbon (Calgon Carbon Corporation, USA), and Maxsorb® activated carbon (surface area>3000 $m^2$/g; First Quality Products, Inc., USA).

In some embodiments, the sorbent comprises a zeolite. Exemplary zeolites include, but are not limited to MS-1 (SBA-15), MS-2 (MCM-41), MS-3 (13X), MS-4 (HY), and MS-5 (SSZ-13).

In some embodiments, the sorbent comprises a redox-active material. The redox-active material may be a redox-active MOF or a Prussian blue analog having a porous framework comprising transition metal nodes linked by hexacyanoferrate ($Fe(CN)_6^{3-/4-}$) units. In some embodiments, the Prussian blue analog is nickel hexacyanoferrate (NiFe), cobalt hexacyanoferrate (CoFe), nickel/iron nitroprusside (e.g., NiFeNO, Ni[Fe(CN$_5$)NO]·2H$_2$O), or cobalt/iron nitroprusside (e.g., CoFeNO, Co[Fe(CN$_5$)NO]·2H$_2$O).

In any of the foregoing embodiments, the sorbent may be a composite. Exemplary composites include composites comprising combinations of MOFs, zeolites, covalent organic frameworks, covalent organic polymers, mesoporous silica, hierarchical porous carbon, carbon nanotubes, graphite, graphene, graphene oxides, Prussian blue materials, photocatalysts (e.g., polyoxometalates, rhenium complexes), metal oxides, metal clusters and/or polymers (e.g., PEI (polyethylenimine), PAN (polyacrylonitrile), PAA (poly[acrylic acid]), and the like). In any of the foregoing embodiments, the composite may be in the form of a core-shell composite, a yolk-shell composite, a simple mixed composite, a composite in which one component is grown on the other, or a thin film or membrane. In some embodiments, the composite is a core-shell composite, a yolk-shell composite, or a simple mixed composite.

In one embodiment, the composite comprises a MOF and a photocatalyst. In certain embodiments, the photocatalyst has an excited state oxidation potential greater than 1.5 V, such as an excited state oxidation potential within a range of from 1.6 V to 2.6 V. Exemplary photocatalysts include, but are not limited to, certain complexes of Re, Pt, Ru, and Os, as well as polyoxometalates. In some examples, the photocatalyst is a polyoxometalate. Suitable polyoxometalates include, but are not limited to, $\alpha$-$HP_3M_{12}O_{40}\cdot 6\,H_2O$, where M is W, Mo, V, Nb, Ta, or any combination thereof. In certain embodiments, M is W or Mo. In another example, the photocatalyst comprises rhenium (II) dimethylphosphinoethane.

In an independent embodiment, the composite comprises a MOF and a zeolite. Exemplary MOF-zeolite composites include composites of Cr-MIL-101 with Zeolite-4A (LTA, Linde Type A), Na-P1 (gismondine-type (GIS-type)), NaX, NaY (FAU-type) and chabazite (CHA) zeolites. Up to 5 wt % zeolite was added to strengthen the granular composite, i.e., up to 5:95 zeolite:MOF on a weight basis. In some embodiments, a granular zeolite and a small amount of solvent is added to a MOF powder. The mixture is mixed thoroughly and pressed/sieved to get particles of a desired size (e.g., 200-300 µm particles).

In another independent embodiment, the composite comprises a MOF and a polymer. Exemplary polymers include hydrophilic polymers, such as PAN (polyacrylonitrile), PAA (poly[acrylic acid]), and PEG (poly[ethylene glycol]). Up to 5 wt % polymer was added to strengthen the granular composite, i.e., up to 5:95 polymer:MOF on a weight basis. In some embodiments, a granular polymer and a small amount of solvent is added to a MOF powder. The mixture is mixed thoroughly and pressed/sieved to get particles of a desired size (e.g., 200-300 µm particles).

In still another independent embodiment, the composite is a core-shell composite comprising a MOF deposited onto another MOF structure.

In any of the foregoing embodiments, the sorbent or composite sorbent may further be attached to a support to form a supported sorbent or supported composite sorbent. In some embodiments, the support is a carbon nanostructure, such as a carbon nanotube (CNT), a carbon fiber, or a polymer. In certain embodiments, the support is a particulate support, such as a granular support. Exemplary particulate supports include, but are not limited to, polymer particulates, granular carbon, carbon nanostructures, and zeolites.

In some embodiments, a MOF or a COF is bound to a CNT. In certain examples, a CNT functionalized with —COOH is covalently bound to the MOF or COF. In other examples, a MOF or COF is physisorbed to the CNT by simple mixing. CNTs possess advantageous properties, such as high electrical conductivity, high tensile strength and flexibility, and a low thermal expansion coefficient. Additionally, the carbon is hybridized into sp, sp2 configurations with narrow gaps between the 2s and 2p electron shells. This hybridization facilitates the sensitive detection of an analyte molecule if a n electron orbital is formed due to the interaction of the analyte with carbon material specifically at the sp, sp2 hybridization. This n electron significantly increases the quantitative and qualitative measure of the analyte interaction.

In any of the foregoing embodiments, sorbent material properties may be selected and/or tailored to increase PFAS sorption capacity, influence analyte specificity, influence analyte affinity, increase bond polarization in PFAS molecules bound to the sorbent material, or any combination thereof. For example, sorbent porosity may affect uptake capacity. For example, MOF-801, UiO-66, and UiO-67 all have $Zr_6O_6$ nodes that polarize C—F and C—S bonds identically when a PFAS binds to the MOF, the sorption capacity varies with the sorbent porosity. In one example, PFOS sorption capacities followed the trend MOF-801>UiO-66>UiO-67. In another example, MOFs with identical porosity by differing metal centers, e.g., Cr-MIL-101 and Fe-MIL-101, demonstrate different PFOS affinity and bond polarizations.

In some embodiments, sorbent pore geometries, sizes, and/or topologies are tailored to improve PFAS binding affinity. In one embodiment, a MOF pore is altered by changing the length of the organic ligand, e.g., by increasing a number of phenyl rings in the ligand, to change the pore size and/or enhance PFAS-sorbent interactions. For example, Ni-MOF-74 has an average pore size of 11 Å and is formed of ligands comprising a single phenyl ring-2,5-dihydroxyterephthalic acid. However, by replacing the ligands with isomers of (dioxidobiphenyl-dicarboxylate)$^{4-}$ or isomers of dihydroxy-2',5'-dimethyl-[1,1':4',1"-terphenyl]-3,3"-dicarboxylic acid to provide ligands with two or three phenyl rings, pore sizes ranging from 17-27 Å are achieved (Zheng et al., *JACS* 2020, (142):3002-3012).

In an independent embodiment, the fluorophilic and/or hydrophilic character of a pore is tailored by using (i) redox active metal centers in a MOF, and/or (ii) including fluorophilic and/or polarizable species on the organic ligand to target affinity for the PFAS head group and/or induce bond polarizations in the fluorinated tail of the PFAS. In some examples, the organic ligand is functionalized to include —OH, —COOH, $SO_3H$, and/or —$NH_2$ moieties; functionalization may be performed during synthesis or as a post-synthesis modification (see, e.g., Example 8). In another independent embodiment, the number of active sites, such as functional groups attractive towards PFAS, is increased and/or the active centers are densified via post functionalization to provide greater PFAS affinity per unit sorbent surface area and/or to facilitate faster binding of the PFAS to the sorbent; the alterations can be performed during synthesis or as a post-synthesis modification. In another embodiment, structural stability and binding selectivity/capacity are enhanced by forming a composite sorbent comprising a MOF and a zeolite. The zeolite provides enhanced structural stability and robustness, while the MOF provides analyte specificity and binding capacity. Additional robustness is provided via a ligand-rigidification strategy. PFAS bond polarization can be tailored by varying the metals of MOFs; bond polarization may be evaluated using X-ray photoelectron spectroscopy.

Advantageously, some embodiments of the disclosed sorbent materials provide both selective and sensitive PFAS capture, detection, and/or quantification as demonstrated in the examples herein. In some examples, devices described below that include the disclosed sorbent materials were demonstrated to provide a PFAS detection limit of as low as 0.1 nM or 50 ng/L from groundwater matrices, and detection limits as low as 0.5 ng/L in buffers. In some embodiments, the disclosed sorbent materials exhibit improved uptake capacity ($\geq 10\times$) and/or faster kinetics ($\geq 10\times$) than conventional sorbents such as granulated activated carbon (GAC) or ion exchange resins. In certain embodiments, the disclosed sorbent materials also facilitate degradation of captured PFAS molecules, thus allowing the sorbent materials to be used as probes for initial capture and subsequent degradation of the PFAS.

III. Fluidic Device

Figure 4:
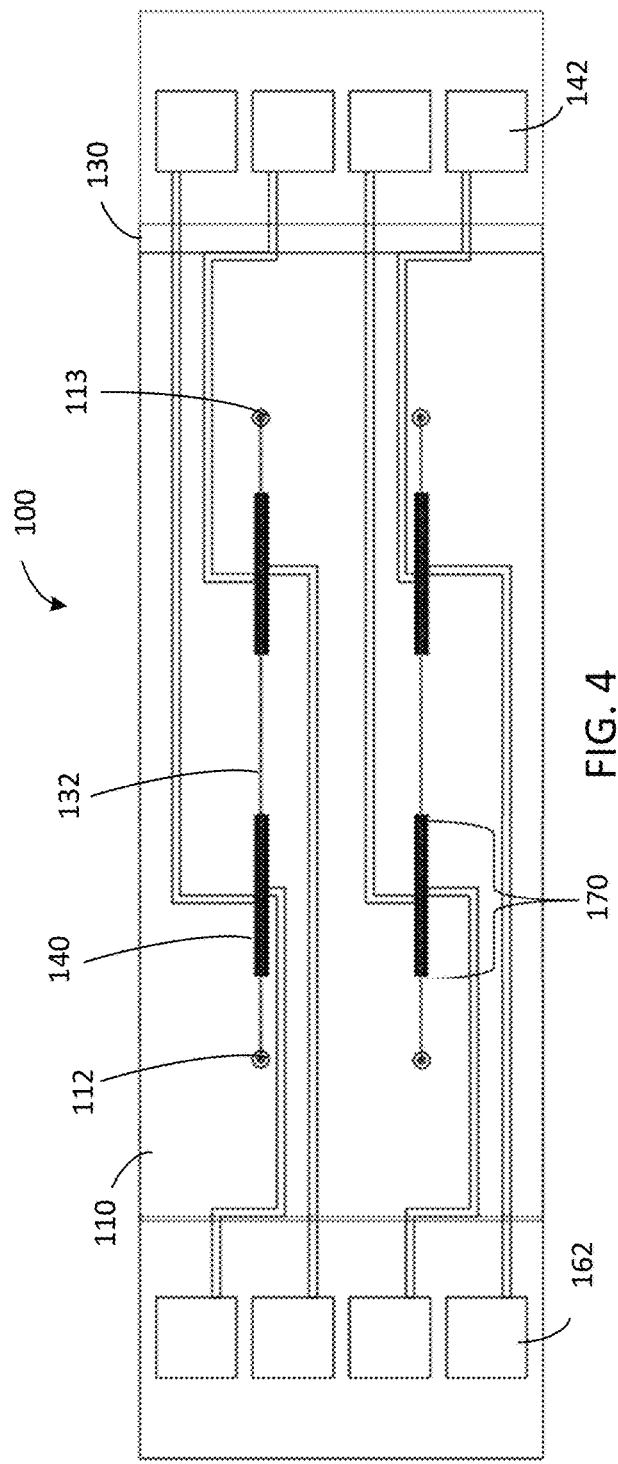
FIG. 4 is a top view of the exemplary fluidic device of FIG. 1.
Figure 5:
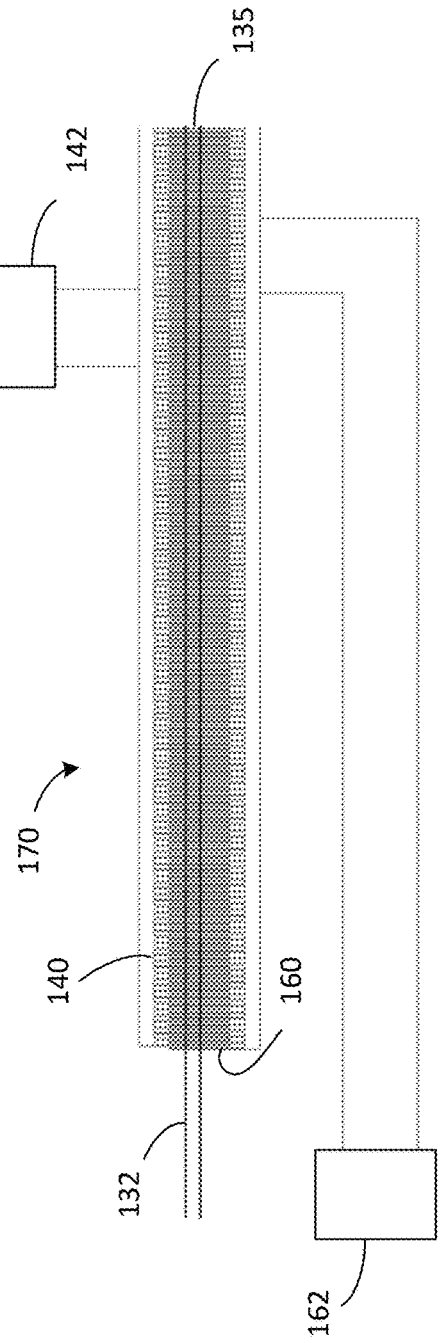
FIG. 5 is an expanded top view of sensing area 170 of FIG. 4.
Figure 6:
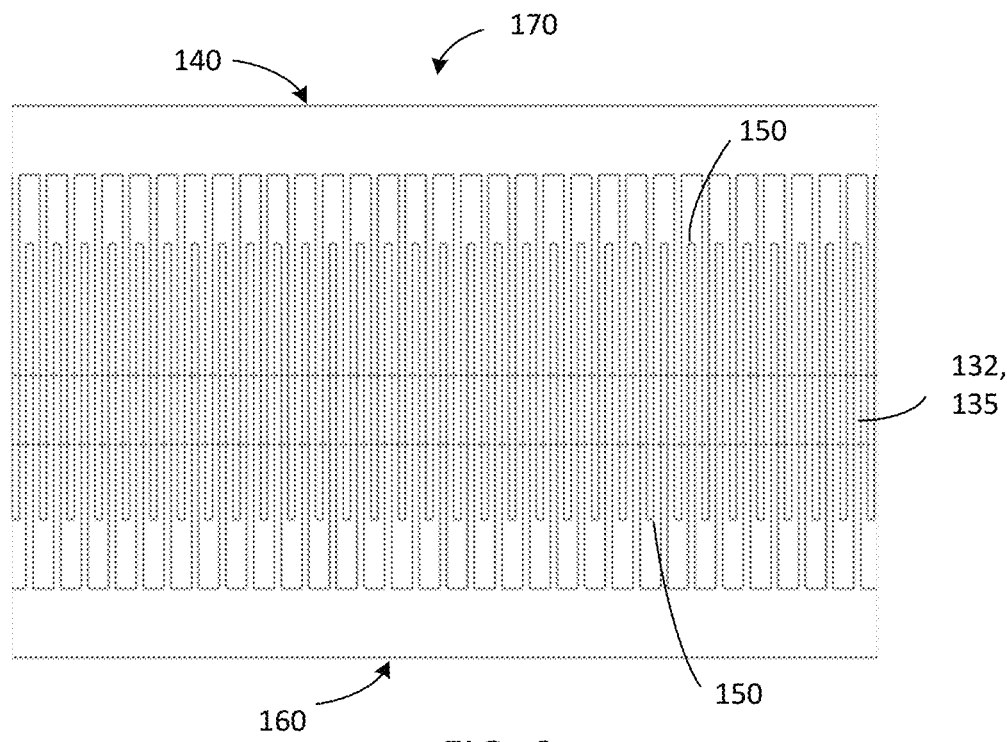
FIG. 6 is a further expanded top view of sensing area 170 of FIG. 4.

Exemplary, non-limiting embodiments of a fluidic device 100 for PFAS detection are shown in FIGS. 1-6. The fluidic device 100 includes an upper planar substrate 110, a lower planar substrate 120, and a thin film 130 between the upper planar substrate 110 and lower planar substrate 120. The thin film 130 includes a channel 132 cut therethrough. A plurality of probes 135 as disclosed herein is disposed within the channel 132. The probes comprise a sorbent material as disclosed herein. An upper sensing area 140 comprising a plurality of spaced-apart electrodes 150 is disposed on a lower surface 111 of the upper planar substrate 110. A lower sensing area 160 comprising a plurality of spaced-apart electrodes 150 is disposed on an upper surface 121 of the lower planar substrate 120. Electrodes 150 of the lower sensing area 160 are non-planar with electrodes 150 of the upper sensing area 140 when the device 100 is assembled. In some embodiments, electrodes 150 of the lower sensing area 160 are positioned to be interdigitated with electrodes 150 of the upper sensing area 140 when the device 100 is assembled. When the device 100 is assembled, a portion (a lengthwise portion) of the channel 132 is positioned between the upper sensing area 140 and lower sensing area 160 (e.g., as shown in FIGS. 1 and 3-5). Collectively, the upper sensing area 140, lower sensing area 160, portion of the channel 132 therebetween, and probes 135 form a sensing region 170 (e.g., as shown in FIGS. 4-6). An upper conductive connector 142 is connected to the upper sensing area 140 and a lower conductive connector 162 is connected to the lower sensing area 160. The upper and lower conductive connectors allow an electric field to be applied across the electrodes 150 of the upper sensing area 140, the channel 132, and the electrodes 150 of the lower sensing area 160.

The upper planar substrate 110 further comprises an inlet hole 112 defined by the upper planar substrate, the inlet hole 112 aligned with and in fluid communication with a first end 133 of the channel 132 (e.g., as shown in FIGS. 1-2). The upper planar substrate 110 also comprises an outlet hole 113 defined by the upper planar substrate, the outlet hole 113 aligned with and in fluid communication with a second end 134 of the channel 132. In any of the foregoing embodiments, an inlet flow port 114 may be in fluid communication with the inlet hole 112, and an outlet flow port 115 may be in fluid communication with the outlet hole 113 (e.g., as shown in FIGS. 1-2).

In any of the foregoing embodiments, the device 100 may include one or a plurality of upper sensing areas 140, upper conductive connectors 142, channels 132, lower sensing areas 160, lower conductive connectors 162. Each channel 132 will pass between at least one upper sensing area 140 and one lower sensing area 160. In some embodiments, each channel 132 passes between two or more upper sensing areas 140 and lower sensing areas 160, wherein the upper sensing areas 140 are arranged in series and the lower sensing areas 160 are arranged in series. Each upper sensing area 140 is connected to an upper conductive connector 142. Each lower sensing area 160 is connected to a lower conductive connector 162. The upper planar substrate 110 includes an inlet hole 112 for each channel 132, the inlet hole 112 aligned with an in fluid communication with a first end 133 of the channel 132. The upper planar substrate 110 further includes an outlet hole 113 for each channel 132, the outlet hole 113 aligned with an in fluid communication with a second end 134 of the channel 132. Optionally, an inlet flow port 114 is in fluid communication with each inlet hole 112, and an outlet flow port 115 is in fluid communication with each outlet hole 113.

In the exemplary embodiment of FIGS. 1-6, the device 100 includes two channels 132. Two upper sensing areas 140 are arranged in series above each channel 132, and two lower sensing areas 160 are arranged below each channel 132. An inlet hole 112 and outlet hole 113 are aligned with and in fluid communication with each channel 132. It is understood, however, that device 100 may include one channel 132 or more than two channels 132, where the number of channels may be limited only by the size of the device. Furthermore, it is understood that one, two, or more upper sensing areas 140 and lower sensing areas 160 may be arranged in series, respectively, above and below each channel 132. The number of sensing areas may limited only by the size of the device. An upper conductive connector 142 is connected to each upper sensing area 140, and a lower conductive connector 162 is connected to each lower sensing area 160.

In any of the foregoing embodiments, the upper substrate 110 and lower substrate 120 may be constructed of a nonconductive material. In some embodiments, the upper substrate and/or lower substrate are constructed of glass or silica. For example, the upper and lower substrates may be glass plates or slides. At least one inlet hole 112 and at least one outlet hole 113 are formed in the upper substrate 110.

In any of the foregoing embodiments, the thin film 130 between the upper substrate 110 and lower substrate 120 may be a nonconductive material. Suitable nonconductive materials include, but are not limited to, nonconductive plastics, such as polyester, polyolefins (e.g., polyethylene, polypropylene), and the like. In some embodiments, the thin film 130 is a double-sided adhesive tape adhered to the lower surface 111 of the upper substrate 110 and the upper surface 121 of the lower substrate 120. In some embodiments, the thin film 130 has a thickness (inclusive of any adhesive) within a range of from 50 μm to 1 mm, such as a thickness within a range of 50-500 μm, or 100-250 μm. At least one channel 132 is cut through the thin film 130, such that the channel 132 has no upper or lower surface. The channel 132 has a length that is less than a length of the thin film 130. In any of the foregoing embodiments, the channel may have a width within a range of from 100 μm to 1 mm, such as from 100-500 μm. In certain working embodiments, each channel had a width within a range of 100-500 μm, a length of 6 cm, and a depth of 240 μm (i.e., the thin film 130 had a thickness of 240 μm).

The plurality of electrodes 150 in the upper sensing area 140 and the plurality of electrodes 150 in lower sensing area 160 each comprise two or more electrodes 150. In some embodiments, the number of electrodes in each sensing area may range from 2-500 electrodes, such as from 5-500, 50-500, 100-500, 100-400, or 200-300 electrodes. In certain embodiments, the number of electrodes in each upper sensing area 140 is the same or similar (±10%) to the number of electrodes in the corresponding lower sensing area 160. In any of the foregoing embodiments, the electrodes may be formed of any suitable conductive material. In some embodiments, the electrodes are metal or conductive carbon. In certain embodiments, the electrodes are metal, e.g., Au, Ti, Pt, or a combination thereof. When the channel 132 is a microchannel, the electrodes 150 may be microelectrodes. In such embodiments, the electrodes have a width within a range of 5-50 μm, such as 5-15 μm. The spacing between electrodes may range from 10-100 μm, such as from 10-50 μm or 20-40 μm. The electrodes 150 extend at least partially across, and preferably completely across, the channel 132. In some embodiments, the electrodes 150 have a length that exceeds a width of the channel 132. Each electrode may have the same length. In some embodiments, the electrodes have a length within a range of from 150-1000 μm, such as from 200-1000 μm, 250-750 μm, or 400-600 μm. In certain working examples, the electrodes were gold and had a width of 10 μm, a length of 500 μm, and spacing of 30 μm between electrodes, with 250 electrodes in each sensing area. As described above, the electrodes 150 of the upper sensing area 140 and lower sensing area 160 are interdigitated. Thus, the electrodes 150 may be interdigitated microelectrodes (IDμEs).

In some embodiments, IDμEs provide a greater signal-to-noise ratio than comparable macro-sized electrodes. A reduction in the size or area of an electrode leads to a concomitant decrease in mass transport to the electrode, and hence, the signal decreases. However, the power drop and the background currents decrease faster. Hence, comparing the signal to noise ratio, the noise reduces faster than the reduction in signal, leading to a significant improvement in signal to noise ratio for IDμEs. In some embodiments, IDμEs as electrochemical transducers offer the advantages of high collection efficiencies, a low response time that favors rapid detection, low ohmic drop, easy fabrication over multiple substrates, readiness for miniaturization and elimination of the need for a reference electrode allowing easy integration with microfluidic chips for multiplexed analytical platforms.

In any of the foregoing embodiments, the interdigitated electrodes may be non-planar, such as non-planar IDμEs (NP-IDμE). By non-planar, it meant that the plurality of electrodes 150 in the upper sensing area 140 is not coplanar with the plurality of electrodes 150 in the lower sensing area 160. Advantageously, the NP-IDμE ensures electric field penetration throughout the fluidic channel width and height. This feature facilitates use of low-conductivity probes, such as Cr-MIL-101. Due to the low conductivity of some MOFs, the electric field penetration from IDμE into the MOF may be minimal and close to the probe surface. When using EIS techniques to detect PFAS binding (as discussed in detail below), This limited electric field penetration from planar IDμE would limit the ability to detect minute changes in charge transport, and consequently minute changes in target concentrations. The non-planar IDμE chosen in this work ensures the penetration of the electric field across the whole probe, significantly enhancing sensitivity of the device by being able to capture any change in interfacial charge transport at any position within the probe, while also preserving the benefits of the probe for selective target capture.

An upper conductive connector 142 is connected to each upper sensing area 140 and a lower conductive connector 162 is connected to each lower sensing area 160. Suitable conductive materials for the connectors include, but are not limited to, metals and conductive carbon. In some embodiments, the conductive connectors 142, 162 comprise one or more metals, e.g., Au, Ti, Pt, or a combination thereof. In certain examples, the conductive connectors comprised a 10 μm titanium layer and a 100 μm gold layer.

In any of the foregoing embodiments, the device 100 may further include an inlet flow port 114 in fluid communication with each inlet hole 112 and an outlet flow port 115 in fluid communication with each outlet hole 113. The inlet and outlet flow ports may be constructed of any material that is inert to a fluid flowed through the port. In some embodiments, the inlet and outlet flow ports are constructed of a plastic, e.g., polyetheretherketone (PEEK), polytetrafluoroethylene (PTFE), polyvinylidene fluoride (PVDF), polyurethane, polypropylene, polyethylene, or the like.

Figure 7:
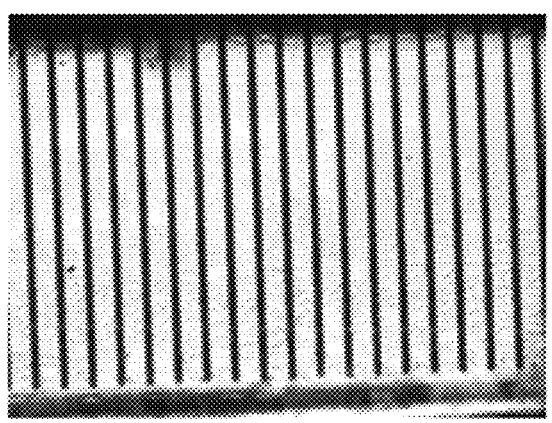
FIG. 7 is an optical microscope image of an empty microfluidic channel with interdigitated electrodes.
Figure 8:
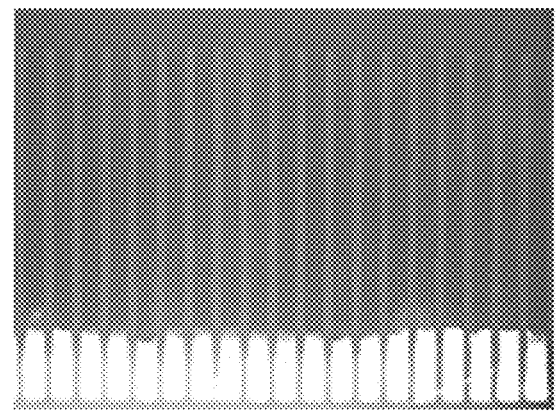
FIG. 8 is an optical microscope image of a microfluidic channel with interdigitated electrodes, the channel filled with Cr-MIL-101 probes.

A plurality of probes 135 is disposed in the channel 132. The plurality of probes may be disposed in a portion of the channel or along the entire length of the channel. The probes comprise a sorbent material as disclosed herein. In some embodiments, the sorbent material is a composite sorbent or a supported sorbent. A portion of the channel including one or more probes of the plurality of probes is located in the sensing region 170 and extends between the upper sensing area 140 and the lower sensing area 160. In one embodiment, the plurality of probes 135 includes probes of a single composition. In an independent embodiment, the probes 135 includes probes of two or more compositions, e.g., two or more different MOFs. When the device includes a plurality of sensing regions 170 along a channel 132, the plurality of probes 135 in a sensing region 170 may have the same composition or a different composition than probes 135 in other sensing regions along the same channel 132. When the device 100 includes a plurality of channels 132, the probes 135 disposed in each channel 132 may have the same composition or a different composition than probes 135 in other channels 132 of the device. Advantageously, individual probes 135 have a porosity that permits fluid flow through the channel 132, or there are spaces between probes that permit fluid flow through the channel 132. FIGS. 7 and 8 are optical microscope images showing an empty microfluidic channel 132 with interdigitated electrodes 150 (FIG. 7), and the channel filled with Cr-MIL-101 probes 135 (FIG. 8).

In some embodiments, the probes 135 comprise a MOF capable of binding at least one PFAS. In certain examples, the probe 135 comprises Fe-MIL-101 or Cr-MIL-101. In some embodiments, the probe 135 comprises a composite sorbent, a supported sorbent, or a supported composite sorbent. Suitable supporting materials include, but are not limited to, carbon supports, polymers, and zeolites. In some embodiments, the carbon support is a carbon nanotube or a carbon fiber. In certain embodiments, the MOF is bound to a carbon nanotube using covalent bonding (e.g., via a condensation or coupling reaction) or physisorption (by simple mixing). In some examples, the MOF is covalent bound to a CNT using COOH-functionalized CNTs where the MOF is tethered to the COOH groups. As previously discussed, the probes 135 in each sensing region 170 may be different or a single sensing region may include a plurality of different probes 135. The probes may be chosen to selectively bind particular PFAS. As one non-limiting example, a first sensing region may comprise probes that selectively bind PFOA and another sensing region may comprise probes that selectively bind PFOS.

Figure 9A:
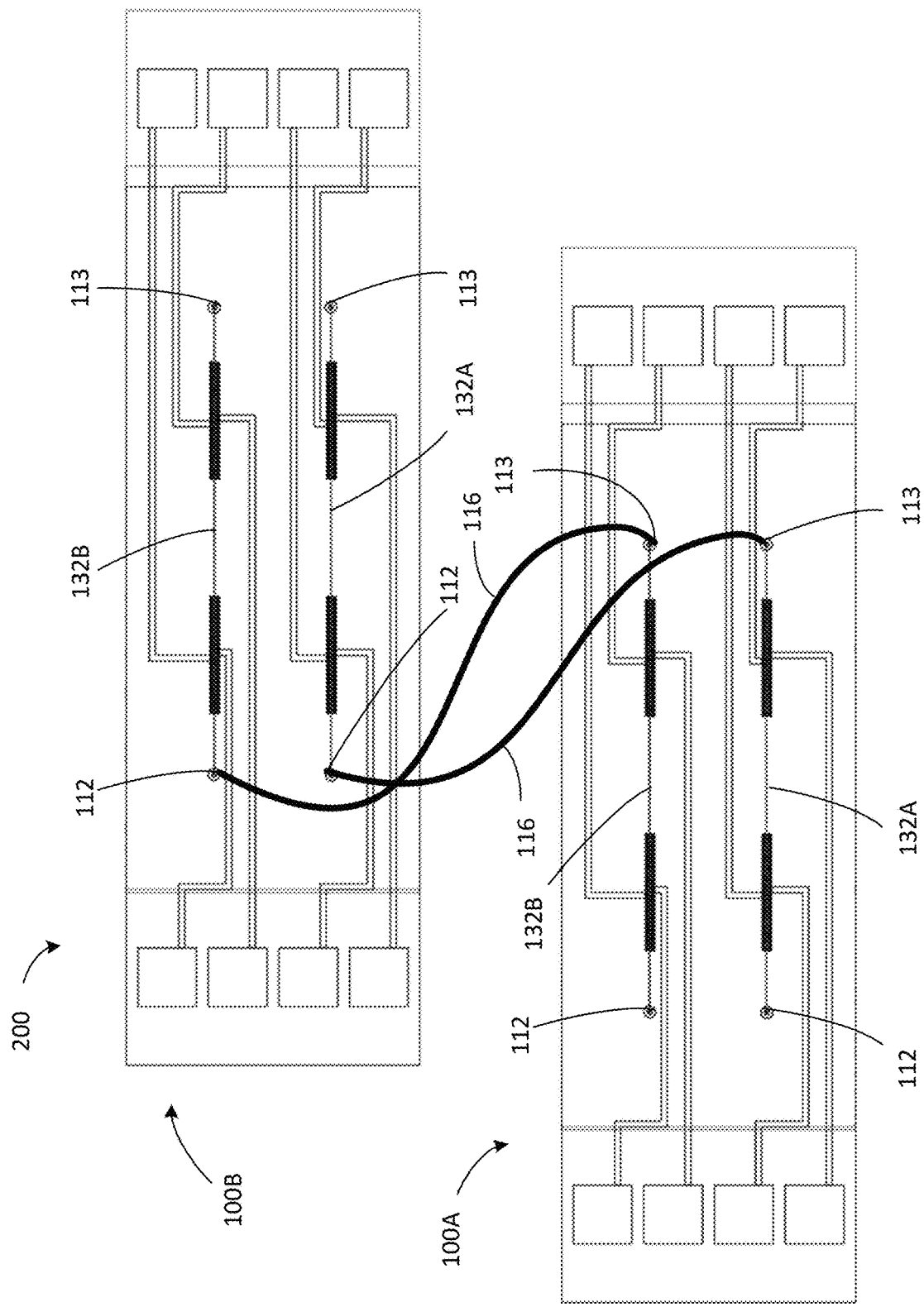
FIGS. 9A and 9B are top views of systems including two exemplary fluidic devices connected in series (9A) or in parallel (9B).
Figure 9B:
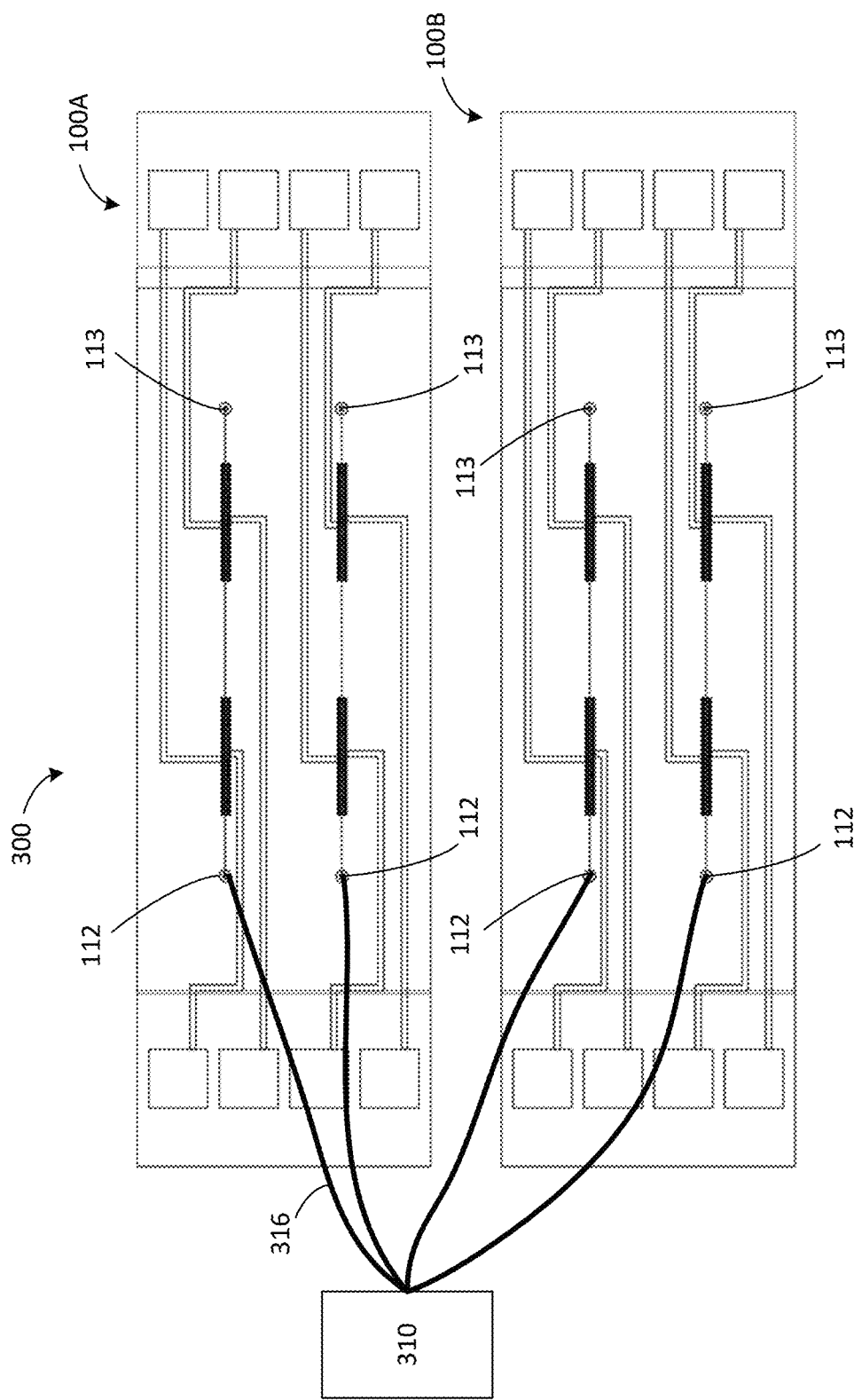
Figure 10:
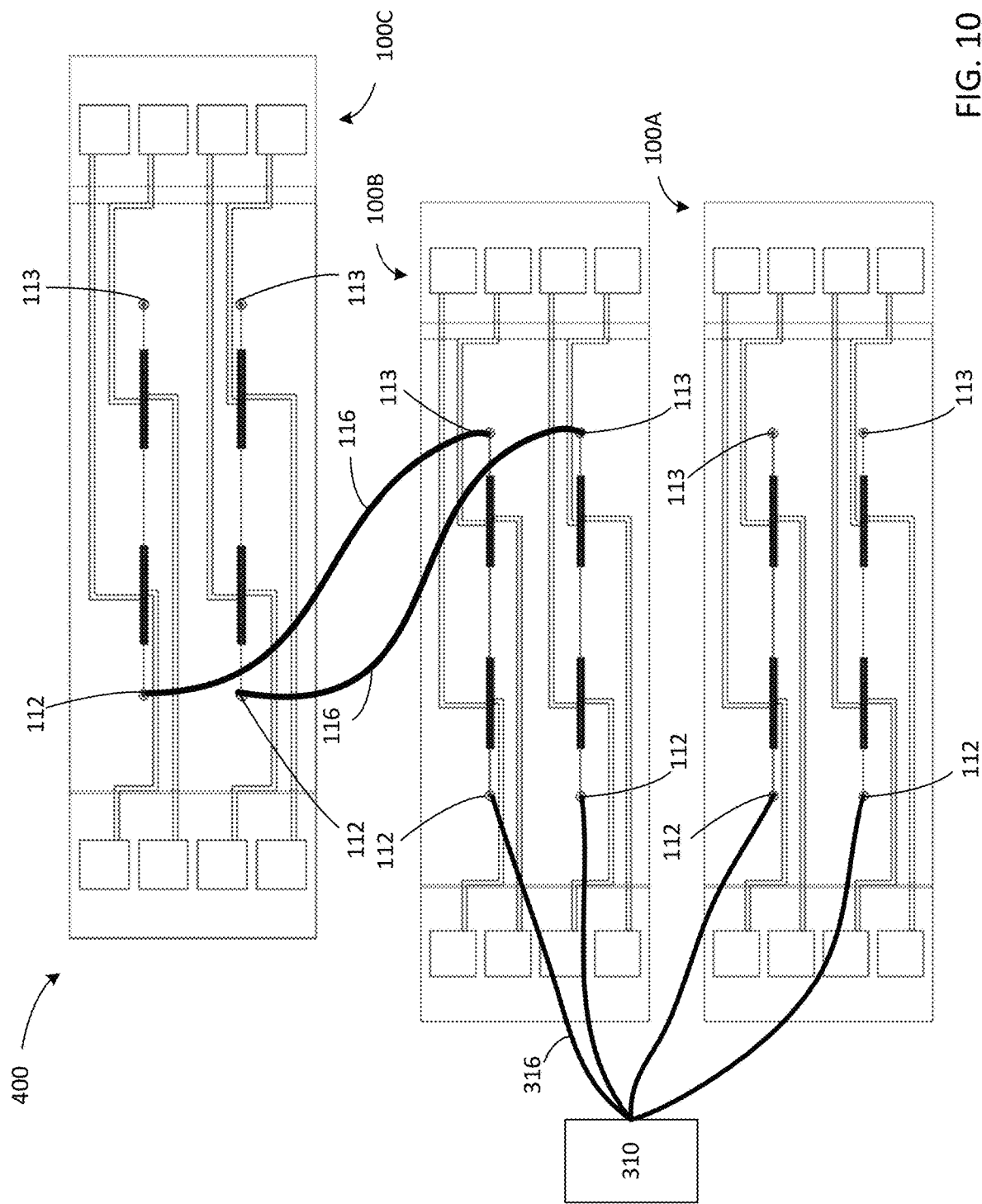
FIG. 10 is a top view of a system including three exemplary fluidic devices with both parallel and serial connections.

FIG. 9A shows one exemplary embodiment of a system 200 in which two fluidic devices 100A, 100B are connected in series. In the embodiment of FIG. 9A, a fluid flows through an outlet hole 113 of a first fluidic device 100A, through a conduit 116, and into an inlet hole 112 of a second fluidic device 100B. Such an arrangement may facilitate sequential capture, detection, and optionally quantification of several PFAS from a single fluid sample. When each fluidic device 100A, 100B includes two channels 132A, 132B, such as those shown in FIG. 9A, a different fluid sample may be flowed through each channel. FIG. 9B shows an exemplary embodiment of a system 300 in which two fluidic devices 100A, 100B are connected in parallel. The system 300 comprises a fluid reservoir 310 and a plurality of conduits 316 configured to deliver fluid to the inlet holes 112 of each fluidic device 100A, 100B. Such an arrangement may facilitate simultaneous capture, detection, and optionally quantification of several PFAS from a single fluid sample. FIG. 10 shows one exemplary embodiment of a system 400 in which three fluidic devices 100A, 100B, 1000 are connected. Devices 100A and 100B are connected in parallel. Devices 100B and 1000 are connected in series. A person of ordinary skill in the art understands that system 400 may include any number of devices with varying combinations of serial and/or parallel connections as desired.

IV. Capture, Detection and Quantification of PFAS

Figure 11:
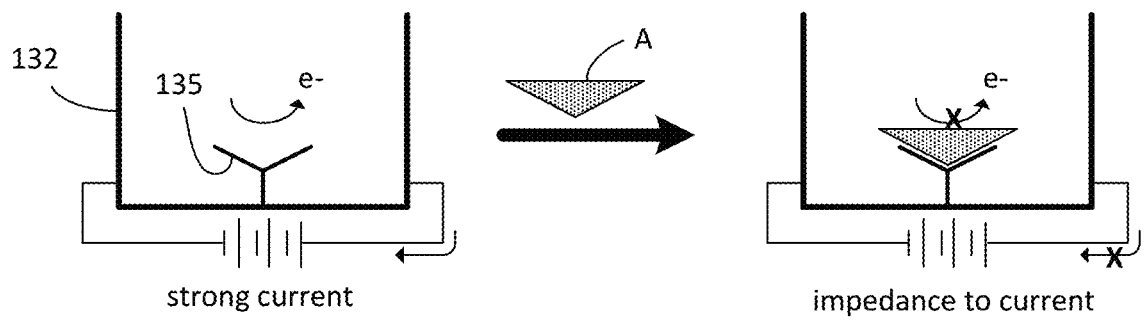
FIG. 11 is a schematic diagram showing binding of a PFAS analyte to a probe in a fluidic device with subsequence impedance of current.

Embodiments of the disclosed fluidic devices 100 exhibit a characteristic electrochemical impedance spectrum (EIS) when a fluid devoid of PFAS is flowed through the channel 132. An EIS is obtained by applying an electric field across the channel 132 via the electrodes 150 in the upper and lower sensing areas 140, 160 of the sensing region 170. A plurality of probes 135 is disposed within the portion of the channel 132 located in the sensing region 170. When a PFAS analyte ("A") is sorbed to probes 135 within the sensing region, the impedance across the channel 132 changes (FIG. 11). EIS detects changes in charge transport. Accordingly, the EIS changes relative to an EIS obtained when no PFAS molecules are sorbed to probes within the sensing region. When a concentration of PFAS in a fluid sample flowed through the sensing region is sufficiently low to not exceed a binding capacity of the probes, the magnitude of the EIS change is proportional to the PFAS concentration in the fluid sample. In some embodiments, the sample is groundwater. Embodiments of disclosed devices and method may be used to capture, detect, and/or quantify any PFAS or combination of PFAS. A non-exhaustive listing of PFAS that may be captured, detected, and/or quantified is provided in Table 1 above. In some embodiments, the PFAS comprises PFOA (perfluorooctanoic acid), PFOS (perfluorooctane sulfonate), PFPeA (perfluoropentanoic acid), PFDA (perfluorodecanoic acid), PFBA (perfluorobutanoic acid), PFOSA (perfluorooctane sulfonamide), FtS 8:2 (8:2 fluorotelomer sulfonic acid), PFHxS (perfluorohexyl sulfonate), PFBS (perfluorobutyl sulfonate), perfluoro-2-methyl-3-oxahexanoic acid (GenX), or any combination thereof.

Embodiments of a method for using a fluidic device as disclosed herein include flowing a sample through a channel of the device, thereby sorbing PFAS to probes disposed within the channel, applying an electric field across a sensing region of the device, and obtaining a post-sample EIS of the sensing region, i.e., an EIS after contact with the sample. The sample may comprise, or be suspected of comprising, one or more PFAS. The post-sample EIS of the device is compared to a pre-sample EIS of the sensing region obtained prior to flowing the sample through the channel.

If the device includes a plurality of sensing regions 170, a pre-sample EIS and post-sample EIS may be obtained from each sensing region. A difference between the post-sample EIS and the pre-sample EIS indicates presence of the PFAS in the sample. The probes disposed in the portions of the channel in each sensing region may have a different composition than probes in other sensing regions.

In some embodiments, the method further includes quantifying the difference between the post-sample EIS and the pre-sample EIS to provide a quantified difference. A concentration of PFAS in the sample is determined based on the quantified difference.

In any of the foregoing embodiments, applying the electric field across the sensing region may comprise applying the electric field across the electrodes 150 of the upper and lower sensing areas 140, 160. At low frequencies (Hz), the electrical current is dominated by the charge transfer resistance (electron transfer between electrode surface and electrolyte) while at high frequencies (kHz to MHz) the double layer capacitor (interfacial polarization of the electrolyte) dominates. Typically, the electrode surface or the charge transfer resistance is of interest with EIS-based sensors as it is a true representation of the signal from the sensor (generally an electrode). The double layer capacitor is seen as a parasitic signal and the most significant source of noise in EIS. Hence, EIS is normally recorded at lower frequencies to overcome the parasitic double layer capacitance (Cdl). However low frequency EIS is plagued by low signal to noise and environmental disturbances. Thus it becomes significantly more challenging to measure low frequency EIS and detect subsequent changes in the EIS spectrum. Further, the time needed to measure EIS at low frequency increases from instantaneous at high frequency EIS to a couple of minutes at low frequency EIS. To address these issues, the probes were packed within the channel, resulting in disruption of the double layer capacitor due to the higher Peclet Number (convective fluxes) from the nanoporous packing density akin to a packed bed reactor. This shifts the relaxation frequency of the double layer capacitor to high frequency (MHz) allowing observation of the charge-transfer or polarization resistance at much higher frequencies. In any of the foregoing embodiments, the electric field may have a frequency within a range of from 1 Hz to 100 MHz, such as from 1 kHz to 11 MHz In some embodiments, the electric field has a strength of from 1 mV to 1V, such as from 100 mV to 500 mV. In some embodiments, the interdigitated electrodes introduce a dielectrophoretic (DEP) field that has a component of the electric field opposes the drag force from the fluid flow even under large shear forces (high flow rates). In certain working examples, the DEP field was 104 V/cm at an applied voltage of 500 mV.

In any of the foregoing embodiments, a flow rate through the channel may be within a range of from 0.1 µL/minute to 100 µL/minute, such as from 0.1-50 µL/minute, 0.1-10 µL/minute, 0.1-5 µL/minute, 0.1-3 µL/minute, 0.5-2 µL/minute, or 0.5-1.5 µL/minute. The flow rate may be selected, in part, based on a width or cross-sectional area of the channel. For example, as the channel width or cross-sectional area is increased, the flow rate also may be increased. As the flow rate increases, a shear force produced between the flowing sample and the probes within the channel increases. In some embodiments, the flow rate is selected so that the shear force does not inhibit or prevent adsorption of the PFAS molecules to the probes. In certain embodiments, the shear force as the fluid flows through the probes in the channel at the selected flow rate has a magnitude similar to a hydrogen bond. Adjusting the flow rate allows binding of the desired analyte(s) while washing off interfering species that have a comparatively weaker, non-specific affinity toward the probes. Thus, the selected flow rate and resulting shear force differentiates and controls nonspecific interactions from specific interactions, as well as differentiating strong binding from weak binding, thereby minimizing false positives and/or false negatives.

Embodiments of the disclosed method and fluid device provide advantages not found in other methods and devices for detecting and quantifying PFAS. For example, the nanoporous nature of the probes disposed in the channel provides a shear force as a fluid sample flows through the channel, thereby tremendously increasing sensitivity of the platform compared to devices where the fluid does not flow through a bed of probes. In some embodiments, the interdigitated electrodes are IDµEs, which provide a high signal-to-noise ratio and increase sensitivity compared to macro electrodes. Nanoconfinement effects further boost the signal. Additionally, the nanoporous geometry of the probes increases convective transport of the analyte to the probe, reducing diffusion times and making the platform more rapid. Moreover, convective transport enhancement from the shear flow removes the parasitic double layer capacitance signal, allowing rapid measurement of binding with significantly reduced noise compared to other devices with macroelectrodes and/or without fluid flow through nanoporous probes.

In any of the foregoing embodiments, the disclosed device and method may provide a sensitivity lower than the EPA health advisory level of 70 ng/L. In some embodiments, the disclosed device and method detect PFAS at concentrations as low as 0.1 nM, such as detection of PFOS at concentrations of 50 ng/L, from groundwater matrices. Detection limits as low as 0.5 ng/L (0.5 ppt) were obtained with solutions comprising PFOS in PBS buffer and probes comprising a MOF. While other methods (e.g., LC/MS/MS, TOP, PIGE spectroscopy) may have similar sensitivity, such methods are not suitable for use outside of a laboratory environment. Advantageously, some embodiments of the disclosed method can be performed without sample pretreatment and/or preconcentration steps, facilitating rapid, on-site PFAS detection.

In some embodiments, an analyte bound to a sorbent does not provide a response that allows effective detection by EIS. In certain embodiments, a redox-active sorbent may be used to bind and detect the analyte, e.g., a PFAS, through effective signal transduction from the sorbent with or without use of a fluidic device as disclosed herein. Instead, a sample comprising, or suspected of comprising a PFAS is combined with a redox-active sorbent or a composite sorbent comprising a redox-active material, whereby the PFAS binds to the sorbent. Detection of the PFAS is performed by measuring a redox signal of the PFAS-sorbent, whereby presence of the PFAS is indicated by a difference, or perturbation, in the redox signal compared to a redox signal of the sorbent in a sample that does not comprise a PFAS. Suitable redox-active sorbents and composite sorbent components include redox-active MOFs. Detection limits as low as 1.3 ng were obtained with solutions comprising PFOA and probes comprising a redox-active MOF.

In any of the foregoing embodiments, detection can be performed using a multiplex device including multiple sorbents on a single platform. In some embodiments, the multiplex device is a fluidic device 100 as described herein where different probes are included in a plurality of sensing areas 170. In other embodiments, the device may comprise a plurality of microelectrodes with a series of separate electrode compartments for each analyte. Each compartment may include a sorbent with an affinity for one or more particular PFAS. Each compartment may have an independent readout. In certain examples, the readout comprises data to generate an EIS spectrum or a voltammogram. In some embodiments, the device or compartments thereof may be rinsed and the sorbents regenerated for further use. In certain embodiments, the device is automated and is programmed to start a regeneration cycle once the analyte capture reaches a value close to saturation or the entire sample has been analyzed. The regeneration cycle may include rinsing the sorbent and/or setting a voltage of the device to a strongly oxidizing potential value to oxidize captured PFAS molecules and release them.

In any of the foregoing embodiments, the method may be performed with a system comprising a plurality of devices connected in parallel and/or serial mode. In serial mode, multiple devices are connected end to end with the flow from one device entering into the next device and so forth (e.g., as shown in FIG. 9A). In parallel mode, a single flow is split into multiple devices (e.g., as shown in FIG. 9B). Combinations of devices connected in parallel and series can be merged to form a device network akin to an electrical resistance circuit (e.g., as shown in FIG. 10).

Each device in the network can have each channel, or even each sensing region along a channel, packed with a different material. Using the overall response of the network, the selectivity, and the sensitivity of the network to a particular PFAS or emerging contaminant can be tremendously enhanced. Further, the shear forces through each device can be altered by changing the device architecture (e.g., channel width, channel depth, probe identity) also, which can increase the selectivity or the sensitivity of the device. The shear force from the flow of the liquid can tremendously enhance the selectivity of the device. The flow can be controlled to use it like a tuning mechanism to increase or decrease the shear force and hence the selectivity. Post selectivity, the fluid in the device can be exchanged with a different background fluid that allows for enhancement in the sensitivity of the device.

V. Capture and Remediation of PFAS

Complete PFAS mineralization is a preferred approach in PFAS removal strategies. Presently used technologies for PFAS degradation include ex situ techniques such as incineration or direct destructive water treatment processes such as smoldering, photo- and electrocatalysis, biological degradation, plasma cleaning, chemical oxidation, and sonolysis. Incineration is most widely used, and is generally applied to source solutions or various commercial capture sorbents, such as granular activated carbon (GAC) or ion exchange resins (IX), following contact with PFAS-contaminated samples. However, the process is expensive and ineffective at providing complete PFAS destruction. Because the C—F bond energy is among the highest in nature, incineration often results in generation of shorter molecules rather than complete mineralization. The shorter molecule byproducts retain significant toxicities. GAC and IX sorbents capture PFAS through spatial affinity, where PFAS bond polarity are not impacted; consequently, PFAS destruction in these sorbents remains equally energy demanding as pristine PFAS. GAC and IX sorbents also are less effective at capturing shorter-chain PFAS. Additionally, the PFAS capture capacity of these sorbents is too low to be cost effective; therefore, large sorbent quantities and secondary treatment is needed to meet regulatory requirements. This necessitates subsequent incineration of burdensome quantities of PFAS-laden solids, as well as the potential environmental release of fluorinated air contaminants. Extension of incineration approaches to wet wastes and concentrated solutions is even more inefficient due to the greater energy demands of vaporizing aqueous solutions further impeding their practical in situ applicability. The foremost challenge of direct destruction approaches is destroying highly recalcitrant compounds that are typically present at relatively low concentrations in water—this process inherently demands excessive energy input.

Some embodiments of the disclosed sorbent materials and methods solve these problems. A PFAS is captured, or bound, by a sorbent material as disclosed herein, forming a PFAS-sorbent complex. In any of the foregoing embodiments, the PFAS may be any PFAS or combination of PFAS, such as any PFAS in Table 1 above. In some embodiments, the PFAS comprises PFOA (perfluorooctanoic acid), PFOS (perfluorooctane sulfonate), PFPeA (perfluoropentanoic acid), PFDA (perfluorodecanoic acid), PFBA (perfluorobutanoic acid), PFOSA (perfluorooctane sulfonamide), FtS 8:2

(8:2 fluorotelomer sulfonic acid), PFHxS (perfluorohexyl sulfonate), PFBS (perfluorobutyl sulfonate), perfluoro-2-methyl-3-oxahexanoic acid (GenX), or any combination thereof. Advantageously, the disclosed sorbent materials effectively capture both long-chain and short-chain PFAS.

In some embodiments, molecular bonds of a PFAS are polarized when the PFAS binds to the sorbent material, thereby lowering energy requirements for degradation or mineralization of the PFAS. Bonds that are polarized include C—F and C—S bonds. Bond polarization and binding energy reduction may be determined by any suitable method, including by X-ray photoelectron spectroscopy. The bound PFAS subsequently is degraded, e.g., via thermal or hydrothermal degradation, photocatalysis, irradiation, or any other suitable method. Degradation energy also can be assessed by differential thermal analysis and/or differential scanning calorimetry, while mechanistic interrogation can be performed with mass spectrometry and/or nuclear magnetic resonance, among other methods. The extent of degradation is assessed by any suitable method including, but not limited to, NMR and mass spectrometry techniques. In some embodiments, the PFAS is completely degraded or mineralized to form fluoride ions, carbon dioxide, and water. In other embodiments, the PFAS is partially degraded, e.g., from 25-99% of C—F, C—C, C—H, and C—S bonds in the PFAS are broken, such as from 50-99%, 75-99%, 80-99%, 90-99%, or 90-95% of the bonds.

In some embodiments, degradation is thermal or hydrothermal degradation wherein the sorbent material itself thermocatalyzes PFAS mineralization followed by concurrent sorbent material generation. Catalysis occurs through selective activation of the adsorbed PFAS via bond polarization effects induced by the sorbents. The greater the polarization of a bond, the lower the energy required for its cleavage, thereby facilitating degradation of the bound PFAS. Advantageously, in some embodiments, the sorbent material structure and properties remain unaffected by the degradation process. In some embodiments, the PFAS is completely degraded or mineralized to form fluoride ions, carbon dioxide, and water. In other embodiments, the PFAS is partially degraded, e.g., from 25-99% of C—F, C—C, C—H, and C—S bonds in the PFAS are broken, such as from 50-99%, 75-99%, 80-99%, 90-99%, or 90-95% of the bonds.

In any of the foregoing embodiments, the sorbent material may comprise a MOF (including redox-active MOFs), a COF, a COP, an HPC, mesoporous silica, a zeolite, a layered double hydroxide composite, or a combination thereof with fluorophilic affinities. In some embodiments, the sorbent material is a composite material further comprising at least one of a polymer, a zeolite, a covalent organic framework, mesoporous silica, a hierarchical porous carbon, a photocatalyst, a carbon nanotube, graphite, graphene, graphene oxide, a Prussian blue analog, or a metal oxide. In certain embodiments, the sorbent material is disposed on a support. The support may be a particulate support, such as a polymer, granular carbon, or a zeolite.

In some embodiments, a PFAS is removed from a sample by combining the sample with a sorbent to sorb the PFAS to the sorbent to form a PFAS-sorbent, and separating the PFAS-sorbent from the sample. In some embodiments, the sorbent is a composite sorbent. In certain embodiments, the composite sorbent comprises at least two different materials selected from one or more of a MOF, a COF, a COP, a zeolite, mesoporous silica, a hierarchical porous carbon, in combination with at least one of a polymer, a zeolite, a COF, a mesoporous silica, a hierarchical porous carbon, photo-catalyst, a carbon nanotube, graphite, graphene, graphene oxide, a Prussian blue analog, or a metal oxide. In some examples, the MOF does not comprise $[Zr_6O_4(OH)_4]$ and 1,4-benzodicarboxylic acid (UiO-66), or the polymer is not poly(ethylene-co-vinyl acetate). The sorbent or composite sorbent may be in a particulate form. In some examples, the particulates have a size within a range of from 100-500 μm, such as from 100-400 μm, 100-300 μm, or 100-200 μm. In some embodiments, the sorbent or composite sorbent is disposed in a bed, such as a bed within a column. The bed may be a fixed bed or a fluidized bed. In certain embodiments, combining the sample with the sorbent or composite sorbent comprises flowing the sample through or over a bed comprising the sorbent or composite sorbent, whereby the PFAS is sorbed to the sorbent. In some examples, the bed is disposed in a column and the sample is flowed up through the bed in the column using a pump (e.g., a peristaltic pump). Alternatively, the sample and sorbent may be combined and agitated for a period of time, whereby the PFAS is sorbed to the sorbent. In any of the foregoing embodiments, the sample may have a contact time with the sorbent within a range of from 30 seconds to several hours, such as from 1 minute to 24 hours, 1 minute to 10 hours, 1 minute to 5 hours, 1 minute to 2 hours, 1-60 minutes, 1-30 minutes, 1-15 minutes, or 1-5 minutes. In any of the foregoing embodiments, the sample may have a flow velocity through the column within a range of from 5-50 cm/minute (i.e., each portion of the sample travels from 5-50 cm through the column length within a minute), such as from 10-40 cm/min, or 20-30 cm/min. In any of the foregoing embodiments, the flow rate may be within a range of from 0.5-10 bed volumes per minute, such as from 1-5 bed volumes/minute or 2-4 bed volumes/minute. In any of the foregoing embodiments, the PFAS sorption process may be performed at a temperature ranging from 0° C. to 50° C., such as from 10° C. to 40° C., or 20-30° C. In some embodiments, the sorption process is performed at ambient temperature, e.g., a temperature of 20-25° C.

In any of the foregoing embodiments, the method may further comprise heating the PFAS-sorbent to a temperature $T_1$ sufficient to thermally degrade the PFAS. In some embodiments, the temperature $T_1$ is less than a temperature $T_2$ sufficient to thermally degrade "free" PFAS, i.e., PFAS not sorbed to the sorbent material. The temperature $T_2$ sufficient for degradation of free PFAS, such as PFOS, in aqueous matrices is typically within a range of 200-350° C. under autogenous pressure conditions. The process is facilitated by additives, such as persulfates and/or hydroxides to accelerate oxidative degradation through the generation of reactive radicals.

In some embodiments, $T_1$ is at least 25° C. less than $T_2$, such as at least 50° C., at least 75° C., at least 100° C., or at least 150° C. less than $T_2$. In certain embodiments, $T_1$ is within a range of from 50-200° C., such as from 50-150° C., 50-100° C. or 75-100° C. In any of the foregoing embodiments, the PFAS-sorbent may be heated to the temperature $T_1$ for a time period of from 1-24 hours, such as a time period of from 1-10 hours or 2-6 hours.

Although degradation of PFAS on the PFAS-sorbent may be performed at $T_1$ without additives, additives facilitate or accelerate the degradation process in some instances. Accordingly, in any of the foregoing embodiments, the method may comprise heating the PFAS-sorbent to the temperature $T_1$ in a solution comprising additives to accelerate degradation. Suitable additives include, but are not limited to, $H_2SO_4$, $NaHSO_5$, $Na_2S_2O_5$, $FeSO_4$, $H_2O_2$, $Na_2S_2O_4$, $NaClO_3$, $NaClO_4$, $Na_2S_2O_5$, HCl, KI, $NaNO_3$, HNO$_3$, Fe(0) (e.g., nano Fe(0)), Zn, Ni, Na$_2$SO$_3$, NaClO, Ca(OH)$_2$, K$_2$CrO$_4$, Na$_2$S$_2$O$_3$, Na$_2$CO$_3$, KMnO$_4$, K$_2$FeO$_4$, NaBH$_4$, NaOH, KOH, and combinations thereof. In some embodiments, the additives include persulfate and/or hydroxide anions. The anions may be provided by, for example, NaOH, KOH, Ca(OH)$_2$, Na$_2$S$_2$O$_8$, and the like. In certain embodiments, the additive comprises S$_2$O$_8^{2-}$ anions, which generate SO$_4^{\cdot-}$ radicals under gentler activation conditions (temperature, pressure) and possess higher oxidizing potentials than hydroxyl radicals (2.6-3.1 V for SO$_4^{\cdot-}$ radicals compared to 1.8 V for ·OH). Advantageously, persulfate anions facilitate PFAS degradation without adverse effects on the sorbent structural integrity. In some examples, PFOS bound to Cr-MIL-101 in an aqueous slurry was thermally degraded at 80° C. with MOF structural integrity preservation.

In some embodiments, the sorbent is a composite sorbent comprising a photocatalyst, such as a polyoxometalate or a complex of Re, Pt, Ru, or Os. In such embodiments, the method may further comprise exposing the PFAS-sorbent to light having a wavelength effective to excite the photocatalyst, thereby degrading the PFAS. In some embodiments, the polyoxometalate comprises α-HP$_3$M$_{12}$O$_{40}$·6 H$_2$O, where M is W, Mo, V, Nb, Ta, or any combination thereof. In an independent embodiment, the photocatalyst comprises rhenium (II) dimethylphosphinoethane (dmpe). The metal center in the photocatalysts is readily interconverted between a lower nonreactive M$^{n+}$ state and a more reactive and highly photoactive M$^{m+}$ state where m>n. Once M$^{n+}$ is oxidized to M$^{m+}$, it is activated by light to an excited state M$^{m+}$* which possesses a highly oxidizing potential, capable of oxidizing substrates beyond the oxidizing potential range of the complex in the ground state M$^{m+}$. The excited complex stores activation energy as shown below:

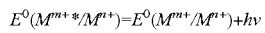

$$E^0(M^{m+}*/M^{n+}) = E^0(M^{m+}/M^{n+}) + h\nu$$

The excited photocatalyst can readily oxidize organics via charge transfer. In some embodiments, a composite sorbent comprises a MOF and a photocatalyst. A sample comprising, or suspected of comprising, a PFAS is combined with the composite sorbent, whereby the PFAS binds to the composite sorbent to form a PFAS-sorbent complex. The PFAS-sorbent complex is exposed to light having a wavelength effective to excite the photocatalyst, whereby the excited photocatalyst degrades the PFAS. For example, Re(dmpe) (PF$_6$) may be excited at a wavelength within a range of 520-540 nm, such as a wavelength of 530-535 nm.

In some embodiments, the sorbent comprises a redox-active MOF. The redox-active MOF may be used both to detect presence of PFAS and then to degrade the PFAS. The redox signal of the MOF changes when a PFAS binds to the MOF forming a PFAS-MOF complex. Detecting the presence of a PFAS comprises combining a sample with a sorbent comprising a redox-active MOF to sorb the PFAS present in the sample to the MOF to form a PFAS-sorbent, and measuring a redox signal of the combined sample and MOF, e.g., by voltammetry. The method may further include comparing the redox signal to a redox signal of the MOF in a sample that does not comprise a PFAS. Presence of a PFAS in the sample is indicated by a difference in the redox signal compared to a redox signal of the MOF in a comparable sample that does not comprise a PFAS. In some embodiments, the PFAS is oxidatively degraded by applying a strongly oxidizing potential to the PFAS-MOF complex. In certain embodiments, the oxidizing potential is within a range of from 2-2.5 eV.

In any of the foregoing embodiments, the PFAS may be completely degraded or mineralized to form fluoride ions, carbon dioxide, and water. In some embodiments, the PFAS is partially degraded, e.g., from 25-99% of C—F, C—C, C—H, and C—S bonds in the PFAS are broken, such as from 50-99%, 75-99%, 80-99%, 90-99%, or 90-95% of the bonds.

In any of the foregoing embodiments, the method may further comprise regenerating the sorbent after use. In some embodiments, regenerating the sorbent comprises rinsing the sorbent to remove any remaining degradation byproducts, e.g., by rinsing with water, a buffer (e.g., an alkaline buffer), or a suitable solvent (e.g., an alkanol, acetone, N,N-dimethylformamide). In certain embodiments, the sorbent may be reused and regenerated for at least 25 cycles, at least 50 cycles, at least 75 cycles, or at least 100 cycles.

VI. Examples

Chemicals and Materials:

Perfluorooctanesulfonic acid (PFOS; 40% in water), potassium nitrate (KNO$_3$)≥99%, dichloromethane 100%, 2-propanol 99+%, chromium (III) nitrate nonahydrate (Cr(NO$_3$)$_3$·9H$_2$O, 1 mmol), terephthalic acid (BDC, 1 mmol), nickel nitrate hexahydrate (Ni(NO$_3$)$_2$·6H$_2$O), and PFOA were obtained from Sigma-Aldrich. Potassium ferricyanide (K$_3$[Fe(CN)$_6$])≥99% was obtained from Acros Organics. Acetone and PBS buffer (1×) were obtained from VWR analytical. N,N-dimethylformamide was obtained from Alfa Aesar and was used without further purification. Granulated activated carbon (GAC) was synthesized at Pacific Northwest National Laboratory. All chemicals obtained were used as received without further purification. KNO$_3$ solution K$_3$[Fe(CN)$_6$] solutions were made by dissolving the necessary amount of reagent in ultrapure water (resistivity ≥18 MΩ). Platinum wire was 0.25 mm diameter (1.05 g/cm) and obtained from Alfa Aesar. Alumina polishing suspension, 0.05 μm, for disc electrode cleaning was obtained from Gamry. Ultrapure water (resistivity 18 MΩ) was used. Standard glass slides (1304G) with ground edges, 90° corners and size 25×75×1 mm were used for impedance measurements and were procured from Globe Scientific Inc. (USA). Double-sided polypropylene (PP) tape (90880) with SR-26 silicone pressure sensitive adhesives on both sides and a thickness of 142 μm was obtained from ARcare (USA). Indium tin oxide (ITO) coated glass slides were obtained from Thin Film Devices (USA). The Ag/AgCl reference electrode was obtained from CH Instruments, Inc. (USA) and conditioned in 1M KCl.

Measurements were performed at ambient room temperature.

Instrumentation:

Electrochemical impedance spectra (EIS) were measured in the frequency range from 100 MHz to 1 kHz with an applied AC voltage of 1V using an Agilent 4294A impedance analyzer or Precision Impedance Analyzer from Keysight Technologies (Santa Rosa, CA).

Glassy carbon disc working electrode (surface area 7.07 mm$^2$) was obtained from BASi and gold disc working electrode (surface area 3.14 mm$^2$) was obtained from CH Instruments, Inc. Ag/AgCl(s) reference electrode was obtained from CH Instruments, Inc. and conditioned in 1 M aqueous KCl for a period of at least 2 days prior to use. The solution flow was controlled using a NE-1000 New Era Pump Systems automated syringe pump. Cyclic voltammograms were conducted using a BASi EC Epsilon potentiostat. For microelectrode studies, GAC coverage was confirmed using an Amscope biological science student compound microscope.

The characterization of the materials upon PFAS capture was done using correlative microscopic, spectroscopic and diffraction measurements including solid state $^{19}$F nuclear magnetic resonance (NMR), infra-red (IR) and X-ray photoelectron (XPS) spectroscopies, transmission electron microscopies (TEM) and powder X-ray diffraction (PXRD) studies. Liquid-state $^{19}$F NMR measurements were performed on a 750 MHz NMR spectrometer (Agilent, USA) with a 5-mm wideband HXY probe at room temperature as a function of time with the time interval of 30 min up to ~40 hours. $^{19}$F NMR spectra were accumulated on the Larmor frequency of 705.83 MHz using a single pulse excitation. Solid-state $^{19}$F NMR spectra were accumulated with a 4-mm HFXY magic angle spinning (MAS) probe on a 600 MHz solid-state NMR spectrometer (Agilent, USA) on the Larmor frequency of 564.68 MHZ using a spin-echo sequence at spinning speed of 14 kHz. The $^{19}$F chemical shift for both liquid- and solid-state experiments was calibrated with $CF_3CH_2OH$ (-78 ppm) as external reference.

X-ray photoelectron spectroscopy (XPS) analysis was performed using a Kratos Axis Ultra DLD spectrometer, which consists of an Al Ka monochromatic x-ray source (1486.6 eV) and a high resolution spherical mirror analyzer. X-ray source was operated at 105 W and the emitted photoelectrons were collected at the analyzer entrance slit normal to the sample surface. The data acquisition was carried out in hybrid mode with analysis area of 700 µm×300 µm. The survey spectra were collected at pass energy of 160 eV with 0.5 eV step size and high-resolution spectra were recorded at pass energy of 40 eV with step size of 0.1 eV. The pass energy 40 eV in the 700×300 µm analysis area is referred to the FWHM of 0.7 eV for Ag 3d5/2. The charge neutralizer with low energy electrons was used to compensate the surface charge buildup at the surface. All the XPS peaks were charge referenced to C 1s binding energy at 285 eV. XPS data was analyzed by CasaXPS software using mixed Gaussian/Lorentzian (GL(30)) line shape and Shirley background correction. PXRD was used to analyze the structural integrity of the materials. Experiments were performed with a Rigaku MiniFlex 600 X-ray diffractometer (XRD). The sample was placed in a powder sample holder under ambient conditions and a pattern was collected from the 2θ range of 1-50°. The step size was 2° min$^{-1}$.

TEM data was collected using two instruments. The sample not exposed to PFOS was imaged on an FEI Titan 80-300 Environmental TEM equipped with a field emission electron gun and operated at 300 kV under low-dose conditions. Images were collected with a US 1000 2k×2k charge capture device (CCD) camera (Gatan, Inc) operated via Digital Micrograph (Gatan, Inc). The PFOS-exposed sample was imaged in a FEI Tecnai T20 TEM (Thermo Fisher Scientific) equipped with a field emission gun and operating at 200 keV in bright field and scanning TEM modes. Image capture was performed on a FEI Eagle charge capture device (CCD) camera using TIA software (Thermo Fisher Scientific). Energy-dispersive X-ray spectroscopy (EDS) was performed using an EDAX TEAM EDS Analysis System equipped with a silicon drift detector (EDAX Inc). Specimens for TEM were prepared by sonicating the suspended solids in ethanol for three minutes prior to placing a single drop on a 200-mesh copper TEM grid coated with holey carbon film (Electron Microscopy Supplies) and allowing to dry. The drop was pipetted from the upper portion of the supernatant to maximize the likelihood of capturing particles that were thin enough for TEM and electron diffraction, rather than those large enough to settle due to gravity.

Microfluidic Cell Assembly:

Initial cleaning of the chip substrate comprising standard glass slides of 25×75×1 mm$^3$ with ground edges and 90° corners involved (1) a Piranha wash for 30 minutes for removal of organic contaminants, (2) a deionized water rinse for 20 minutes to remove any residual acid or an acetone, isopropanol, methanol, and DI water (AMD) wash protocol followed by drying with a nitrogen gun, and (3) heating to 100-130° C. for 30 minutes to eliminate surface bound moisture. To promote photoresist adhesion, hexamethyldisilazane (HMDS) was spun onto the glass slides in two spins of 400 rpm for 15 s and 1000 rpm for 45 s with a ramping rate of 200 rpm/s using a Cee® spin coater (Brewer Science, Inc., Rolla, MO).

A positive tone AZ® 1512 photoresist (Microchemicals GmbH, Ulm, Germany) was spun onto the glass slide using 2 spins of 500 rpm for 10 s, 3000 rpm for 45 s and then soft-baked at 110° C. for about 60 seconds for a conformal coat of 1.39 µm on the slides.

The glass slides were exposed to the electrode mask, using contact lithography through an EVG® 620 mask aligner (EV Group, St. Florian am Inn, Austria) with an UV exposure dosage rate of 1139 J/m$^2$ or 350 J/m$^2$ for 60 seconds. The slides were developed in AZ® 300 MIF developer ((Microchemicals GmbH) for 35-45 s, followed by a deionized water wash and nitrogen drying, and the pattern was checked for accuracy under the microscope.

5 nm of titanium and 25 nm of gold was deposited at 25 µm/min and 40 µm/min, respectively (or both at 2 Å/s) on the patterned glass slides using Orion 8E Evaporator System (AJA International Inc., Scituate, MA) for electron beam (e-beam) evaporation at high vacuum pressure (7.5*10$^5$ Torr). The electrode geometry was developed post deposition using lift-off technique of immersing in acetone bath after one day.

The microchannel was constructed out of ARcare® 90445 clear polyester double-sided acrylic adhesive (Adhesives Research, Inc., Glen Rock, PA) a clear, thin and flexible plastic film coated on both sides with a medical grade pressure-sensitive adhesive, or ARcare® 90880 polypropylene double-sided tape cut to the desired size using a Cricut® machine (Cricut, Inc., South Jordan, UT). The adhesive attached the bottom and the top interdigitated electrode assemblies. A microfluidic channel was cut to dimension using the Cricut® machine. The dimensions of the channel cut were 40-48 mm (L)×500 µm (W)×full thickness (81-142 µm). The final device consisted of a top and a bottom glass slide with patterned interdigitated microelectrodes with a microchannel in the middle constructed out of the double sided tape, ARcare® 90445 polyester tape or ARcare® 90880 polypropylene tape. Inlet and out holes were drilled by a diamond drill bit onto the top electrodes patterned glass slides for introducing the flow. There was one inlet hole and one outlet hole per microchannel. The adhesive tape was first aligned on the lower patterned glass slide with the upper liner still in place on the tape. The probes comprising the MOF and CNT were loaded into the channel. In some embodiments, the probes were mixed with 0.1× PBS solution in DI water to form a slug, which was packed into the channel. The upper liner was removed to expose the adhesive once the probes were in place and the second glass slide was aligned on top. The alignment was carried out under a microscope to ensure interdigitation of the electrodes. Any air bubbles between the glass slides and the adhesive layer were removed. Plastic connectors were attached to the inlet and outlet ports using a 5-minute epoxy, which was allowed to cure overnight. The fluidic device was connected to a 4294A Agilent Impedance Analyzer (Agilent Technologies, Inc., Santa Clara, CA), with the inlet port connected to a New Era NE1000 microfluidic syringe pump. The fluidic device was deconstructed as needed by extended soaking in dichloromethane for a minimum of three hours.

Electrochemistry:

Cyclic voltammetry studies were conducted with 3 mM $K_3[Fe(CN)_6]$ (aq) in 0.06 M $KNO_3$ (aq). For macroscale electrochemistry using disc electrodes, cyclic voltammetry studies were conducted over a scan rate range of 5 mV/s to 1000 mV/s, within the voltage range of −100 mV to 750 mV for the glassy carbon electrode and −150-600 mV for the gold working electrode. Both disc gold and glassy carbon working electrodes were tested, with an Ag/AgCl (s) reference electrode and a platinum wire counter electrode. For microelectrode electrochemistry, the microelectrodes on the surface of one of the glass slides were utilized as the working and counter electrode in a bulk amount (approximately 50 mL) of solution. Cyclic voltammetry studies were conducted over a range of scan rates (5 mV/s to 1000 mV/s), scanning the voltage range of −150 mV to 600 mV. One electrode was used as a working electrode while testing the other electrodes on the surface as a counter electrode with an Ag/AgCl (s) reference electrode.

Microelectrode drop electrochemistry 300 μL of solution was layered on the single microelectrode slide on the working electrode. Cyclic voltammetry was conducted over a range of scan rates (5 mV/s to 5000 mV/s), scanning the voltage range of −800 mV to 800 mV. These studies utilized platinum wires as counter and reference electrodes respectively. For GAC supported on gold microelectrodes, the studies used same configuration with the only difference being the GAC loaded on the working electrode. A given amount of GAC was layered over the working electrode and compacted using a microscope slide which also removed the excess. This was qualitatively analyzed with a microscope to verify electrode surface coverage.

Randles-Sevcik analysis of electrochemical data: The current response collected was plotted against the scanning voltage. This data can be further analyzed using the Randles-Sevcik equation shown in Equation 1:

$$i_p = 0.4463 nFAC \left(\frac{nFvD}{RT}\right)^{\frac{1}{2}} \quad [1]$$

with $i_p$ being peak current (A), n the number of electrons transferred, A the electrode surface area (cm$^2$), F the Faraday constant (Cmol$^{-1}$), D the diffusion coefficient (cm$^2$/s), v the scan rate (V/s), T temperature (K), R the gas constant (JK$^{-1}$ mol$^{-1}$), and C the concentration (mol/cm$^3$). This equation relates peak current to the square root of scan rate and allows determination of the diffusion coefficient, all other factors being known.

Example 1

Microfluidic Electrochemical Cell

Figure 12:
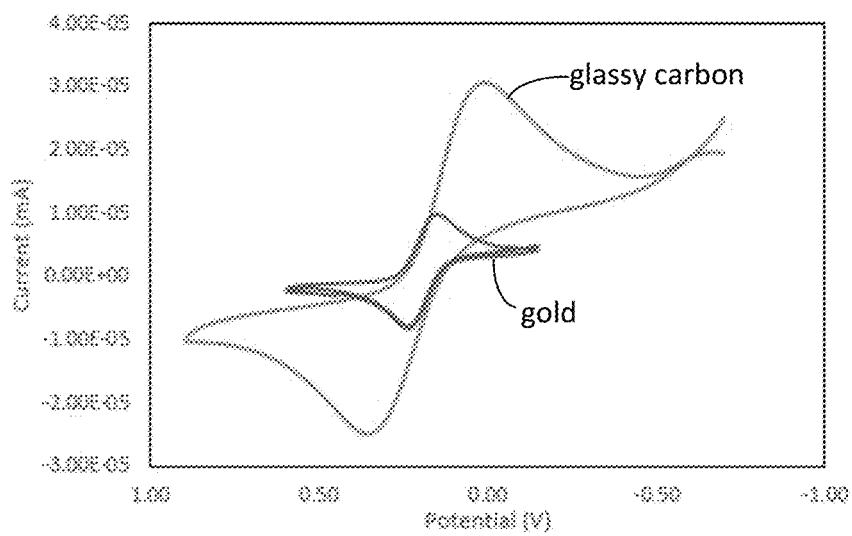
FIG. 12 shows cyclic voltammograms of an aqueous solution of 3 mM $K_3[Fe(CN)_6]$ (aq) in 0.06 M $KNO_3$ (aq) as a function of scan rate, 100 mV/s with a glassy carbon working electrode and a gold working electrode (Pt wire reference electrode and Ag/AgCl reference electrode).
Figure 13:
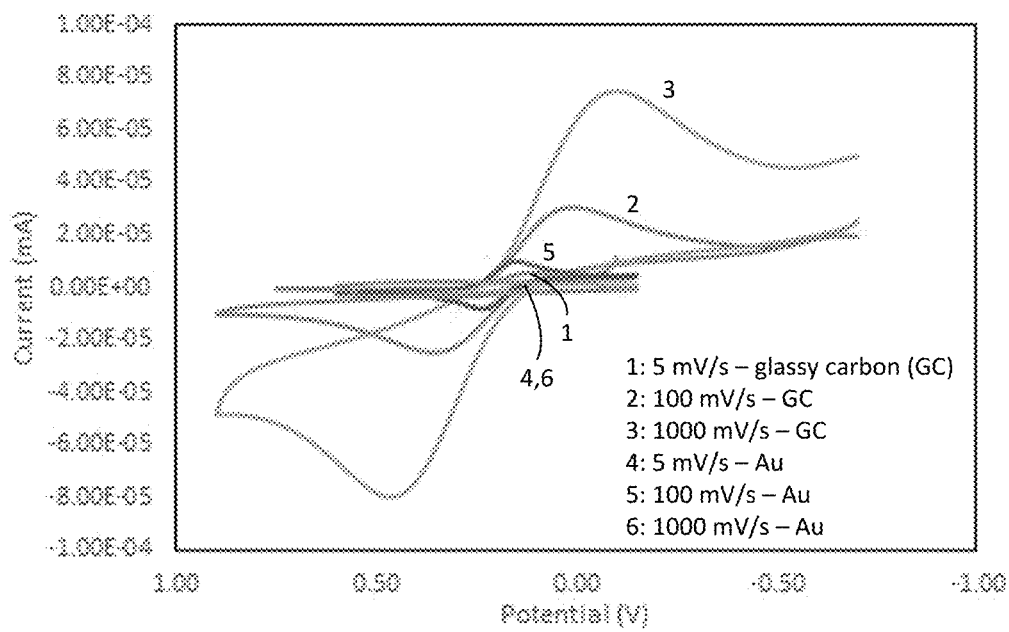
FIG. 13 shows cyclic voltammograms of an aqueous solution of 10 mM $K_3[Fe(CN)_6]$, 0.1 M $KNO_3$ as a function of scan rate (1) 5 mV/s, (2) 100 mV/s, and (3) 1000 mV/s with a (glassy carbon working electrode and (4) 5 mV/s, (5) 100 mV/s), and (6) 1000 mV/s with a gold working electrode (Pt wire reference electrode and Ag/AgCl).

Microelectrodes were prepared on a glass slide as described above, and the performance compared to macro electrodes. For macroelectrode chemistry comparison, cyclic voltammograms of 3 mM $K_3[Fe(CN)_6]$ (aq) in 0.06 M $KNO_3$ (aq) as a function of scan rate were conducted with glassy carbon and gold working electrodes (FIG. 12). The macro electrodes exhibited standard behavior with the glassy carbon working electrode having a greater current response than the gold working electrode, due to the difference in surface area and nature of the working electrode used. At a scan rate of 5 mV/s, the glassy carbon working electrode exhibited an oxidation peak at 0.6V and a reduction peak at 0.33V. Glassy carbon current response is dependent on scan rate. The oxidation peak for gold occurred at 0.16 V and the reduction peak was at 0.21 V. Using the glassy carbon electrode and a scan rate of 5 mV/s, peak separation was greater than the 59 mV expected for an electrochemically reversible redox reaction with an electron transfer stoichiometry of 1; however this was attributed to slow kinetics of heterogeneous electron transfer between the redox probe and the electrode. With increase in scan rate, the peak-to-peak separation increased while it decreased with the decrease in scan rate as is also consistent with the electrode configuration (FIG. 13). With the gold electrode, the peak separation was less than the 59 mV threshold for electrochemically reversible reactions, and this stayed within the 59 mV threshold with an increase in scan rate, which is standard for this electrode configuration.

Figure 14A:
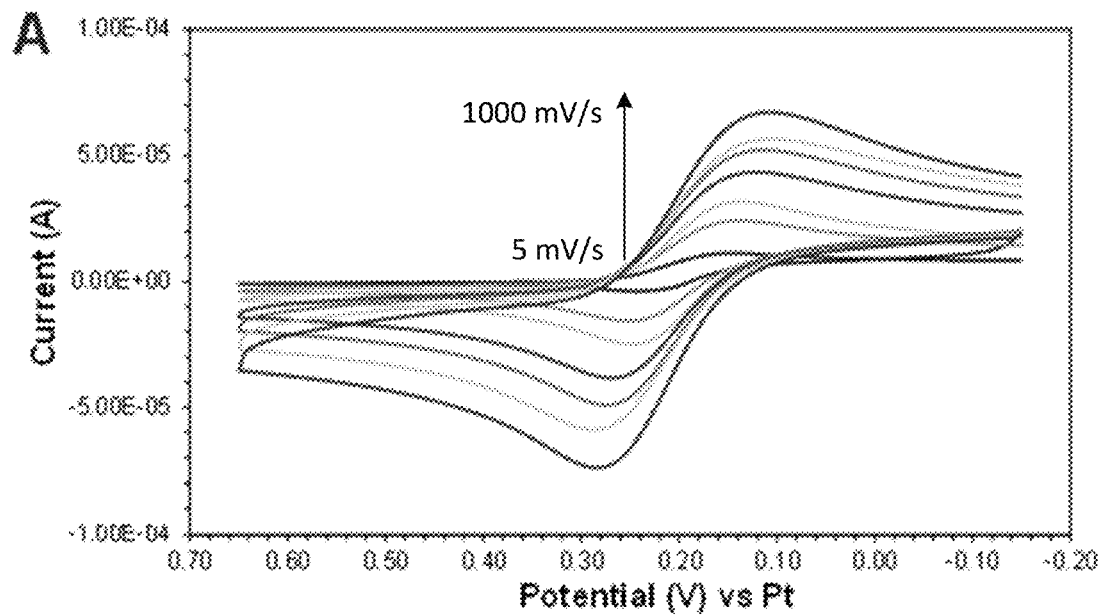
FIGS. 14A-C show cyclic voltammograms of a microelectrode immersed in aqueous solution of 3 mM $K_3[Fe(CN)_6]$, 0.06 M $KNO_3$ as a function of scan rate ranging from 5 mV/s to 1000 mV/s with counter electrodes C1 (14A), C2 (14B), and C3 (14C).
Figure 14B:
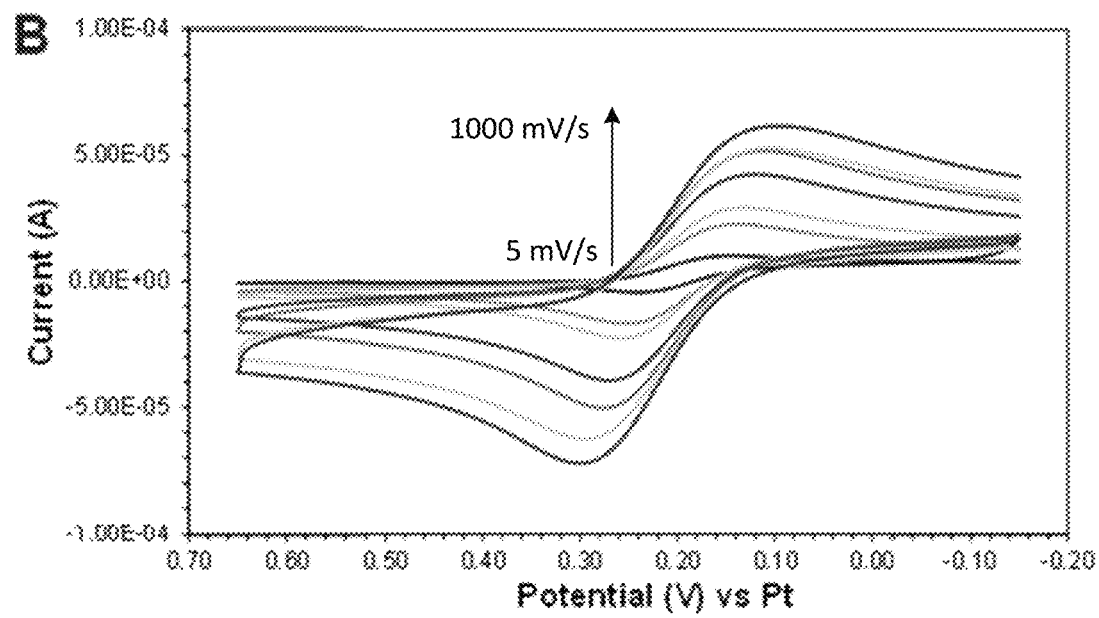
Figure 14C:
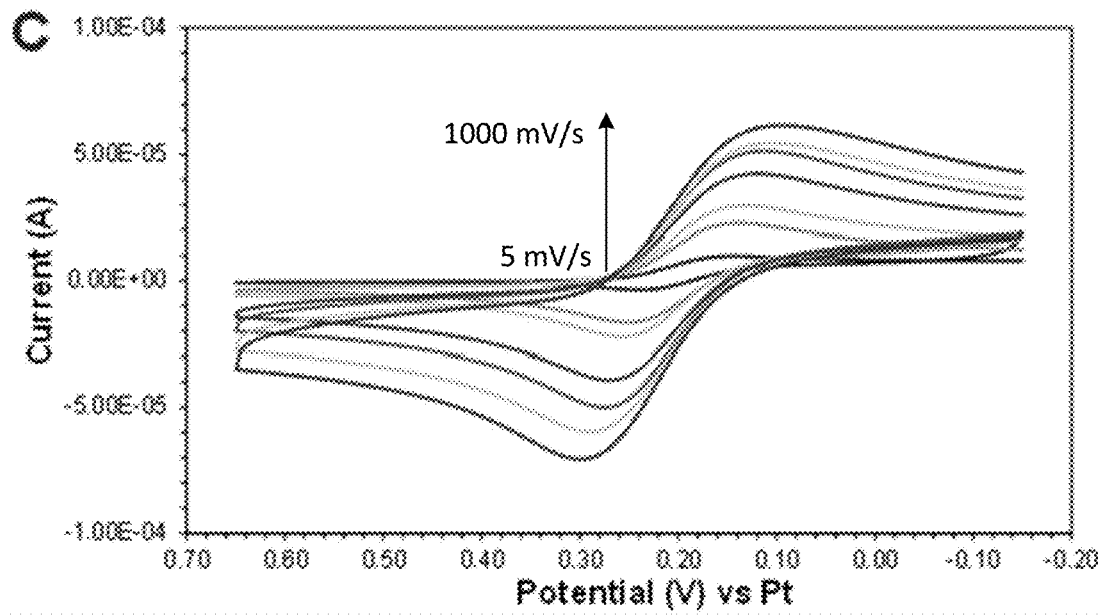
Figure 15:
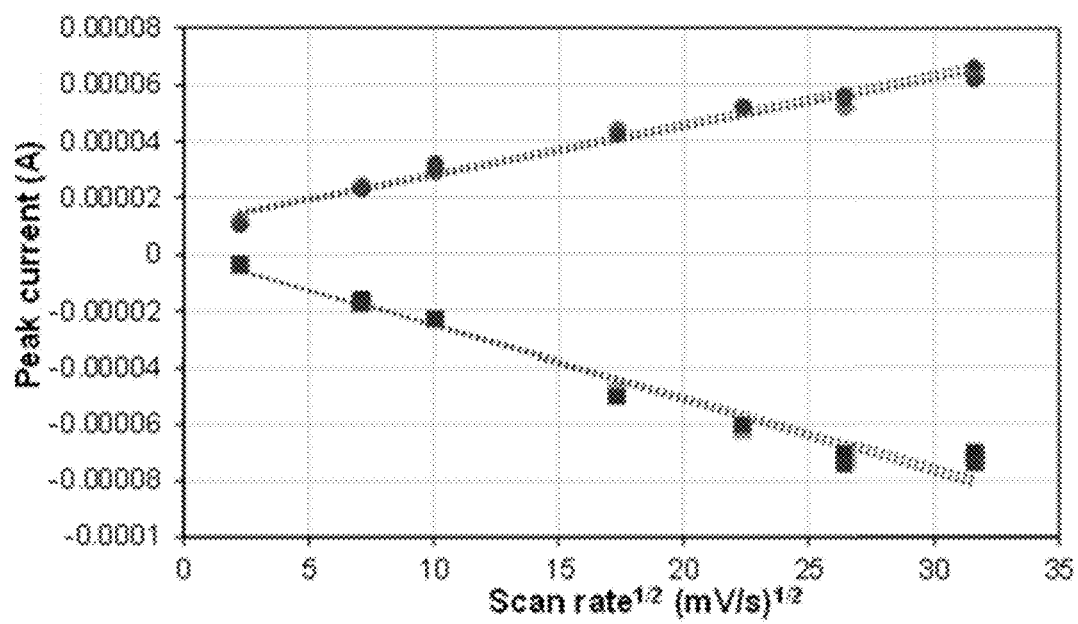
FIG. 15 is a plot of peak current versus the square root of scan rate of the cyclic voltammograms of FIGS. 14A-14C where circles represent the cathodic trace and squares represent the anodic trace.

For comparison of the macroelectrode system to the microelectrode system, cyclic voltammograms of 3 mM $K_3[Fe(CN)_6]$ (aq) in 0.06 M $KNO_3$ (aq) as a function of scan rate were conducted with the microelectrodes as the working and counter electrodes (FIGS. 14A-14C). The position of the oxidation and reduction peaks potentials were observed to remain almost unchanged irrespective of the counter electrode C1, C2, or C3. At a scan rate of 5 mV/s, the oxidation and reduction peaks occurred at 0.17 V and 0.23 V respectively (Li peak to peak separation=0.6 V) which is consistent with an electrochemically reversible redox reaction with an electron transfer stoichiometry of 1. With increasing scan rate, progressive increases in respective peak currents and peak separation were observed, consistent with the literature. Plots of the respective peak currents versus the square root of scan rates are almost identical as shown in FIG. 15. The linearity of current response with square-root of scan rate indicated chemical reversibility (FIG. 15). At a scan rate of 5 mV/s, the oxidation and reduction peaks occur at 0.17 V and 0.24 V respectively (peak to peak separation, $\Delta Ep=0.071$ V) which is consistent with an electrochemically reversible redox reaction with an electron transfer stoichiometry of 1. The peak-to-peak separation matches to that observed (0.059 V) on a regular three electrode set-up using a gold-disc working electrode and a Pt counter electrode using the same Pt wire as a quasi-reference. The linearity of current response with square root of scan rate is consistent with Randles Sevcik behavior.

Figure 16:
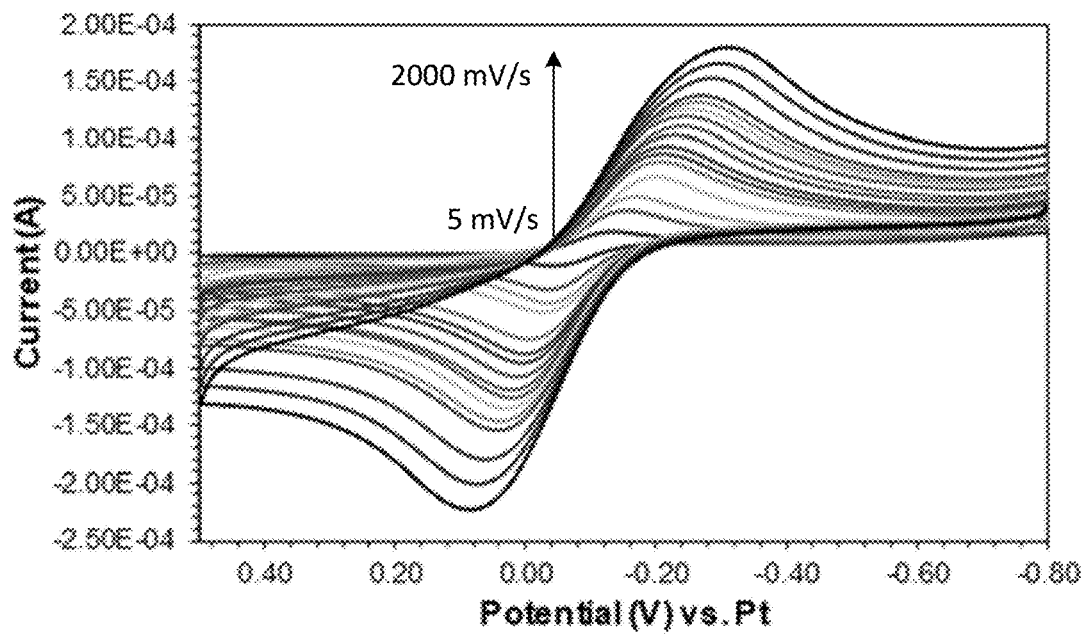
FIG. 16 shows cyclic voltammograms of a drop of aqueous solution of 3 mM $K_3[Fe(CN)_6]$, 0.06 M $KNO_3$ as a function of scan rate from 5 mV/s to 1000 mV/s.
Figure 17:
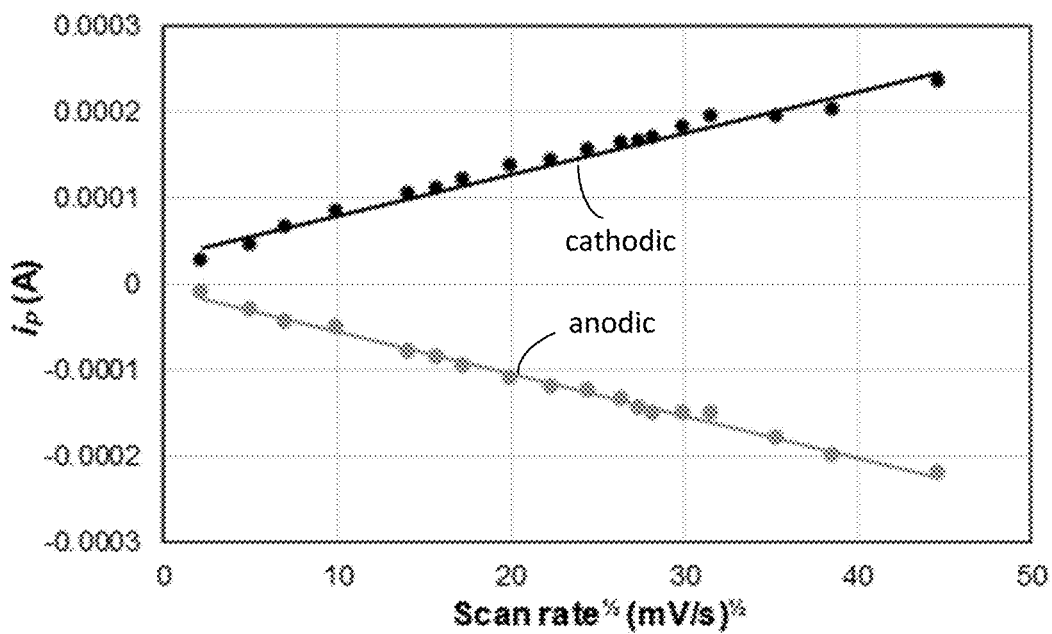
FIG. 17 is a plot of peak current versus the square root of scan rate of the cyclic voltammograms of FIG. 16.

Cyclic voltammograms of a 300 μL drop of 3 mM $K_3[Fe(CN)_6]$ (aq) in 0.06 M $KNO_3$ (aq) as a function of scan rate from 5 to 2000 mV/s were conducted with the working microelectrode (FIG. 16). Platinum wires were the counter and reference electrodes. At a scan rate of 5 mV s$^{-1}$, the voltammogram exhibits an oxidation peak at −0.046 V and a reduction peak at −0.120 V, with a peak-to peak separation ($\Delta Ep$)=0.074 V. A progressively increase in $\Delta Ep$ is observed upon increasing the scan rate suggesting a semi-infinite linear diffusion behavior. Even though with increasing scan rates, the $E_{pa}$ was observed to move to more positive values and the $E_{pc}$ was observed to move to more negative values, the shift in the $E_{pc}$s is of greater magnitude (v, $E_{pa}$, $E_{pc}$: 5 mV s$^{-1}$, −0.046 V, −0.120 V; 50 mV s$^{-1}$, −0.038 V, −0.180 V; 500 mV s$^{-1}$, 0.020 V, −0.250 V; 2000 mV s$^{-1}$, 0.076 V, −0.320 V), suggesting the shift of $E^{0'}$. This is due to the change in concentration of the oxidative and reductive species with respect to the Pt quasi reference electrode The linearity of current response with square-root of scan rate indicated chemical reversibility (FIG. 17).

Figure 18:
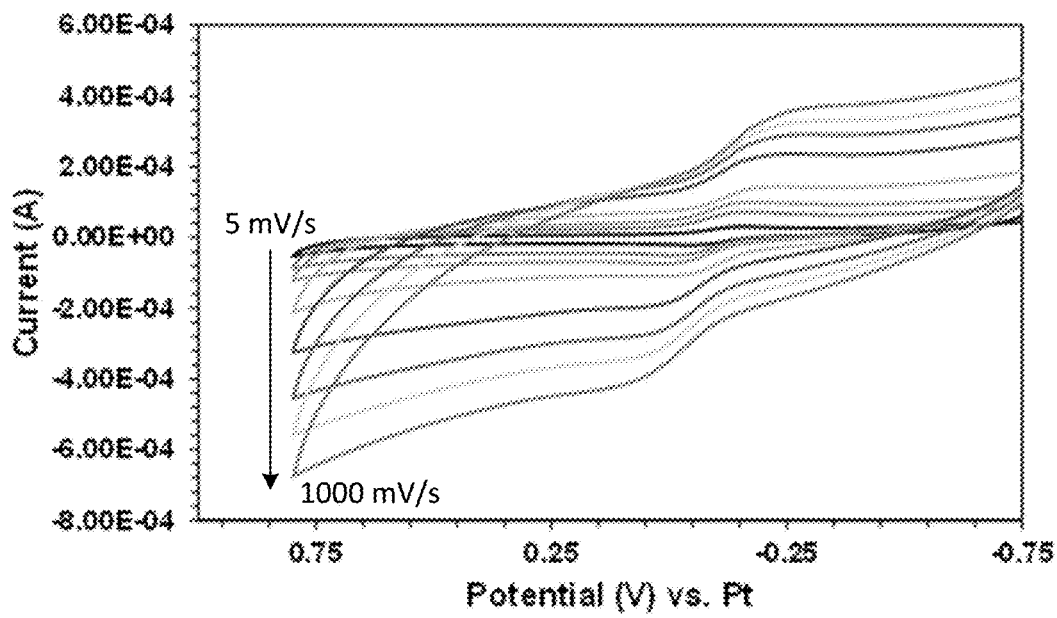
FIG. 18 shows cyclic voltammograms of a drop of aqueous solution of 3 mM $K_3[Fe(CN)_6]$, 0.06 M $KNO_3$ as a function of scan rate from 5 mV/s to 1000 mV/s (working gold microelectrode with GAC, Pt wire reference electrode, and Pt wire auxiliary electrode).
Figure 19:
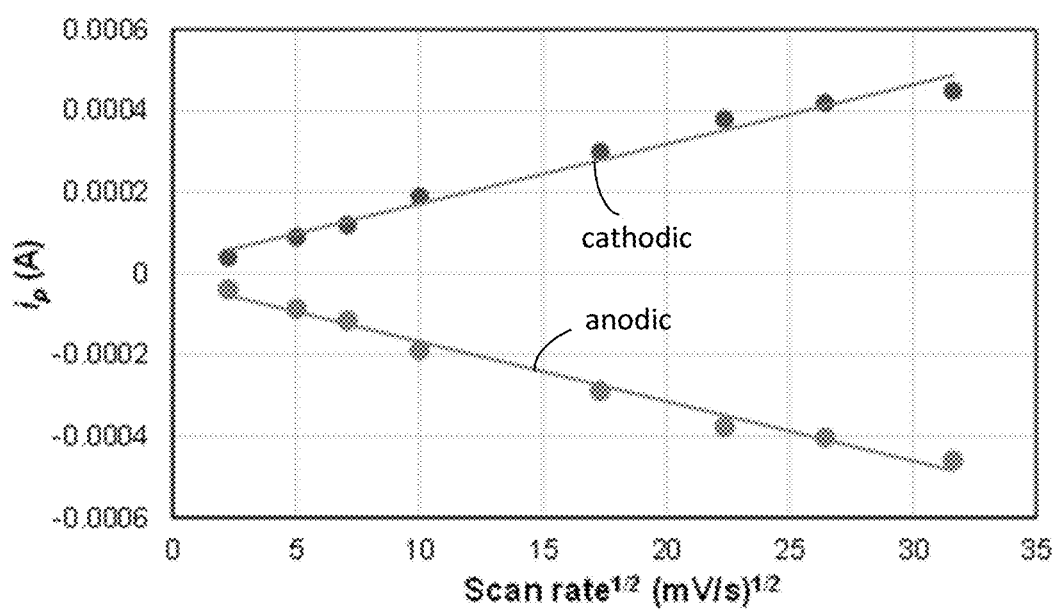
FIG. 19 is a plot of peak current versus the square root of scan rate of the cyclic voltammograms of FIG. 18.

To study the effect of changing the working electrode, a set of replicate studies were performed where a small measured amount of GAC was layered over the working electrode as described in the experimental section, to act as the working electrode. The voltammograms with this GAC working electrode are shown in FIG. 18. At a scan rate of 5 mV/s, the oxidation and reduction peaks are −0.14 V and −0.08 V respectively. The peak separation indicated chemical reversibility, which was expected. Considering a larger range of scan rates, with increased scan rate increased peak response and peak separation were observed. Linearity of peak current against the square root of scan rate revealed a 1:1 cathodic peak current to anodic peak current which indicated chemical reversibility (FIG. 19).

Initial studies implementing a flow rate ranging from 1 µL/min to 0.75 mL/min within the microfluidic channel posed difficulty because flow rates ≥5 µL/min were too high and experimentally damaged the seal between the two electrode surfaces. This made the solution flow seep through the sides of the microelectrode configuration. Flow rates were adjusted accordingly for later studies, testing both 1 µL/min and 2 µL/min in consequent studies.

The results demonstrated reproducibility in the use of a microfluidic microelectrode device, suggesting feasibility in further development of a sensor with field deployment capabilities. The cyclic voltammetry studies allowed for the determination of the diffusion coefficient and with the testing of the bare microfluidic electrode, allowed for the determination of the electrode size which allows for further investigation utilizing more complex instrumentation. Randle-Sevcik analysis showed a 1:1 ratio between anodic and cathodic peak-currents suggesting electrochemical behavior in the microelectrode set up comparable with macroelectrode systems.

Example 2

Preparation of Cr-MIL-101 and Fe-MIL-101 and Characterization, of their Interactions with PFOS Cr-MIL-101 was synthesized under hydrothermal conditions as previously reported in the literature (Guo et al., *Angew Chem Int Edit* 2018, 57(18):4926-4930). Briefly, in a Parr reactor liner, chromium(III) nitrate nonahydrate (Cr(NO$_3$)$_3$·9H$_2$O, 3.36 g) and terephthalic acid (BDC, 1.39 g) were added to distilled water (40 mL) and stirred vigorously for 30 min. The liner was sealed in the vessel and placed in an oven at 200° C. for 24 h. After cooling to room temperature, the as-synthesized product was centrifuged and washed with water (3×30 mL). To isolate the MOF, the filtered product was washed with N,N-dimethylformamide (3×30 mL) repeatedly over the course of 24 h. Finally, the solvent was exchanged with methanol (3×30 mL) over the course of another 24 h. The product was dried in a vacuum oven at 70° C. overnight and activated at 150° C. for 24 h prior to characterization.

Fe-MIL-101 was synthesized similarly to that previously reported in the literature (Tang et al., *New J. Chem.* 2015, 39:4919-4923). Briefly, in a Parr reactor liner, iron (III) chloride hexahydrate (FeCl$_3$·6H$_2$O, 4 mmol), terephthalic acid (BDC, 4 mmol), and acetic acid (2 mL) were added to N,N-dimethylformamide (50 mL) and stirred vigorously for 30 min. The liner was sealed in the vessel and placed in an oven at 120° C. for 24 h. After cooling to room temperature, the as-synthesized product was centrifuged and washed with N,N-dimethylformamide (3×30 mL). Finally, the solvent was exchanged with methanol (3×30 mL) over the course of another 24 h. The product was dried in a vacuum oven at 70° C. overnight and activated at 150° C. for 24 h prior to characterization.

Concentrated PFOS was diluted in DI water to concentrations of 100, 50, 10, and 1 mM solutions. Preliminary tests with $^{19}$F NMR revealed that the time scale for full sorption using 1 mM solutions was on the order of seconds, while for 100 mM solutions, it was on the order of days.

The pre-synthesized and activated (at 150° C. for 24 h under vacuum) Cr-MIL-101 and Fe-MIL-101 were soaked in an aqueous solution of PFOS (10 mM) under stirring for 24 h. The mixture was allowed to soak for another 24 h without stirring. Finally, the water was removed by heating the solution to 100° C. in a convection oven for 24 h. Once dried, the recovered product was rinsed with fresh DI water and allowed to dry in air. Prior to characterization, the sample was activated under vacuum at 150° C. for 24 h.

To characterize any morphological changes in Cr-MIL-101 upon PFOS exposure as well as to evaluate the microscopic disposition of PFOS onto the Cr-MIL-101 framework, transmission electron microscopy (TEM) was conducted on the MOF samples prior to and post PFOS exposure. The diffraction patterns of the materials prior to PFOS exposure can be indexed in the Fd$\bar{3}$m space group. The electron micrograph of FIG. 20A shows well defined crystals of Cr-MIL-101 whose shape, geometry and morphology remain nearly unaltered upon PFOS exposure (FIG. 20B). The dimensions of the crystals in the unaltered Cr-MIL-101 samples also remain unchanged, and the cubic symmetry of the crystals, as reflected in the shape of the crystals, are also preserved after PFOS exposure indicating the robust nature of these materials. Elemental mapping shows that post-exposure, the F distribution on the crystals nearly shadows the Cr elemental map, indicating affinity of PFOS for the Cr-MIL-101 material (FIGS. 20C-20E).

The structural integrity of the bulk samples post PFOS exposure were further characterized using powder X-ray diffraction (PXRD) measurements as shown in FIG. 21. The PXRD pattern of the Cr-MIL-101 sample post PFOS exposure showed no peak changes/shifts compared to the parent material prior to exposure clearly indicating no structural alteration of the framework upon adsorption.

Figure 22A:
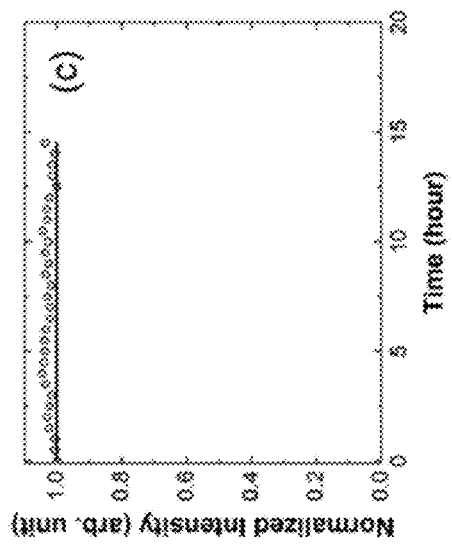
FIGS. 22A-22C show normalized intensities (area) of the $^{19}F$ NMR peak centered at −79 ppm (O) tracked over time upon addition of 800 μL of 10 mM $PFOS/H_2O$ to Cr-MIL-101 (8.6 mg, 22A), Fe-MIL-101 (8.2 mg, 22B), and granular activated carbon (9.4 mg, 22C). Circles represent collected data while lines represent fitted curves. Insets show data and corresponding fits for the first 40 h of data collection.
Figure 22B:
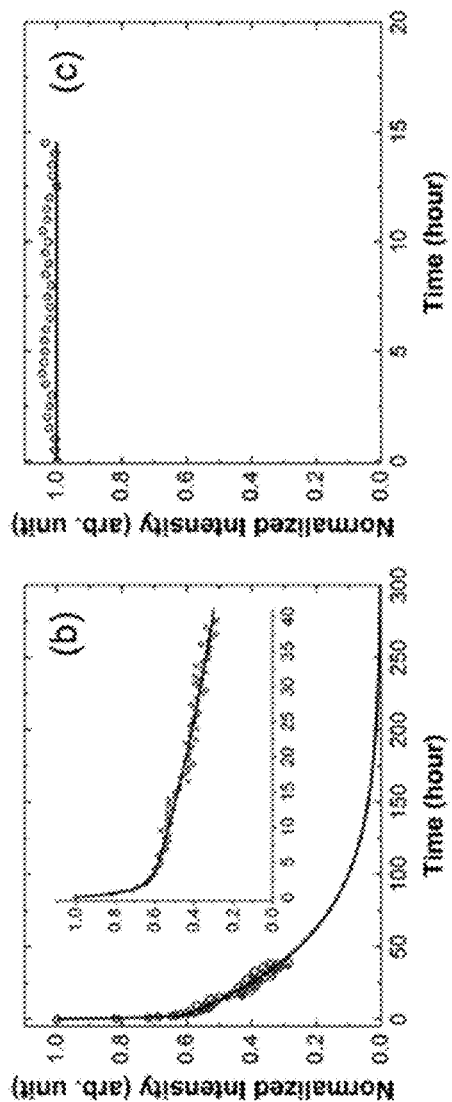
Figure 22C:
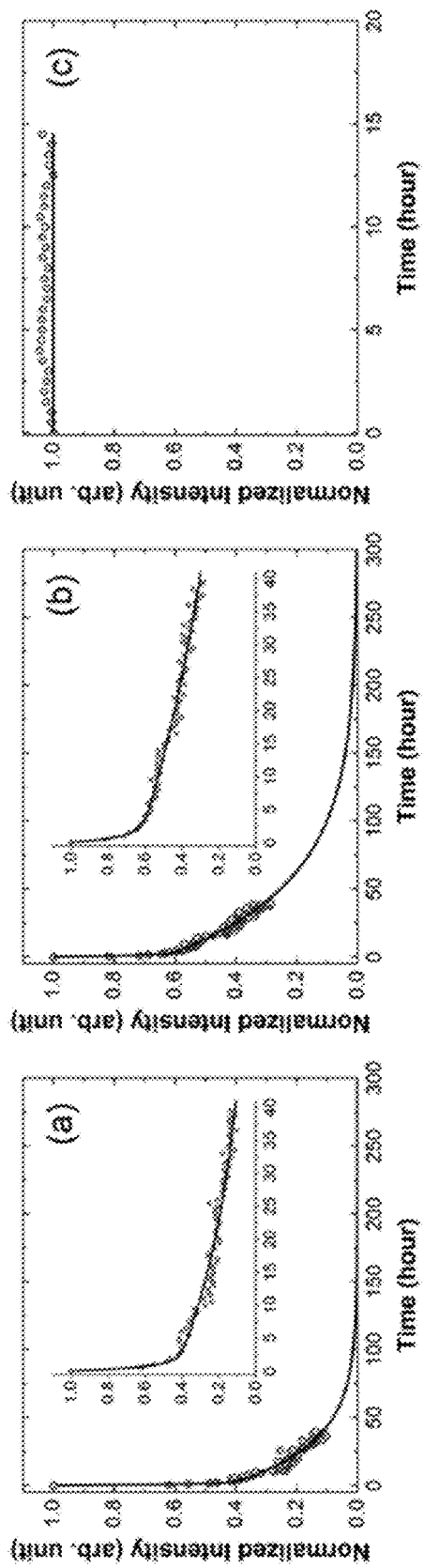

Liquid-state $^{19}$F NMR measurements were performed on a 10 mM PFOS solution (~1 mL) before, during, or after contact with ~10 mg of sorbent material. Experiments were conducted using a 750 MHz NMR spectrometer (Agilent, USA) with a 5 mm wideband HXY probe at room temperature as a function of time and continued up to ~40 h with the time interval of 30 min. $^{19}$F NMR spectra were accumulated on the Larmor frequency of 705.83 MHz using a single pulse excitation. The solid-state $^{19}$F NMR was performed on the material that was exposed to PFOS solution in the $^{19}$F solution NMR experiments; the solids were separated and dried in a convection oven at 120° C. for 24 h. The spectra were accumulated with a 4 mm HFXY magic angle spinning (MAS) probe on a 600 MHz solid-state NMR spectrometer (Agilent, USA) on the Larmor frequency of 564.68 MHz using a spin-echo sequence at spinning speed of 14 kHz. The $^{19}$F chemical shift for both liquid- and solid-state experiments was calibrated against pure CF$_3$CH$_2$OH (−78 ppm as external reference. For the samples containing PFOS, the resonance at −79 ppm, which showed baseline and high intensity as compared to other fluorine resonances, was utilized to measure sorption kinetics. As shown in FIGS. 22A-22C, there is clearly a decay of the mobile, bulk phase PFOS concentrations in the solutions in contact with either Cr-MIL-101 (22A) or Fe-MIL-101 (22B) due to their sorption and immobilization. Closer analysis of the data shows that the peak intensity decreases rapidly in the early stage (within 2 h) of sorption and plateaus after longer sorption times (~40 h). To quantify and distinguish the performance between the materials, the sorption profiles were fitted to a double exponential decay function. It is clear from FIGS. 22A-22B and the fitted time constants that Cr-MIL-101 adsorbs PFOS ~2 times faster than Fe-MIL-101. An extrapolation of the fitted curves shows that maximum removal of PFOS from the bulk phase supernatant solution can be estimated to take nearly 250 h for Fe-MIL-101 while it takes only ~125 h for Cr-MIL-101. Also Cr-MIL-101 is observed to be superior to Fe-MIL-101 in the sorption of PFOS at the early stage of sorption. Similarly, as a control, GAC was also probed for PFOS sorption using liquid state $^{19}$F NMR, and the signal intensities were tracked over time. Surprisingly, at this concentration, the intensity of the resonance at −79 ppm was observed to stay largely invariant in the course of ~15 h as shown in FIG. 22C indicating little or no change in the bulk phase PFOS concentration in contact with GAC.

Figures 23A, 23B:
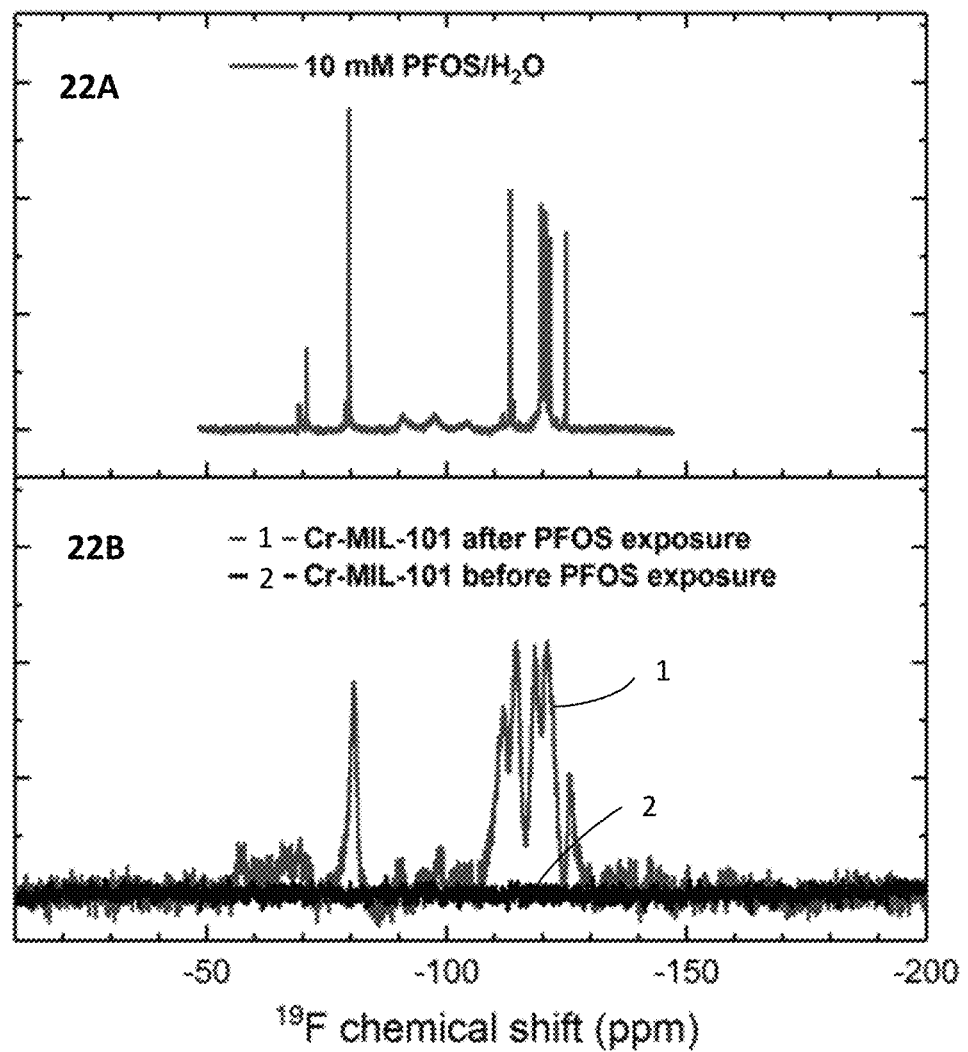
FIGS. 23A-23B show $^{19}F$ liquid state NMR for 10 mM PFOS in $H_2O$ (23A) and $^{19}F$ solid state NMR for Cr-MIL-101 before and after exposure to PFOS (23B).

To directly confirm the presence of PFOS on the MOFs, $^{19}$F solid-state NMR spectrum were also collected on the PFOS exposed Cr-MIL-101 sample as shown in FIGS. 23A-23B. Even after flushing the powder sample with DI water to remove any bulk phase concentrations, a clear $^{19}$F signal that was not present in the Cr-MIL-101 sample prior to exposure could be observed. The resemblance of this solid state $^{19}$F-NMR spectrum of PFOS-exposed Cr-MIL-101 (FIG. 23B) with the solution $^{19}$F-NMR spectrum of PFOS in DI water (FIG. 23A) validates its capture by Cr-MIL-101.

Figure 24A:
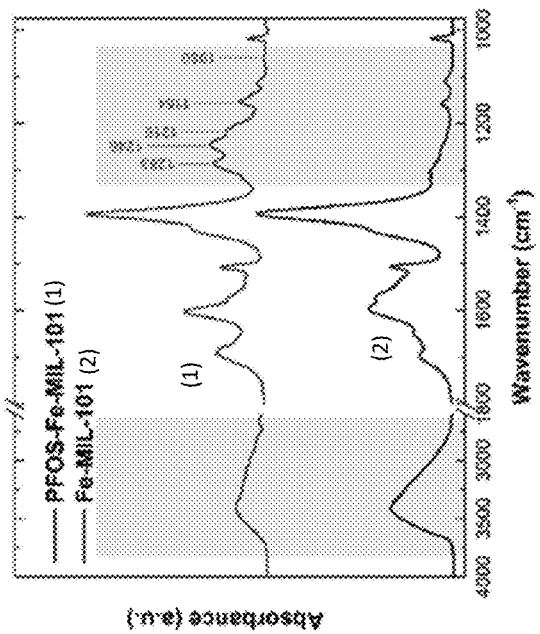
FIGS. 24A-24B show infrared spectra of Cr-MIL-101 (24A) and Fe-MIL-101 (24B) before and after exposure to 10 mM PFOS (after drying).
Figure 24B:
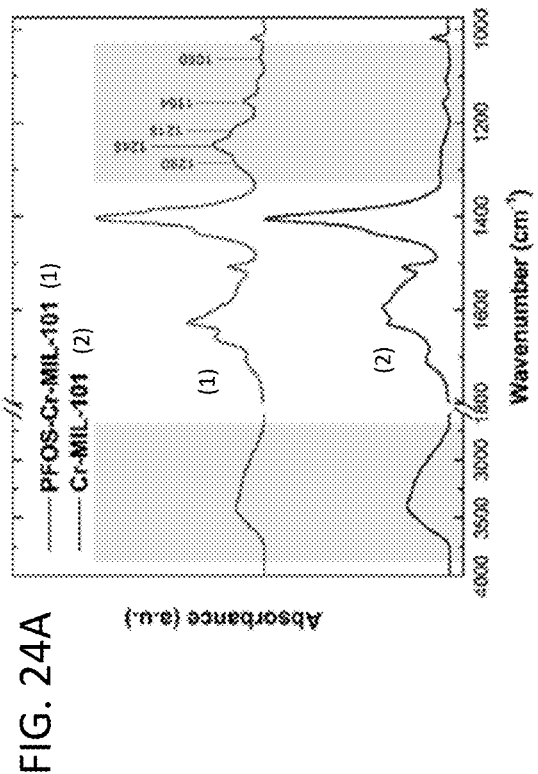

To probe changes in the sorbent structure after sorption via vibrational frequencies and verify the presence of PFOS in the MOF frameworks, infrared spectroscopy was also utilized. The transmission IR spectra of pristine MOFs as well as MOFs post PFOS exposure are shown in FIGS. 24A-24B. Bands in three separate regions were considered, i.e., i.e., 3600-3000 cm$^{-1}$ for —OH vibration, 1700-1300 cm$^{-1}$ for the assignments from aromatic ring or carboxylate of the pristine MIL-101 MOFs, and 1300-1050 cm$^{-1}$ for the functional groups from the PFOS. The most striking difference for the pristine MOFs and MOFs PFOS exposure, which are assigned to the —CF$_2$, —CF$_3$, or SO$_3^-$ functional groups respectively. These peaks are slightly shifted compared to those previously reported. This might be due to the confinement of PFOS molecules within the pores of these MOFs. The intensity of the broad band at 3600-3000 cm$^{-1}$ was clearly decreased with the addition of PFOS. This band is formed by the —OH stretching of H$_2$O molecules stabilize din the MOF pores via hydrogen bond. It further supports that PFOS is loaded into the MIL-101 cages. Also, bands in the region of 1700-1300 cm$^{-1}$, assigned to the —C=C or —OCO groups from the pristine MIL-101 were largely retained after PFOS sorption, indicating a stable MOF structure.

Figure 25A:
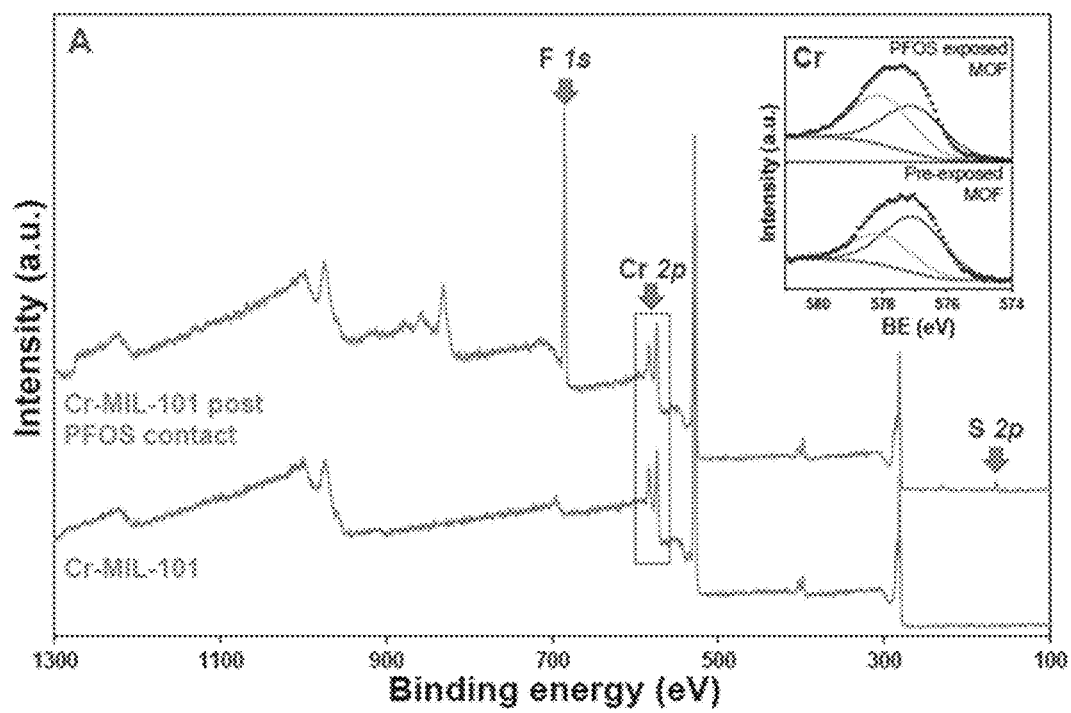
FIGS. 25A and 25B are X-ray photoelectron spectra showing (i) Cr-MIL-101 pre- and post-exposure to PFOS (25A), and (ii) PFOS as received and sorbed onto Cr-MIL-101 (25B). The inset of FIG. 25A shows the Cr $3p_{3/2}$ region pre and post PFOS exposure. The left inset of FIG. 25B shows the F1s region of pristine PFOS and post-immobilization on Cr-MIL-101. The right inset of FIG. 25B shows the S 3p region of pristine PFOS and post-immobilization on Cr-MIL-101. Symbols in the insets represent experimental spectra, and solid lines show the spectral fits.
Figure 25B:
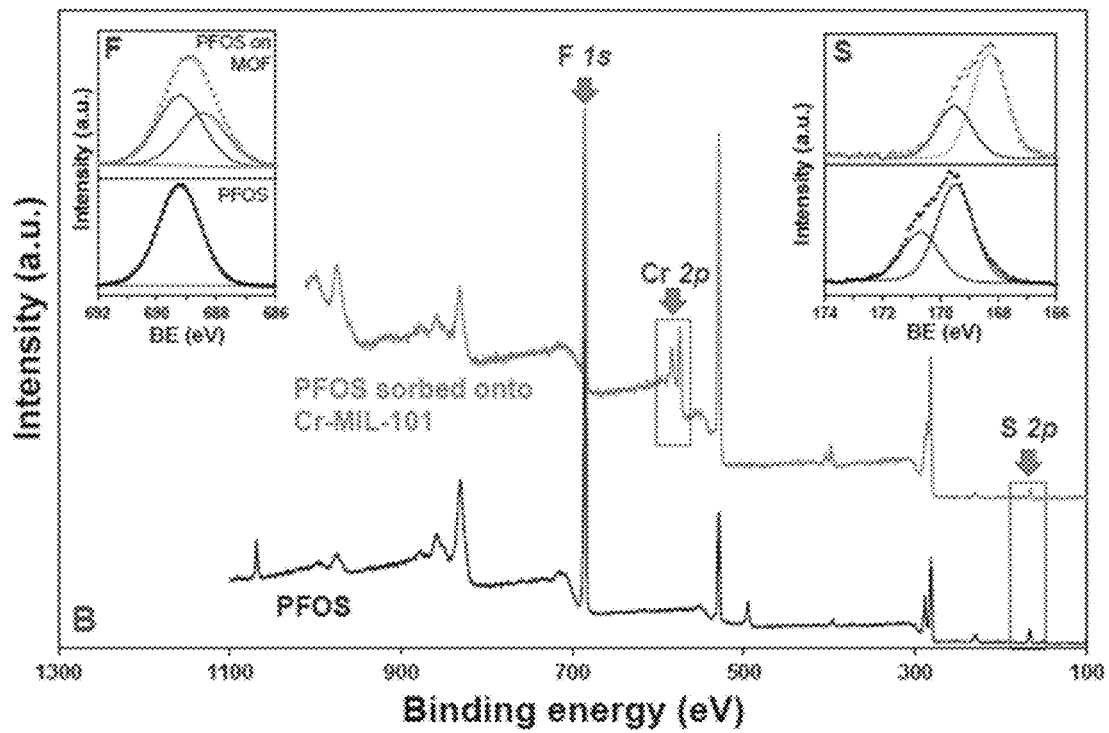

Having confirmed the sorption of PFOS, the specificity of the host-guest interaction was evaluated to gain further insight into receptor affinity. X-ray photoelectron spectroscopy (XPS) was conducted on the materials pre and post PFOS exposure to interrogate changes in electron density of the key elements involved in the capture process that can throw light on element specific affinities (FIGS. 25A-25B). As seen in FIGS. 25A-25B, the full photoelectron profile of the as received Cr-MIL-101 materials post PFOS exposure showed clear evidence of capture of PFOS from the appearance of F and S bands in the exposed material. A closer inspection of the data and comparison with the spectrum of pure Cr-MIL-101 as well as pure PFOS provides some key conclusions. Firstly, the Cr region of the photoelectron spectrum of the as received Cr-MIL-101 sample (inset of FIG. 23A) showed two Cr environments as demonstrated by the Cr2p3/2 region being resolved into two species with binding energy values of 577.1 eV and 578.2 eV respectively, with the lower oxidation state being the dominant contributor (ratio=4:3). Exposure to PFOS resulted in the higher oxidation state gaining in intensity at the expense of the lower oxidation state (ratio=1:2), suggesting oxidation of the Cr center upon contact with PFOS. Specifically, as Cr-MIL-101 is present in large excess compared to the PFOS, it is significant to observe any discernible shift at all in the binding energies of the Cr metal center of the host framework, and indicates a strong, favorable sorbent-sorbate interaction. The F region of the spectrum showed a consistent opposite shift; compared to the spectrum of the as-received PFOS which showed a single 1s line at 689.3 eV, the spectrum of PFOS sorbed onto Cr-MIL-101 showed an additional second F environment with lower binding energy of 688.5 eV suggesting it gaining in electron density (left inset of FIG. 15B). This is suggestive of a synergistic redox process with the F atoms pulling electrons away from the soft Cr center, and thereby getting reduced. This was supported by computational molecular simulation studies between Cr-MIL-101 and a fluorocarbon, the computed radial distribution functions (RDFs) between partially positively charged framework Cr atoms and partially negative charged F of a fluorocarbon indicated a strong favorable binding Cr⋯F interaction. Interestingly, the S region of the photoelectron spectrum also showed a shift in the same direction as the F spectrum, albeit with significantly larger magnitude. The S2p$_{3/2}$ line shifted from 169.5 eV in the pure PFOS sample to 168.3 eV when PFOS was sorbed onto Cr-MIL-101, suggesting a reduced S oxidation environment in the sorbed sample compared to pure PFOS (right inset of FIG. 23B). The large magnitude of this shift indicates a strong affinity between the Cr and the S, and may be an indication of the strength of interaction between the MOF framework and the polar, sulfonate head of the PFOS molecule. The results suggest that although the nonpolar CF$_3$ groups that make up the tail of sorbate have a clear interaction with the framework, it is in fact the sulfonate moiety that has a stronger affinity for Cr-MIL-101; a combination of these two can in fact lead to highly selective PFOS affinity for Cr-MIL-101. This result can be explained by the relatively high concentrations of PFOS (past the critical micelle concentration) used in this study, which may orient the polar sulfonate head groups towards the potential sorption sites of the sorbent.

Figure 26:
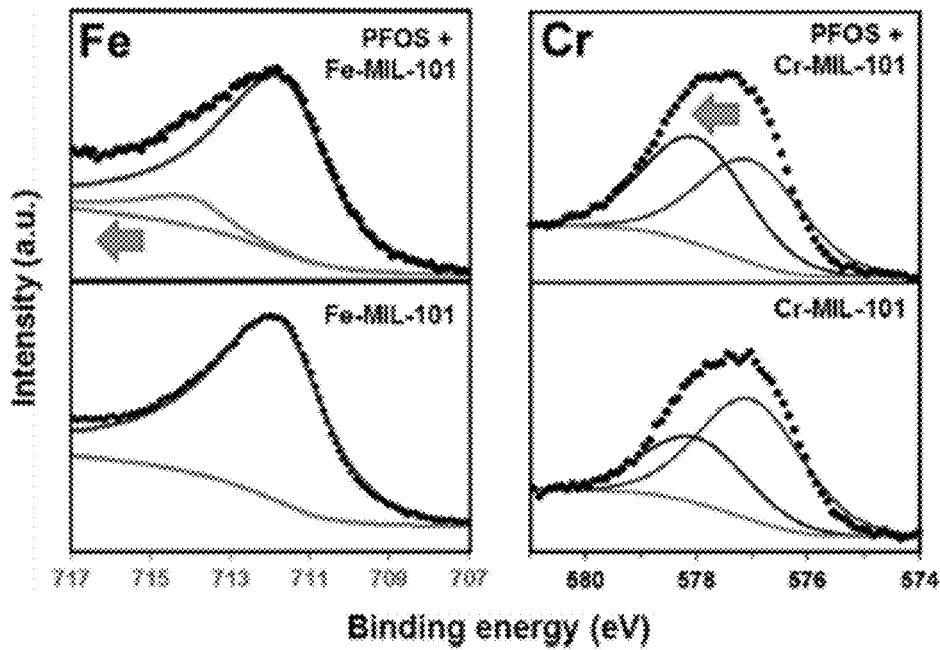
FIG. 26 is X-ray photoelectron spectra showing changes in binding energies (arrows) of the metal node of the MOF framework for both Fe-MIL-101 (left) and Cr-MIL-101 (right) before and after PFOS exposure. For simplicity, only Fe $2p_{3/2}$ and Cr $2p_{3/2}$ portions of the spectra are shown.

FIG. 26 shows X-ray photoelectron spectra for both Fe-MIL-101 (left) and Cr-MIL-101 (right) before and after PFOS exposure. For simplicity, only Fe 2p$_{3/2}$ and Cr 2p$_{3/2}$ portions of the spectra are shown. For Cr-MIL-101, the Cr region of the photoelectron spectrum of the pristine sample showed two Cr environments as demonstrated by the Cr 2p$_{3/2}$ region being resolved into two species with binding energy values of 577.1 and 578.2 eV respectively, with the lower oxidation state being the dominant contributor. MOF exposure to PFOS resulted in the higher Cr oxidation state gaining in intensity at the expense of the lower oxidation state, suggesting chromium oxidation in the presence of PFOS. It should be noted that a detectable change in the Cr binding energies upon sorption is in itself quite significant since the relative abundance of Cr from the MOF framework compared to PFOS molecules adsorbed is so large. This alone suggests strong sorption affinities of PFOS on the MOF. For Fe-MIL-101, the magnitude of this change, as compared to Cr, was smaller. The Fe was observed to get oxidized, with the binding energy maxima of the Fe $2p_{3/2}$ line changing from 711.8 eV in the pre-exposed sample to 712.1 eV in the sample post PFOS exposure. Compared to Cr-MIL-101, based on metal node binding energies alone, the affinities for PFOS on Fe-MIL-101 were seemingly less.

Figure 27:
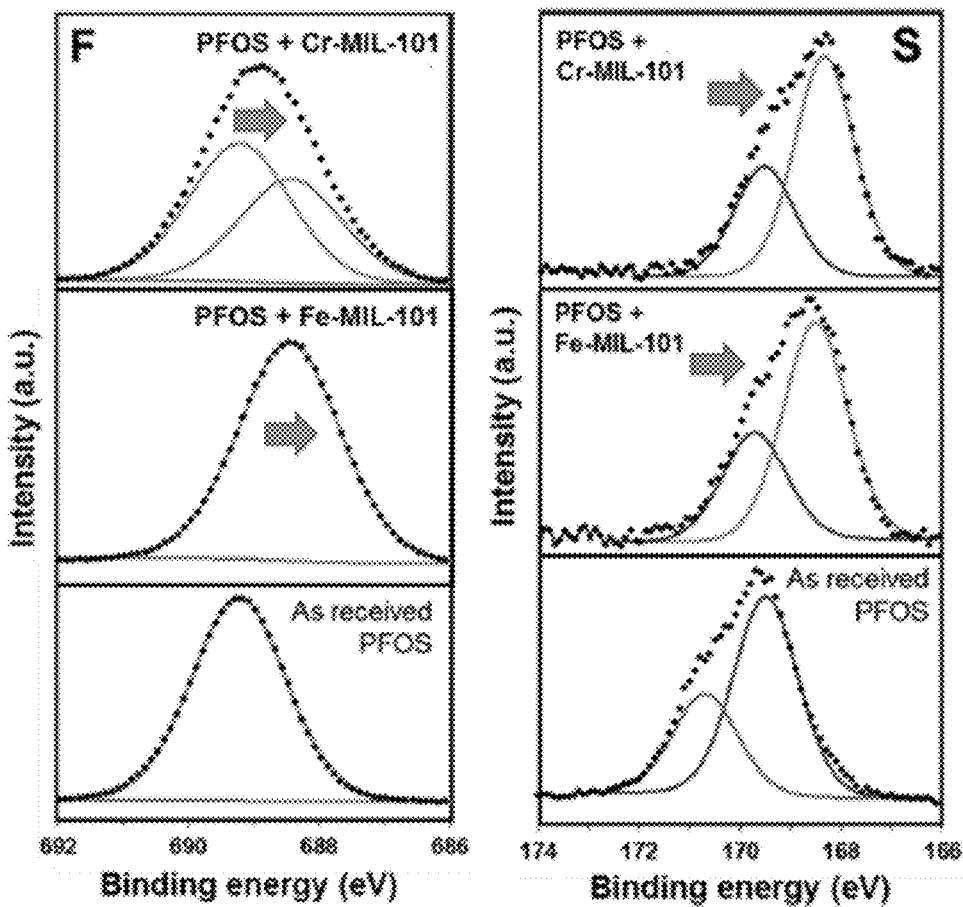
FIG. 27 is X-ray photoelectron spectra showing changes in binding energies (arrows) of the fluorine atoms (F 1s) from the hydrophobic tail and the sulfur atom (S 2p) from the polar headgroup for both Cr-MIL-101 and Fe-MIL-101 before and after PFOS exposure.

Accordingly, the F region of the XPS spectra of PFOS-loaded MOFs showed an opposite shift as expected (FIG. 27). The F of PFOS showed a single 1s line at 689.3 eV, while the spectrum of PFOS sorbed onto Cr-MIL-101 showed an additional second F environment with lower binding energy of 688.5 eV suggesting the F center gaining electron density. Interestingly, a similar, yet more pronounced reduction of the F atoms was observed for Fe-MIL-101. In both cases, this reduction is suggestive of a synergistic redox process with the F atoms pulling electrons away from the metal center and thereby getting reduced. On the basis of the fluorine spectrum alone, PFOS-exposed-Fe-MIL-101 has a more reduced F environment, suggesting stronger interactions with the fluorinated hydrophobic tail compared to those with Cr-MIL-101. Ultimately, the S region of the photoelectron spectrum must be probed since high concentrations of PFOS (past the CMC) are expected to have more sulfur-containing moieties exposed to sorption sites. This S 2p region of the spectrum showed a similar shift in the same direction as the F 1s spectrum, albeit the magnitude of the shift was significantly larger (FIG. 27). This observation confirmed the expectation that the sulfur containing head groups would be forced to interact more with sorption sites of the MOF frameworks compared with the hydrophobic tails. The $2p_{3/2}$ sulfur line shifted from 169.5 eV in the PFOS sample to 168.3 eV in the PFOS-sorbed Cr-MIL-101 sample and to 168.8 eV in the PFOS-sorbed Fe-MIL-101 sample. This clear shift is indicative of a significantly reduced S environment after sorption compared to free PFOS. This also suggests a slightly stronger interaction with Cr-MIL-101 compared to Fe-MIL-101. Overall, considering the full photoelectron spectrum shift before and after PFOS exposure, it is speculated that given (1) the larger observed reduction in S environment, (2) the known enhanced exposure of sulfur moieties due to concentrations higher than the CMC and (3) increased observed oxidation in framework metal centers, and (4) the stronger Lewis acid sites that Cr-MIL-101 likely has a more favorable interaction with PFOS under these experimental conditions. It should also be noted that the structural integrity and morphology of Cr-MIL-101 before and after PFOS exposure was intact as shown by PXRD, porosimetry, and microscopy studies.

Example 3

Sorbent Materials for PFAS Capture

Figure 28:
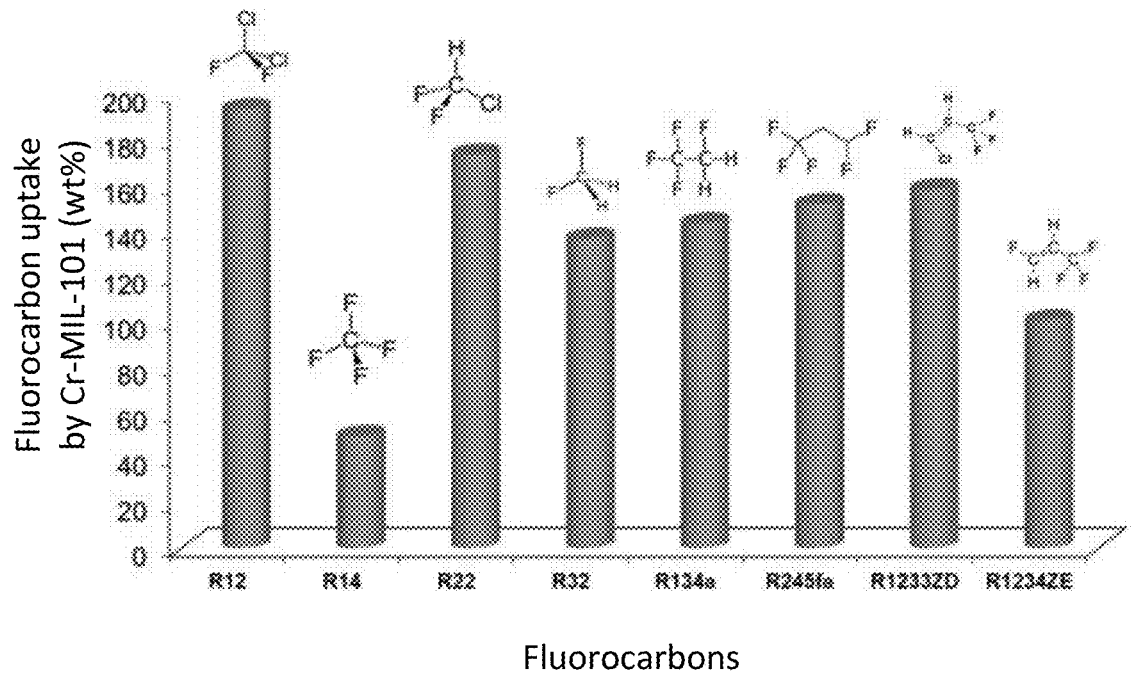
FIG. 28 is a bar graph showing uptake of various fluorocarbons by Cr-MIL-101.
Figure 29:
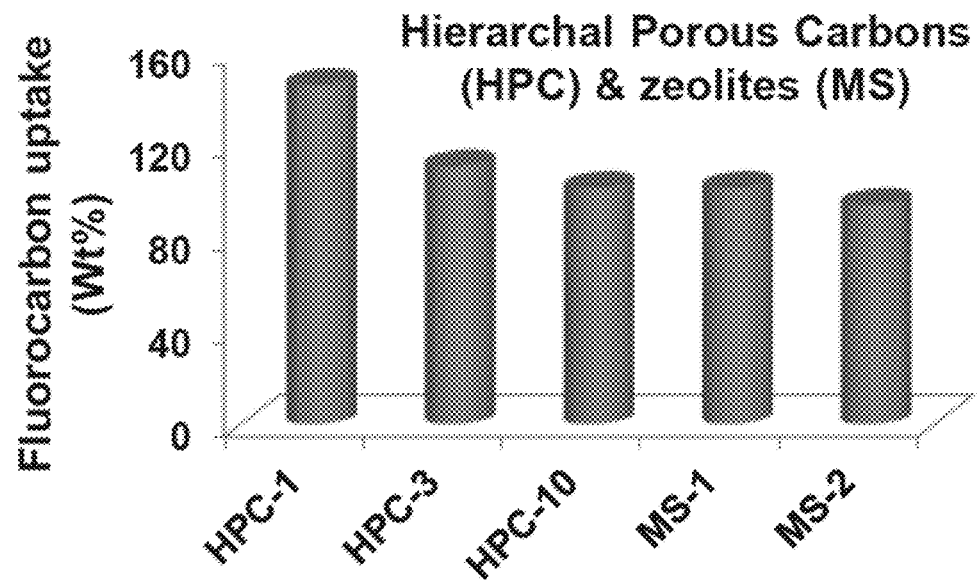
FIG. 29 is a bar graph showing uptake of $CH_2FCF_3$ by various hierarchical porous carbons and zeolites.
Figure 30:
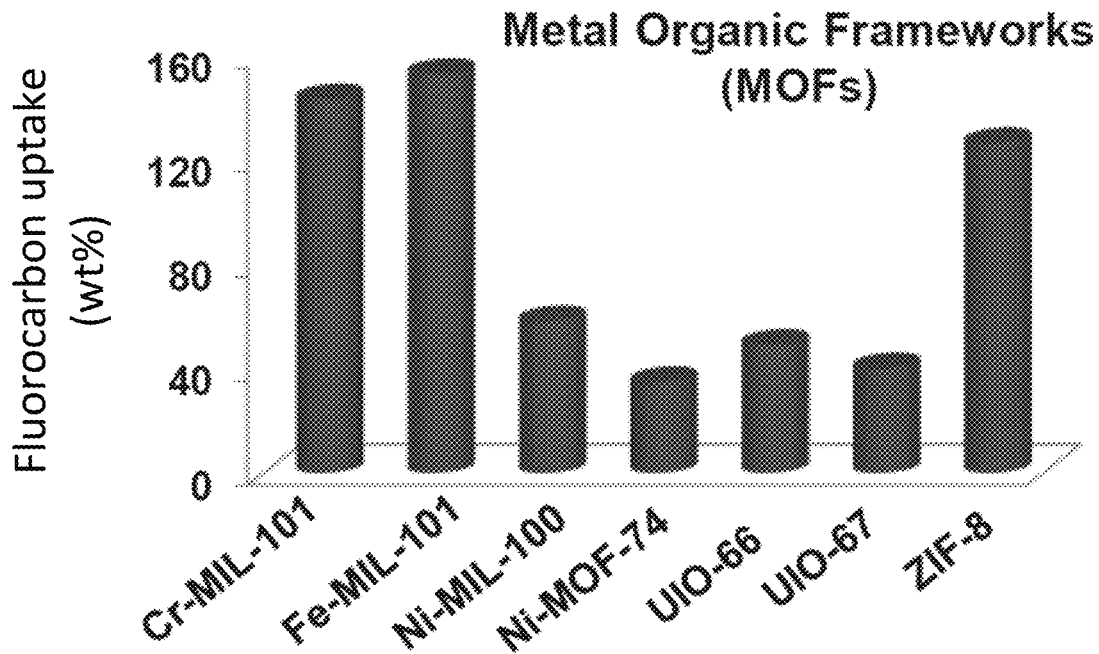
FIG. 30 is a bar graph showing uptake of $CH_2FCF_3$ by various metal organic frameworks.
Figure 31:
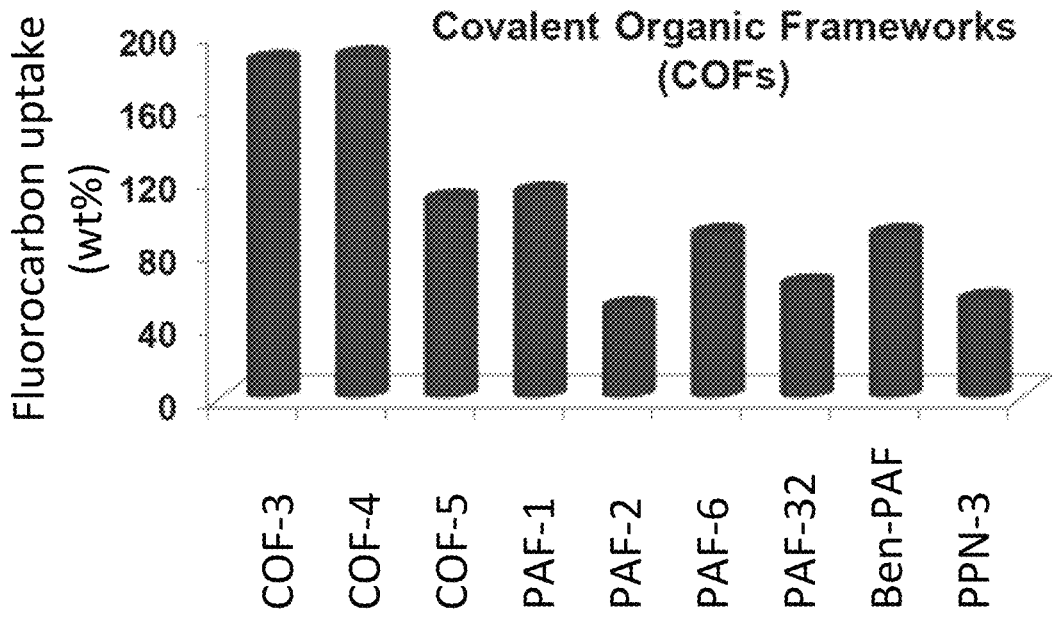
FIG. 31 is a bar graph showing uptake of $CH_2FCF_3$ by various covalent organic frameworks.

Several sorbent materials were evaluated for adsorption of various $C_1$-$C_4$ fluorocarbons. The sorbent materials included MOFs, COFs, COPs, HPCs, and zeolites. The evaluated materials included Cr-MIL-101 ($Cr_3OH(H_2O)_2$ $O(BDC)_3 \cdot 25H_2O$), Fe-MIL-101 $Fe_3OH(H_2O)_2$ $O(BDC)_3 \cdot 25H_2O$), Fe-MIL-100, Fe-MIL-88, HKUST-1, Ni-MOF-74, Co-MOF-74, Mg-MOF-74, Ni-BPP, Ni-TPP, Ni-BPM, Ni-TPM, UiO-66, UiO-67, ZIF-8, NU-1000, NU-901, MOF-525, MOF-545, MOF-801, MOF-808, NiZn-MOF-74, MIL-53, FeBTC, SIFSIX-1, CaSDB, NiPYC, HPC-1 (Ketjen black), HPC-2 (BP2000), HPC-3 (Norit® activated carbon), HPC-4 (Calgon CTC120 activated carbon), HPC-10 (Maxsorb® activated carbon), MS-1 (SBA-15), MS-2 (MCM-41), MS-3 (13X), MS-4 (HY), MS-5 (SSZ-13), PAF-1, PAF-2, PAF-6, PAF-32, Ben-PAF, PPN3, COP-1, COP-2, COP-3, COP-99, COP-109 (FIG. 28 shows the uptake of several fluorocarbons by Cr-MIL-101. FIGS. 29-31 show uptake of $CH_2FCF_3$ by various HPCs and zeolites (FIG. 29), MOFs (FIG. 30), and COFs (FIG. 31).

The capture of a diverse range of PFAS by a variety of sorbent materials was compared with GAC. Embodiments of the disclosed sorbent materials demonstrated significantly higher PFAS uptake capacity in batch contact experiments from groundwater compared to GAC, presumably due to a combination of higher specific electronic affinity and superfluorophilicity. For sorption studies, batch contact experiments were performed using groundwater from DOE well 299-W19-36 at Hanford, WA (Table 2).

TABLE 2

| Constituent | µg/L | Constituent | µg/L |
|---|---|---|---|
| Calcium | 122,000 | Nitrate | 317,000 |
| Chloride | 181,000 | Sodium | 118,000 |
| Total Cr | 17.3 | Potassium | 7,010 |
| Cr(VI) | 0.05 | Carbonate | 116,000 |
| Magnesium | 36,400 | Organics | 123,000 |

The groundwater samples were spiked with select PFAS. For the batch contact experiments, the PFAS containing water were contacted with a given mass of the chosen porous-framework materials for 24 hours, and the PFAS' sorption was monitored using $^{19}F$ NMR of the solution pre- and post-contact both periodically as well as after 24 hours.

Figure 32:
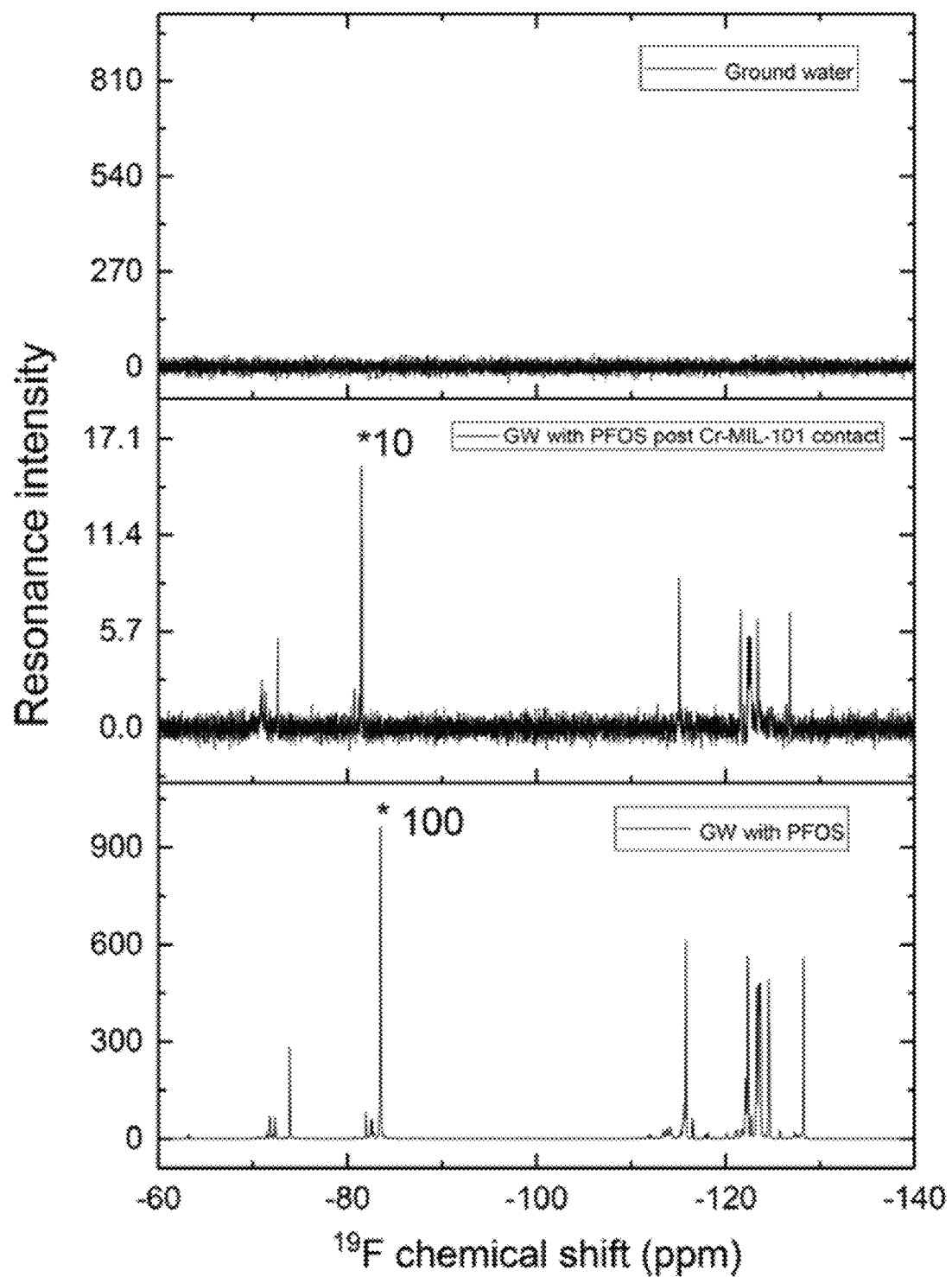
FIG. 32 shows solution phase $^{19}F$ NMR spectra of groundwater (top panel), 5 mL of 10 mM PFOS in ground water (lower panel), and the PFOS-spiked groundwater collected post-contact with 5 mg of Cr-MIL-101 (middle panel).

Additionally, a groundwater sample spiked with 5 mL of 10 mM PFOS was monitored pre- and post-contact with 5 mg of Cr-MIL-101 for 144 hours, as shown in FIG. 32. While the initial groundwater sample did not contain any fluorine species, spiking it with PFOS resulted in a distinct PFOS signal. Contact of the PFOS-spiked groundwater with Cr-MIL-101 sorbent resulted in a 95% decrease in the intensity of all the fluorine resonances in the solution phase, demonstrating capture of PFOS by the sorbent.

Figure 33:
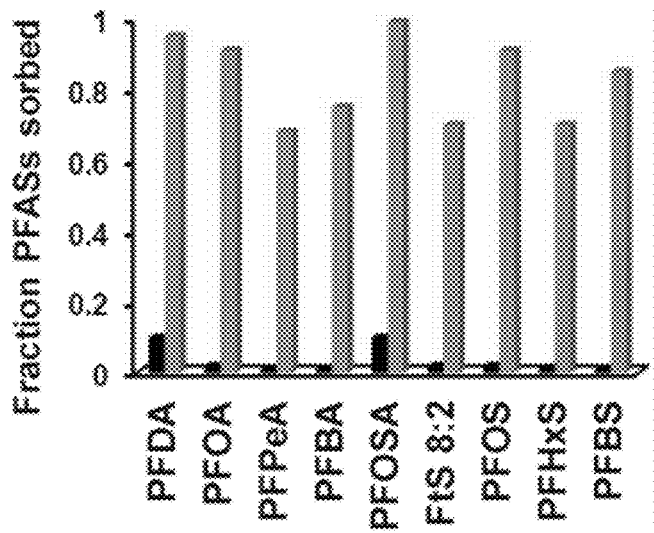
FIG. 33 is a bar graph showing uptake of several PFAS by granulated activated carbon (left bar of each pair) or UiO-66 (right bar of each pair).
Figure 34:
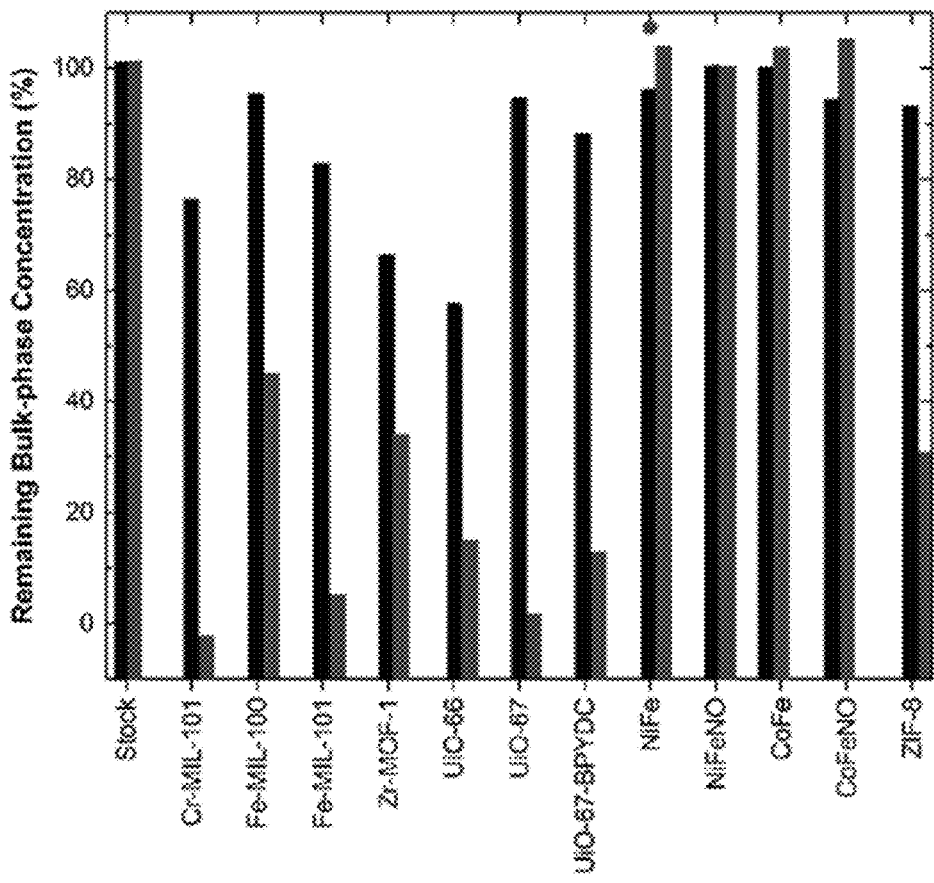
FIG. 34 is a bar graph showing uptake of PFOA (left bar of each pair) and PFOS (right bar of each pair) by several sorbents.

FIGS. 33 and 34 demonstrate the comparative uptake of nine PFAS by GAC and several sorbents as disclosed herein, including Cr-MIL-101, Fe-MIL-100, Fe-MIL-101, Zr-MOF-1, UiO-66, UiO-67, UiO-67-BPYDC, NiFe, NiFeNO, CoFe, CoFeNO, and ZIF-8.

In FIG. 33, the sample was groundwater from the DOE well spiked with PFAS; the ratio of sorbent to PFAS was 1:1 w/w; left bar in each pair is GAC, right bar in each pair is UiO-66. The PFAS were PFDA (perfluorodecanoic acid), PFOA (perfluorooctanoic acid), PFPeA (perfluoropentanoic acid), PFBA (perfluorobutanoic acid), PFOSA (perfluorooctane sulfonamide), FtS 8:2 (8:2 fluorotelomer sulfonic acid), PFOS (perfluorooctane sulfonate), PFHxS (perfluorohexyl sulfonate), and PFBS (perfluorobutyl sulfonate). The MOF, UiO-66, showed general affinity toward all of the PFAS with an uptake capacity 1-100 fold higher than commercial GAC. Similarly high uptakes were also observed for the MOFs UiO-67 and UiO-68. This high affinity is presumably due to the superfluorophilicity of the MOFs.

In FIG. 34, 1 mM PFOA (left bar of each pair) and PFOS (right bar of each pair) were combined with 10 mg of each probe in deionized water. The comparative results highlight the effects of porosity as well as electronics of the porous framework in the PFAS uptake.

Figure 35:
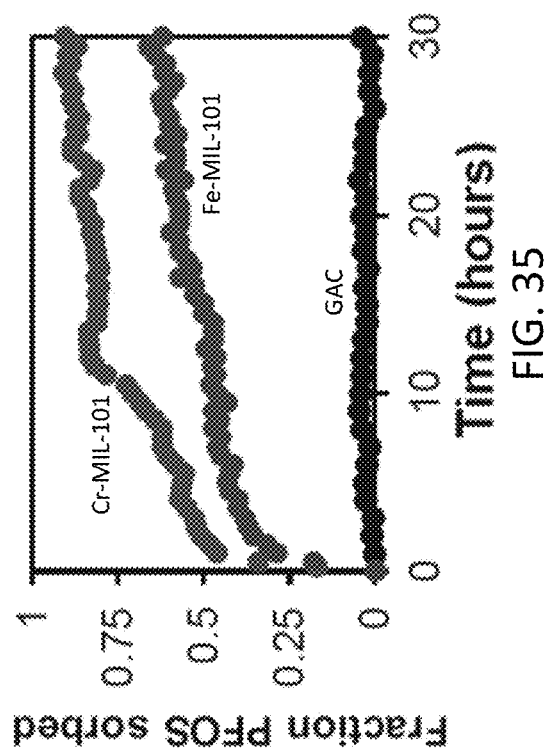
FIG. 35 is a graph showing kinetics of uptake of 10 mM PFOS solution in groundwater by 10 mg of GAC, Fe-MIL-101, or Cr-MIL-101.

FIG. 35 shows kinetics of uptake of 10 mM PFOS solution in groundwater by 10 mg of GAC, Fe-MIL-101, or Cr-MIL-101. The ratio of probes to sorbent was 1:1 w/w. The results showed that MOF sorbents were significantly better than GAC, presumably because high surface areas and huge pore volumes elevate high sorption capacities and rapid kinetics due to a high number of active-sites/active site density in the pores. Additionally, the study demonstrated faster PFOS sorption kinetics in Cr-MIL-101 compared to Fe-MIL-101.

Figure 36:
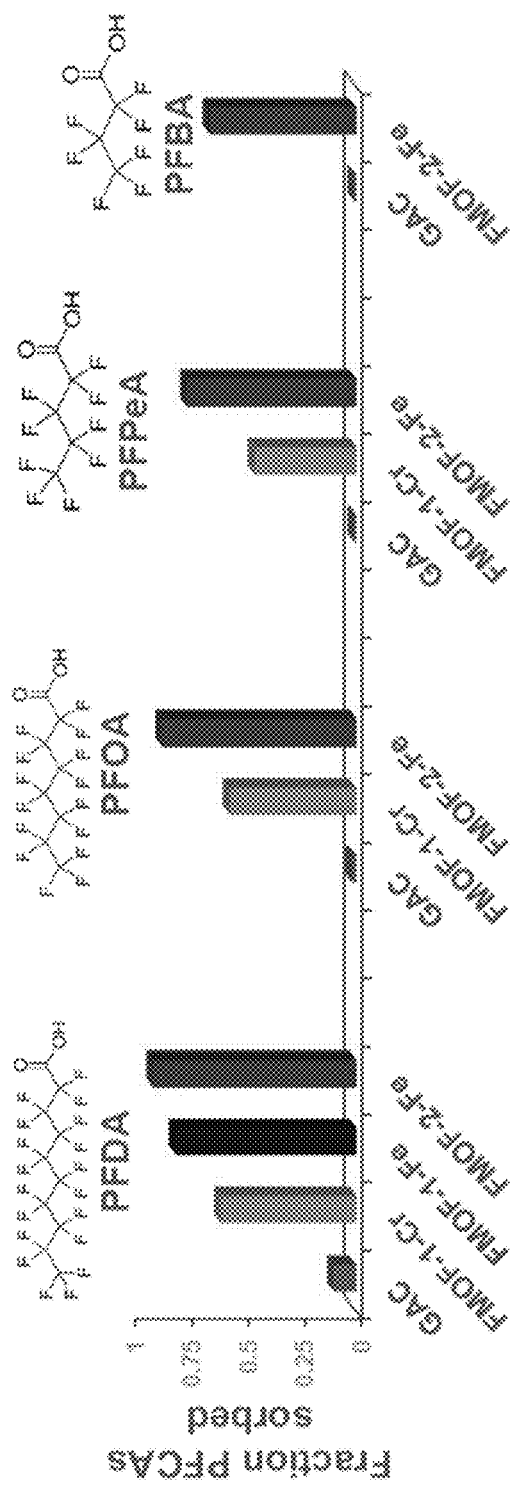
FIG. 36 is a bar graph showing 24-hour uptake of PFDA, PFOA, PFPeA, and PFBA with GAC, Cr-MIL-101, Fe-MIL-101, and Fe-MIL-100.
Figure 37:
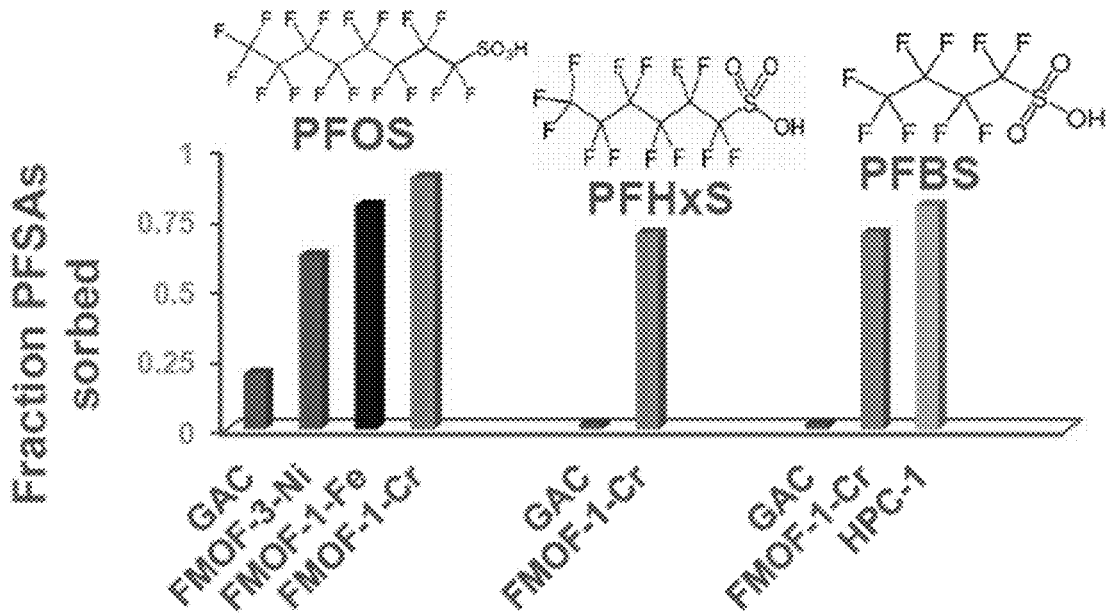
FIG. 37 is a bar graph showing 24-hour uptake of PFOS, PFHxS and PFBS by GAC, NiMOF-74, Fe-MIL-101, Cr-MIL-101, and HPC-1.
Figure 38:
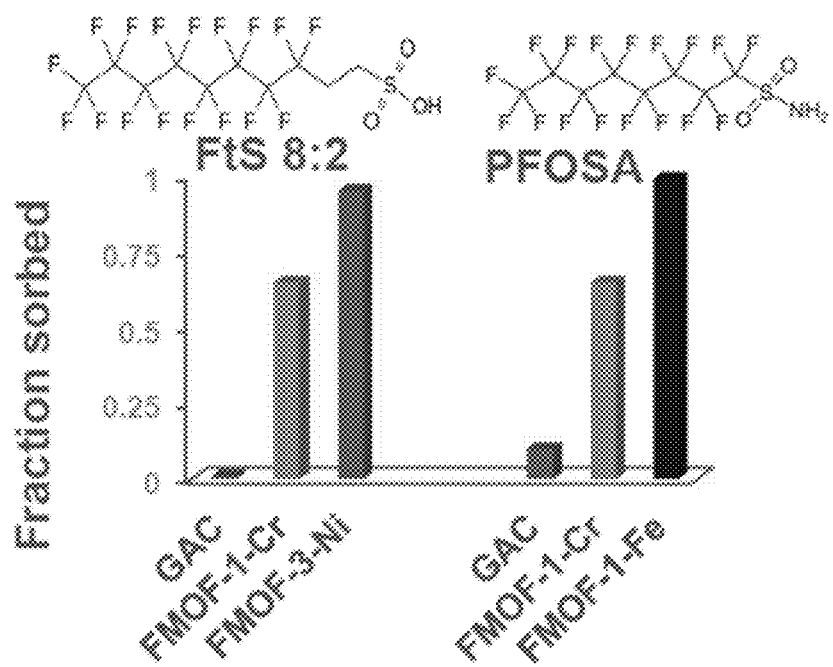
FIG. 38 is a bar graph showing 24-hour uptake of FtS 8:2 and PFOSA by GAC, Cr-MIL-101, Ni-MOF-74, and Fe-MIL-101.

It was further demonstrated that probes can be tailored to target specific PFAS functionalities and also to separate varying chain lengths. Groundwater from the DOE well was spiked with PFAS and exposed to various sorbents at a PFAS/sorbent ratio of 1:1 w/w. FIG. 36 shows 24-hour uptake of PFDA, PFOA, PFPeA, and PFBA with GAC, Cr-MIL-101, Fe-MIL-101, and Fe-MIL-100. FIG. 37 shows 24-hour uptake of PFOS, PFHxS and PFBS by GAC, NiMOF-74, Fe-MIL-101, Cr-MIL-101, and HPC-1. FIG. 38 shows 24-hour uptake of FtS 8:2 and PFOSA by GAC, Cr-MIL-101, Ni-MOF-74, and Fe-MIL-101. FIGS. 36-38 demonstrate that selectivity toward specific PFAS functionalities could be achieved by careful modulation of capture probes. Thus, the mesoporous MOF Cr-MIL-101 based on a Cr(II/III) metal center showed a high affinity toward the perfluorosufonic acids (PFSAs); this is presumably due to the affinity of the Cr toward both the F and S. Similar specific affinities are presumably responsible for (i) the mesoporous Fe(II/III)-based MOF Fe-MIL-101 based on softer metal centers that show a higher affinity toward the softer Lewis bases, which consist of perfluorocarboxylic acids (PFCAs), and (ii) the Ni-MOF-74 frameworks that show higher selectivities toward the telomers.

Example 4

PFOS Detection with Cr-MIL-101/CNT and Fe-MIL-101 Probes

A fluidic device was prepared as described above. The probes were Cr-MIL-101/CNTs or Fe-MIL-101/CNTs. The probes were prepared by connecting CNT-COOH tethering to MOFs via covalent bonding. The extremely high surface area and pore volume of mesoporous metal-organic framework (MOF) Cr-MIL-101 was used as the probe for targeted PFOS capture based on the affinity of the chromium center towards both the fluorine tail groups as well as the sulfonate functionalities as demonstrated by spectroscopic (NMR and XPS) and microscopic (TEM) studies. The device was connected to an impedance analyzer for EIS readings using standard electrical connections as described above. For impedance measurements, solutions of PFOS were prepared in 0.1× PBS (pH 7.2), and serial dilutions were done in 0.1× PBS as well.

EIS readings were taken at each step and at 5 minute intervals in each protocol step. The syringe pump (New Era Just Infusion Pump NE-1000, Farmingdale, NY) was used to first wash the fluid device with PBS 0.1× buffer solution (pH 7.2) at a flow rate of 5 µL/min for 30 mins. Post washing, different concentrations of PFOS in 0.1× PBS (pH 7.2) were charged into the system at 5 µL/min for 30 min. The sensitivity of and the detection limit of the probe was conducted using serial dilutions of the PFOS over concentrations ranging from µg to ng. All serial dilutions were carried out by diluting the stock solution in 10× PBS solution at a pH of 7.2.

A syringe pump was connected to the inlet of the device. Preliminary washing of the device was done using 0.1× (pH 7.2) PBS solution at a flow rate of 1 µL/min for 2 hours or until the EIS signal stabilized. The stabilization of the EIS signal was marked by two spectra taken 5 minutes apart remaining invariant. This stabilized EIS signal was treated as the baseline blank measurement. Post-stabilization, the 0.1× PBS solutions were switched with PFOS solutions at desired concentrations. Each concentration was run for 2 hours at a flow rate of 1 µL/min, following which the device was washed with 0.1× (pH 7.2) PBS solution at a flow rate of 1 µL/min for 30 minutes-3 hours to ensure stabilization of the EIS signal as well as to allow any loosely bound interferences to be washed off.

Figure 39:
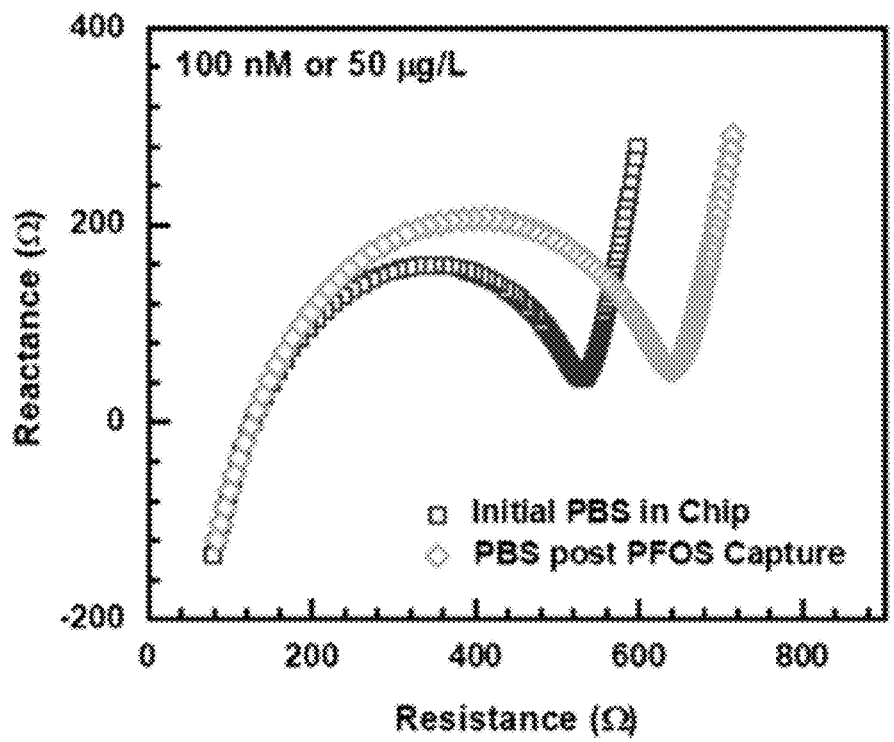
FIG. 39 shows Nyquist plots for response of Cr-MIL-101 probes in 0.1 M PBS buffer, and 100 nM (50 µg/L) PFOS in PBS.
Figure 40:
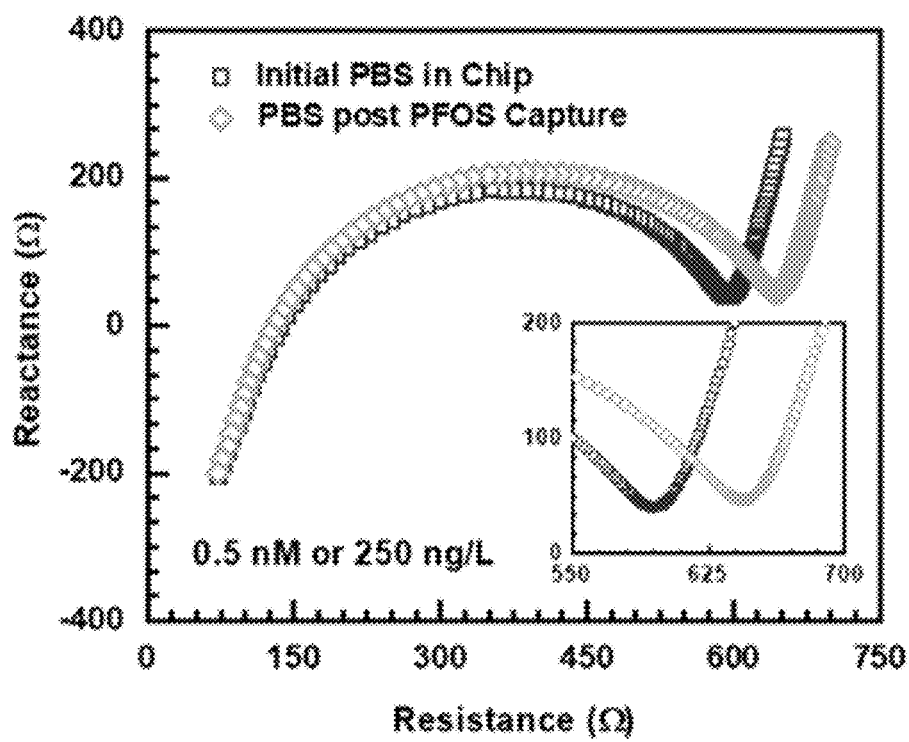
FIG. 40 shows Nyquist plots for response of Cr-MIL-101 probes in 0.1 M PBS buffer, and 0.5 nM (250 ng/L) PFOS in PBS.
Figure 41:
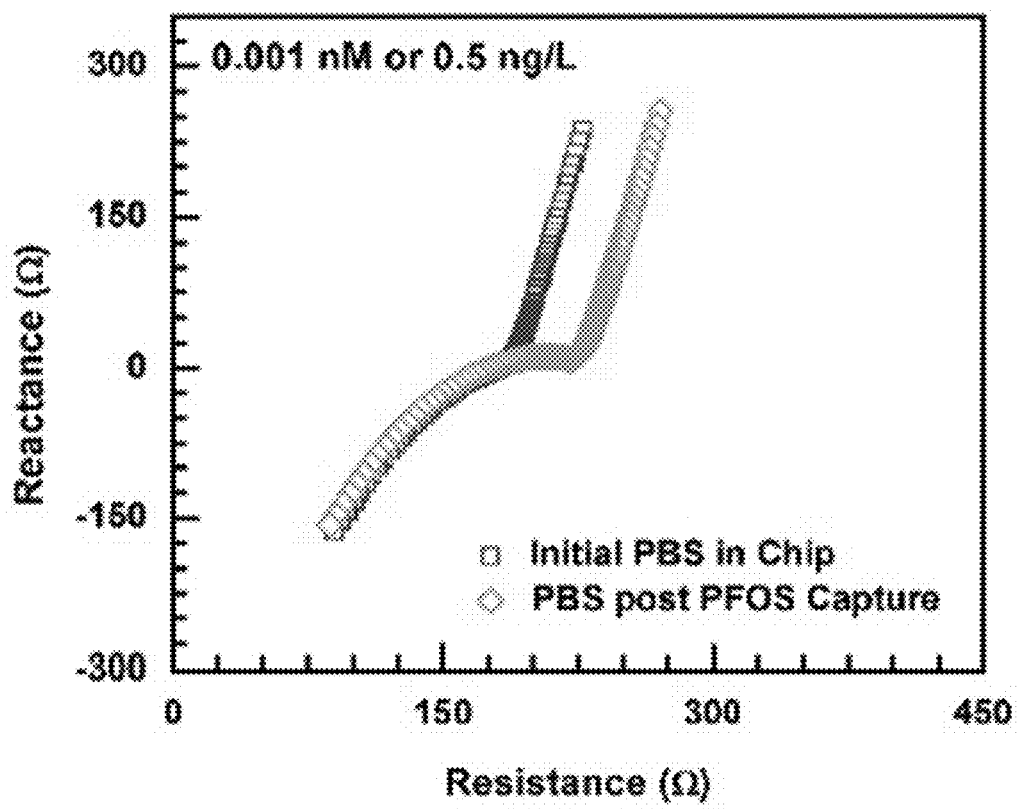
FIG. 41 shows Nyquist plots for response of Cr-MIL-101 probes in 0.1 M PBS buffer, and 0.001 nM (0.5 ng/L) PFOS in PBS.
Figure 42:
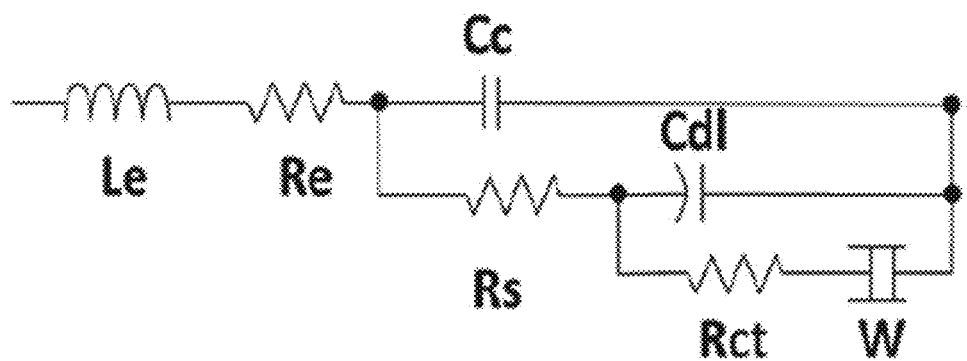
FIG. 42 depicts a classical Randle circuit used to model the electrochemical impedance spectrum response of Cr-MIL-101 probes upon PFOS capture.

A change in the EIS signal between pre-wash and post-wash indicates attachment of the PFOS to the MOF-CNT complex. The EIS spectrum (Nyquist curve) of Cr-MIL-101/CNT in 0.1 M PBS buffer was characterized by a conventional semi-circular region followed by a linear region. Introduction of PFOS at concentrations of 100 nM (50 µg/L), 0.5 nM (250 ng/L), and 0.001 nM (0.5 ng/L) in the analyte stream of PBS buffer showed a marked change in the impedance profile of the Cr-MIL-101 receptors compared to the buffer solution itself, with a discernible increase in the radius of curvature of the semi-circular region of the Nyquist curves shown in FIGS. 39-41, respectively. The EIS response upon PFOS capture by Cr-MIL-101 receptors packed between the NP-IDµE was modelled using the circuit model (commonly used for IDµE) shown in FIG. 42 using an in-house Matlab code (Kaushik et al., *Sci Rep* 2018, 8(1):9700; Ding et al., *ACS Sens* 2017, 2(2):210-217). In the equivalent circuit, Re is the inherent resistance in the device, Le is the parasitic inductor in the device due to external noises, Rs is the resistance of the solution filling the device, Cdl is the double layer capacitance, Rct is the charge transfer resistance, Ws is the Warburg element as the impedance associated with the diffusion rate of the reactants, and Cc is the direct capacitance between the two electrodes (FIG. 42). Cc or the cell capacitance is the capacitance between the two non-planar finger electrode combs of the NP-IDµE. Rs, the resistance of the solution represents the total impedance of the interface between the gold electrode and electrolyte. Cdl is the double layer capacitance that is due to the interfacial ionic polarization between the electrolyte and the tightly packed Cr-MIL-101 receptors. Rct and the Warburg impedance are in series and is parallel to Cdl since both phenomena occur simultaneously. The charge transfer or polarization resistance Rct is associated with the transfer of the electrons from the electrolyte onto the tightly packed Cr-MIL-101 receptors. Rct is heavily dependent on several factors like the available surface area of the tightly packed Cr-MIL-101 receptors among others. Hence, the capture and binding of PFOS by Cr-MIL-101 presumably leads to alteration of the charge-transfer or polarization resistance due to change in the available electrode surface area. This is the key contributor to the sensor signal with all other circuit elements being chiefly parasitic and not contributing significantly. Based on this model, the increase in the radius of curvature of the semi-circular region indicates that the charge transfer resistance (Rct) increases in the Cr-MIL-101 post PFOS exposure.

To quantify the effect of varying PFOS concentrations as well as to account for the non-identical MOF loading from across chips, the EIS signal from the chip was normalized using the relation:

$$\text{Symbol} = \left(\frac{R_{PFOS} - R_{MOF}}{R_{MOF}}\right)$$

where $R_{PFOS}$ and $R_{MOF}$ are the charge transfer resistances (Rct) from Cr-MIL-101 post PFOS exposure, and prior to PFOS exposure respectively. Using this normalization scheme, the charge transfer resistance showed a linear correlation with PFOS concentrations. The line was fit to the model equation y=b*In(x+c)+a, where y=resistance (Ω), x=PFOS concentration (ng/L), a=0.28517Ω, b=0.01348Ω, and c=2.74951×10$^{-10}$; $R^2$=0.9854. Based on the analysis, a quantification limit of 0.5 ng/L was obtained, which is unprecedented for portable approaches for PFOS detection and quantification.

Figure 43:
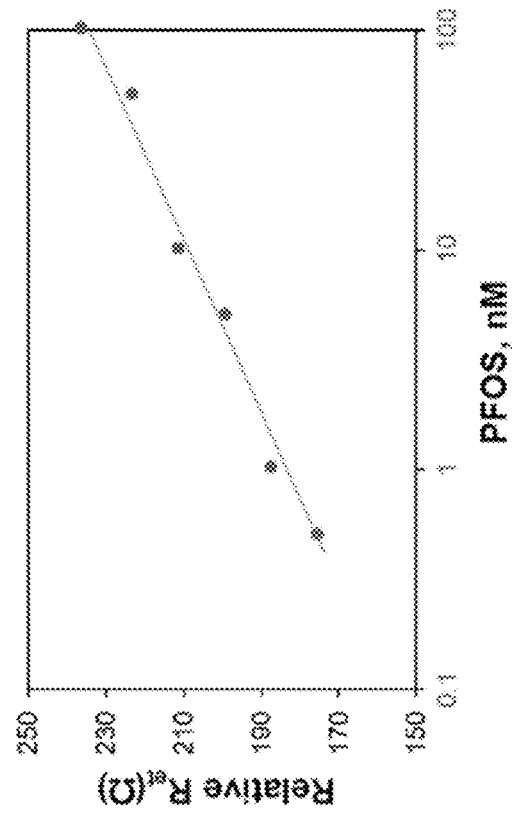
FIG. 43 shows Nyquist plots for response of Cr-MIL-101/CNT probes with increasing PFOS concentration.
Figure 44:
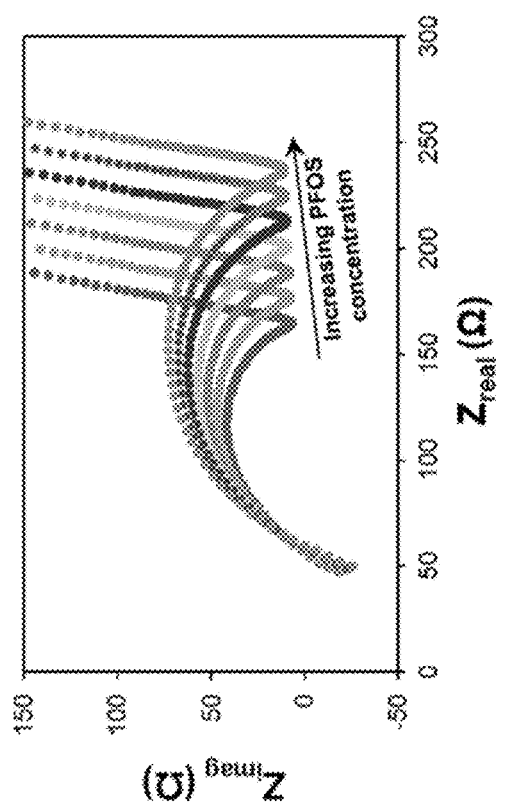
FIG. 44 is a calibration curve based on the data of FIG. 43.

FIG. 43 shows Nyquist plots for response of the Cr-MIL-101/CNT probes as the PFOS concentration increased from 0.5-100 nM. FIG. 44 is a calibration curve based on the data of FIG. 43. EIS was used to interrogate the CNT interface as EIS is a powerful interfacial analytical tool that has been applied extensively to characterize charge transport across membranes and detect interfacial binding events. The observed EIS spectrum (Nyquist curve) reflects the change in the MOF/CNT to macromolecule passage including surface activation. It is important to note that a non-faradaic impedance approach was used. In a non-faradaic impedance approach, there is no redox active probe. The transduction occurs due to changes in the surface dielectric, charge distribution or local conductance, which is accessed using capacitance. As can be seen from FIG. 43, there was a progressive increase in impedance with increase in PFOS concentration, suggesting binding of PFOS on the surface. Based on this, a calibration curve was constructed, which showed a linear variation of Ret with increasing PFOS concentration (FIG. 44). This is the first demonstration of the detection of PFOS using a MOF/CNT capture probe in a continuous flow, in solution.

Figure 45:
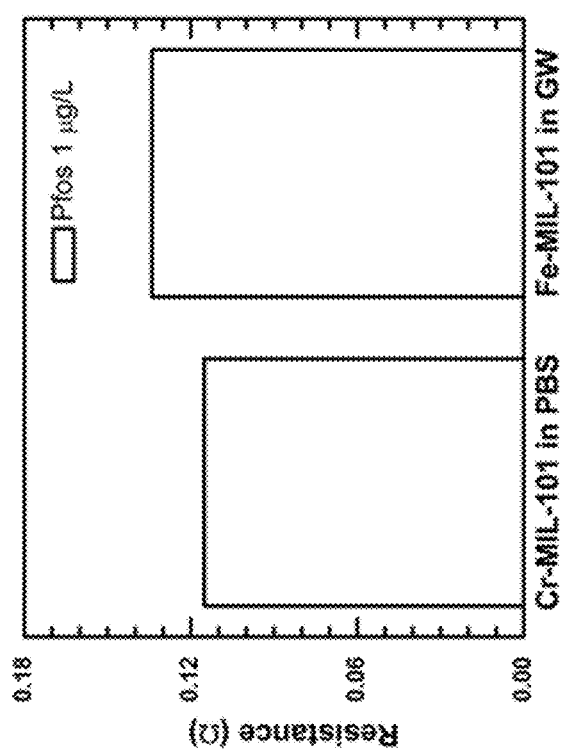
FIG. 45 is a bar graph showing response of Cr-MIL-101 and Fe-MIL-101 probes to PFOS in PBS and groundwater, respectively.

Groundwater samples from DOE well 299-W19-36 at Hanford, WA (see Example 3) were spiked with 1 μg/L PFOS and flowed through the fluidic device. EIS spectra were obtained pre- and post-sample flow. Although Cr-MIL-101 provided an excellent signal for PFOS in PBS buffer (FIGS. 38-40), a negligible signal was obtained for PFOS in groundwater (GW). In contrast, however, Fe-MIL-101 provided an excellent signal for PFOS in GW, which was comparable to that of PFOS in PBS with Cr-MIL-101 (FIG. 45).

Example 5

PFOS Bond Polarization with Sorbent Binding and Thermal Degradation

Figure 47:
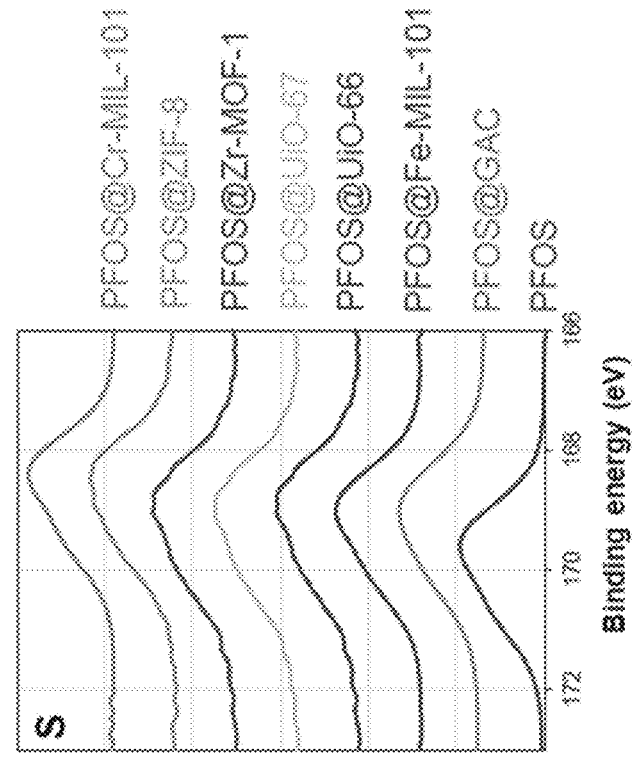
FIG. 47 shows polarization of the C—S bond in PFOS by various sorbent materials as determined by XPS.
Figure 46:
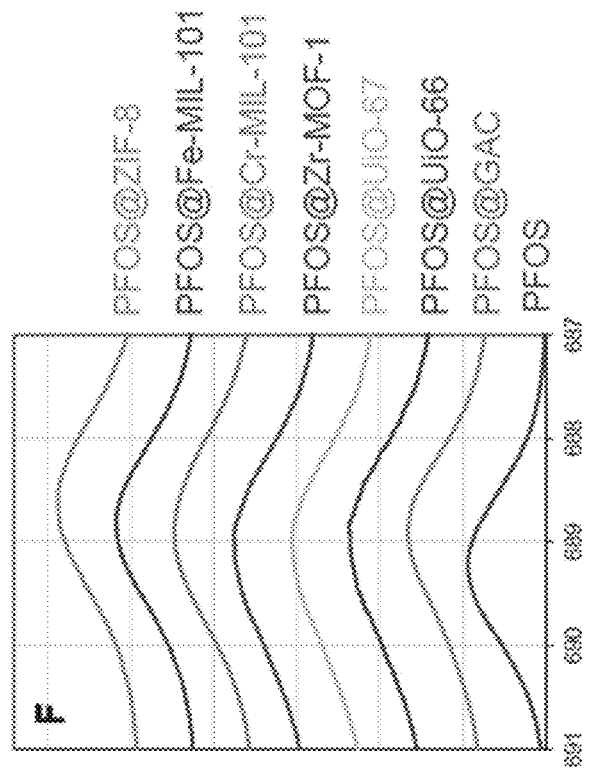
FIG. 46 shows polarization of C—F bonds in PFOS by various sorbent materials, as determined by X-ray photoelectron spectroscopy (XPS).

A range of sorbents were observed to demonstrate the ability to polarize bonds in PFOS molecules post-sorption. FIGS. 46 and 47 show the polarizations of C—F and C—S bonds in PFOS, respectively, upon sorption onto different sorbents as indicated by lowering of the binding energies measured using X-ray photoelectron spectroscopy. The C—F bonds were polarized most by ZIF-8, while the C—S bond was maximally polarized by Cr-MIL-101.

Figure 48:
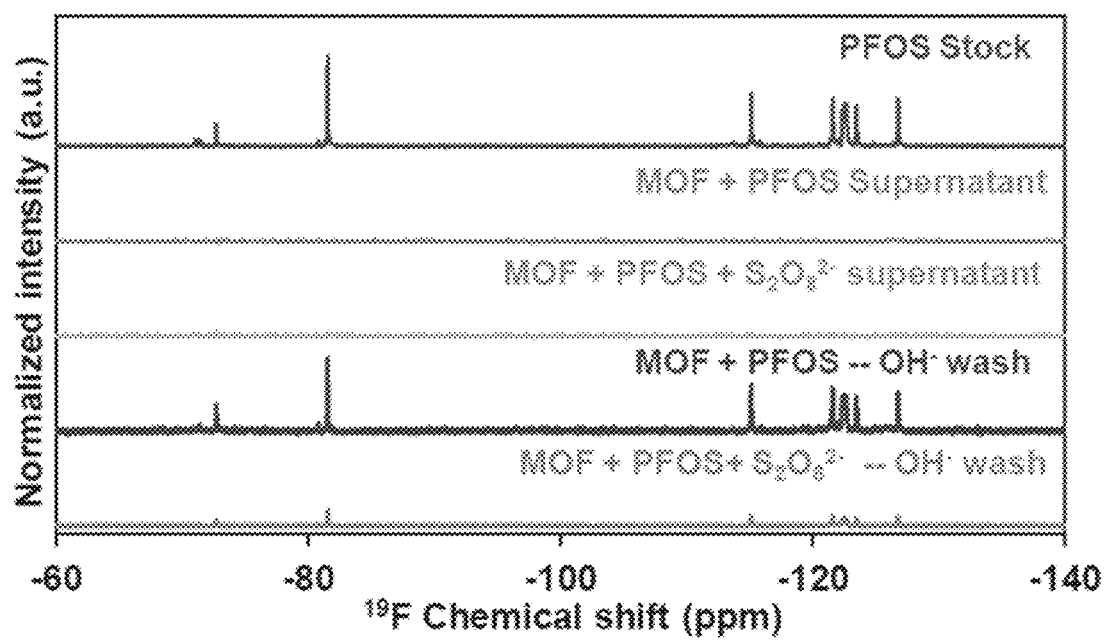
FIG. 48 shows $^{19}$F liquid state NMR spectra of 1 mM PFOS stock solution, supernatant post contact of PFOS with Cr-MIL-101, supernatant post contact of PFOS+$S_2O_8^{2-}$ with Cr-MIL-101, OH$^-$ wash of Cr-MIL-101 post PFOS contact, and OH$^-$ wash of Cr-MIL-101 post PFOS+$S_2O_8^{2-}$ contact.

Thermal degradation studies were performed by reacting a 1 mM PFOS stock solution with 100-fold excess of $S_2O_7^{2-}$, in the presence of a MOF Cr-MIL-101 for 6 hours in a closed vial at a temperature of 80° C. A control experiment was conducted where the PFOS stock was contacted with Cr-MIL-101 for the same length of time at the same temperature in the absence of the $S_2O_7^{2-}$ amendment. The reactions were monitored using $^{19}$F liquid NMR spectroscopy on the supernatant solutions (FIG. 48). The NMR spectra show quantitative PFOS removal by the MOF within the timeframe. To evaluate the destruction of PFOS, the used MOFs were washed with 0.1 M NAOH. The $^{19}$F NMR of the wash solution in the absence of $S_2O_8^{2-}$ showed ~95% PFOS recovery based on the near equal intensity of the resonance intensities of the wash with the stock (post volume corrections). On the other hand, the $S_2O_7^{2-}$ contacted solution showed a ~70% loss of PFOS intensity, suggesting PFOS degradation. No additional resonances were observed suggesting multiple scenarios ((i) conversion of PFOS to multiple degradation products each of which individually have concentrations not high enough to be detected by the NMR, or (ii) the degradation products are retained strongly within the MOF).

Figure 49:
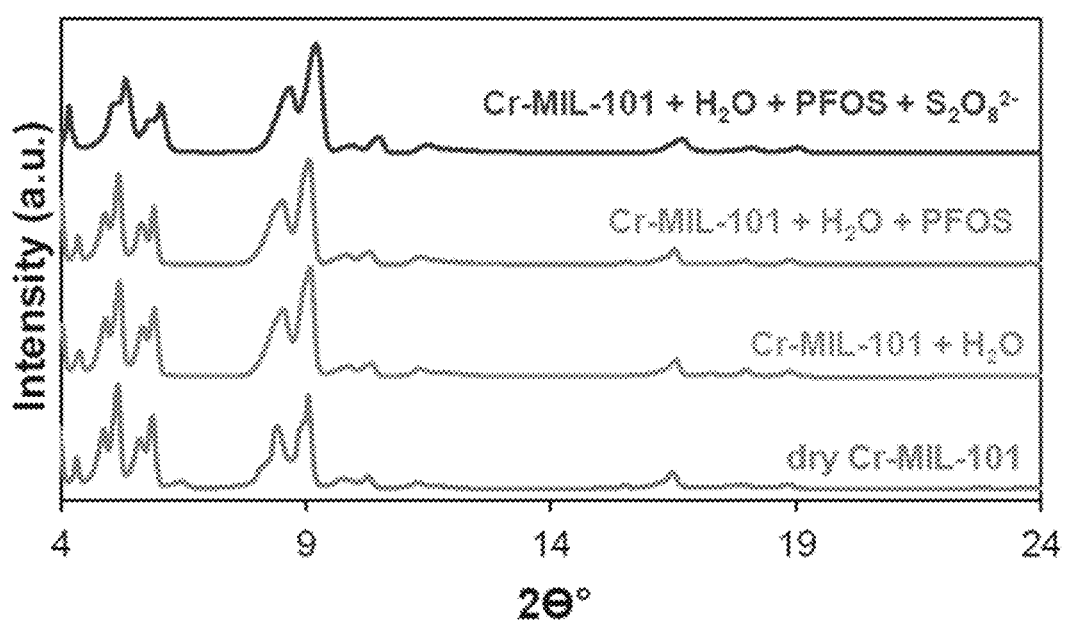
FIG. 49 shows X-ray diffractograms of dry Cr-MIL-101, Cr-MIL-101 wetted with deionized water, Cr-MIL-101 post PFOS contact, and Cr-MIL-101 post PFOS+$S_2O_8^{2-}$ contact.

The MOF stability post contact with PFOS as well as $S_2O_8^{2-}$ was evaluated. X-ray diffraction studies on the MOF pre- and post-contact (FIG. 49) demonstrated no discernible loss in the crystallinity or structural integrity of the MOF post its contact with PFOS or $S_2O_8^{2-}$, as indicated by the similarity of the diffraction profiles. The results suggested the stability of the MOF to the $S_2O_8^{2-}$ amendment under the subjected reaction conditions.

Example 6

PFOA Detection with Nickel Hexacyanoferrate (NiFe)

The synthesis of NiFe has been well reported in the literature. For the present work, the reaction involved mixing ferricyanide anions (50 mM aqueous solution of $K_3Fe(CN)_6$) with nickel cations (50 mM aqueous solution of $Ni(NO_3)_2 \cdot 6H_2O$) to produce a cubic crystalline Prussian blue framework (NiFe).

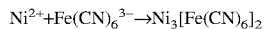

$$Ni^{2+} + Fe(CN)_6^{3-} \rightarrow Ni_3[Fe(CN)_6]_2$$

To ensure the effectiveness of NiFe as a potential sorbent for PFOA in aqueous media, batch contact experiments were performed and the exposed material, [PFOA]-NiFe, was characterized. Prior to PFOA exposure, as-synthesized NiFe powder was activated under vacuum at 150° C. for 12 h. The activated sorbent was then submerged in 10 mL of a 10 mM aqueous PFOA solution in a glass vial. The vial was shaken at ~200 rpm for 24 h to maintain homogeneity. After this soaking period, the solid sorbent material was separated by filtration and rinsed with fresh deionized $H_2O$. The washed, PFOA-exposed NiFe (herein, [PFOA]-NiFe) was dried in an oven at 120° C. for 12 h and characterized in comparison with the parent NiFe material. It should be noted that these relatively higher concentrations of PFOA solution were chosen for batch contact experiments in order to obtain observable results post sorption. At lower concentrations, similar to those probed for detection experiments, material properties probed via characterization techniques conducted in this study did not show significant observable differences after sorption of PFOA.

Figure 50:
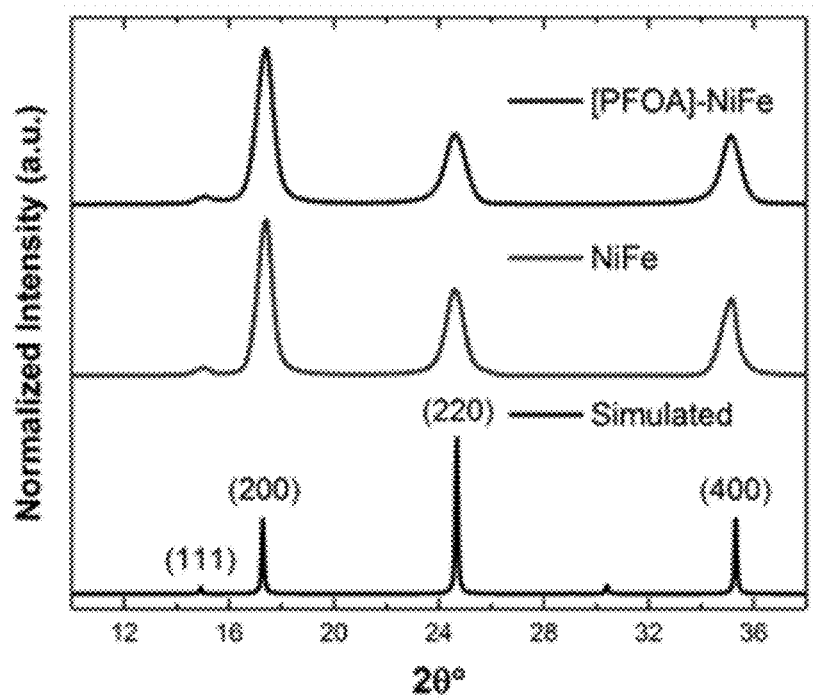
FIG. 50 shows powder X-ray diffraction spectra of nickel hexacyanoferrate (NiFe) before and after PFOA sorption in comparison with a simulated crystal structure of NiFe.

The structural integrity of the framework was confirmed using powder XRD as shown in FIG. 50. Experiments were performed with a Rigaku MiniFlex 600 X-ray diffractometer. The sample was placed in a powder sample holder under ambient conditions and a pattern was collected from the 2θ range of 5-40°. The step size was 2° min⁻¹. As compared to the simulated crystal structure, prominent peaks corresponding to the (200), (220) and (400) phases at ~17.5, 24.5 and 35.5, 2θ° respectively are all apparent in both the synthesized pristine parent material as well as the PFOA-exposed material.

Figure 51:
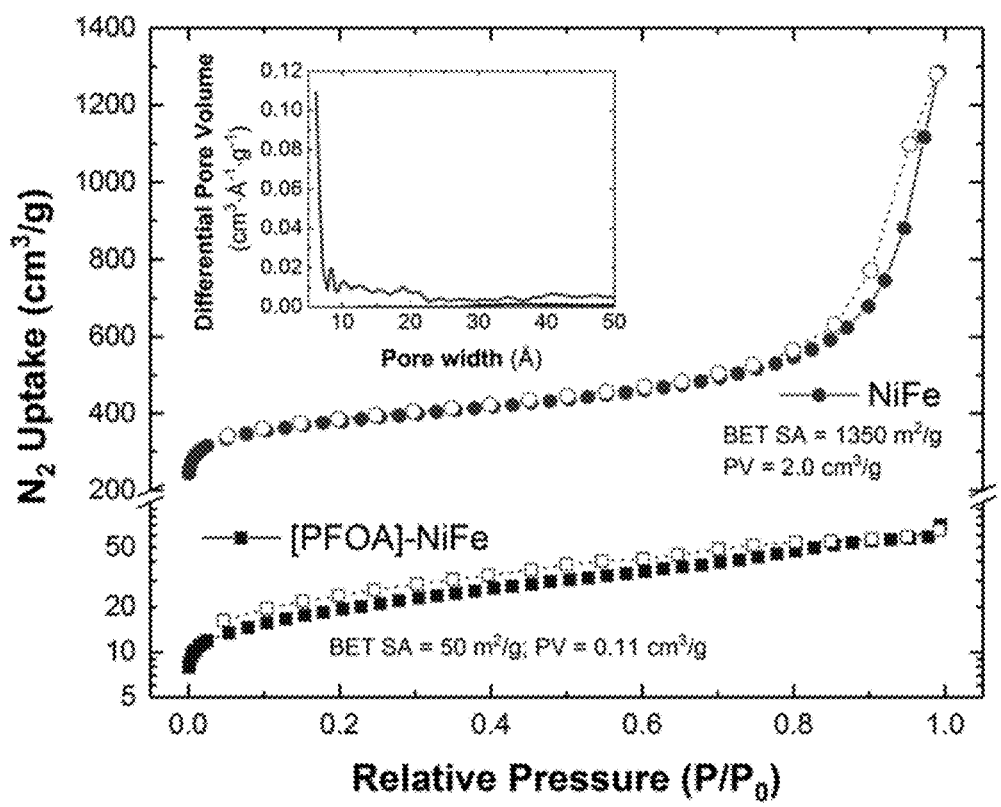
FIG. 51 shows $N_2$ sorption isotherms at 77K and corresponding pore size distributions showing BET surface areas and pore volumes of NiFe before and after PFOA sorption.

The porosity of the sample before and after PFOA uptake was characterized using nitrogen sorption isotherms collected at 77K as shown in FIG. 51. Porosimetry analysis was performed using N2 sorption isotherms measured at 77K via a Quantachrome Instruments (USA) Autosorb IQ2 volumetric uptake apparatus. BET surface areas, pore volumes and pore size distribution were derived using isotherm data as previously explained in detail. Both NiFe and [PFOA]-NiFe show characteristic IUPAC Type II isotherm indicative of both monolayer and multilayer adsorption stages. Monolayer coverage is observed to be complete by the inflection point of the isotherm at $P/P_0$~0.3. Pore size distribution (inset of FIG. 51) as calculated by NLDFT's (Non Localized Density Functional Theory) simulation model of a slit pore geometry indicates the highly microporous nature of NiFe with prominent pore sizes <10 Å. The BET surface area of NiFe was measured to be ~1350 m²/g, which drastically reduced after PFOA sorption to 50 m²/g. This is likely due to pore blockage, which limits access to nitrogen sorption sites apparent in the parent structure, even at higher pressures.

Figure 52:
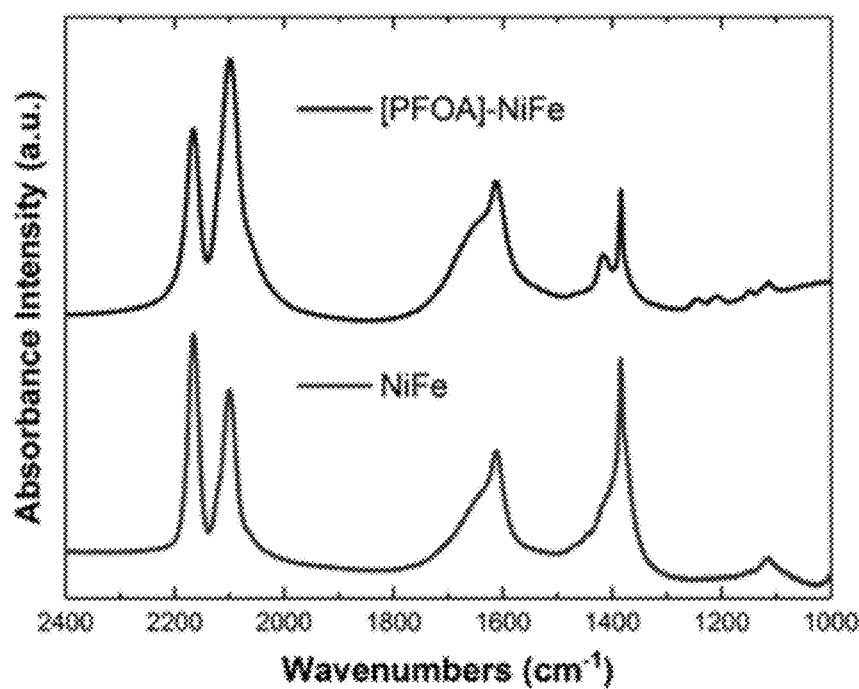
FIG. 52 shows infrared spectra of NiFe before and after PFOA sorption.

The presence of PFOA in [PFOA]-NiFe was confirmed using IR spectra (FIG. 52). Fourier transform infrared (FTIR) spectroscopy measurements were collected using a ThermoScientific (USA) Nicolet FTIR spectrometer equipped with CaF2 windows and an MCT detector with a resolution of 4 cm⁻¹. A minimum of 64 scans were accumulated for each spectrum. The solid materials were mixed with KBr powder to form pellets before characterization. The spectra for pure KBr was used as a background and subtracted from each subsequent scan. Characteristic vibration frequencies corresponding to —CF₃ and —CF₂ moieties of the PFOA structure are apparent in the exposed sample at wavenumbers between 1100 and 1300 cm⁻¹, which are not apparent in the parent NiFe, as expected.

Figure 53:
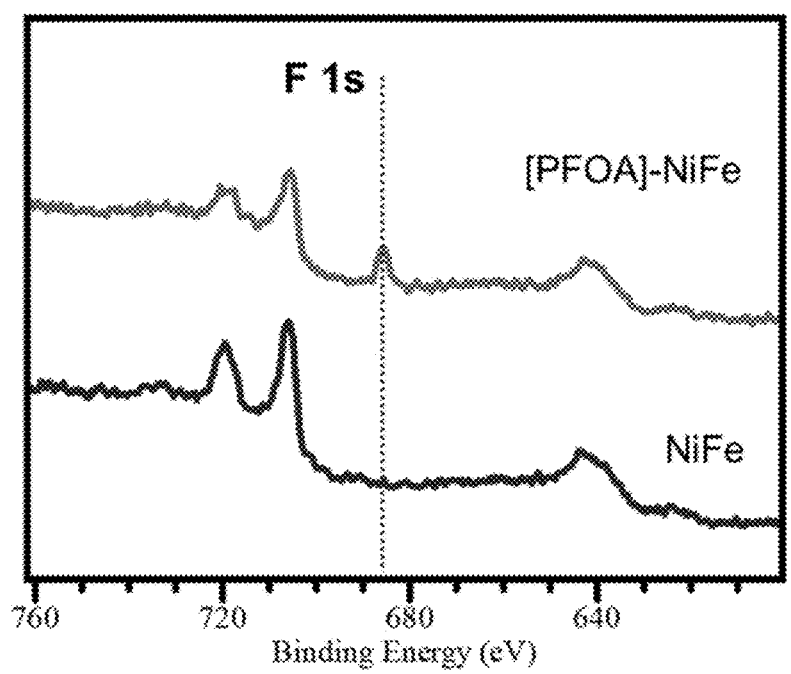
FIG. 53 shows X-ray photoelectron spectra identifying presence of PFOA on NiFe after uptake.

Evidence of sorbed fluorocarbon in [PFOA]-NiFe was also shown via XPS data (FIG. 53). X-ray photoelectron spectroscopy (XPS) was performed using a Kratos Analytical (Manchester, U.K.) Axis Ultra DLD spectrometer. This consists of a high performance Al Kα monochromatic x-ray source (1486.6 eV) and a high resolution spherical mirror analyzer. X-ray source was operated at 105 W and the emitted photoelectrons were collected at the analyzer entrance slit normal to the sample surface. The data acquisition was carried out in hybrid mode with analysis area of 700×300 μm. The survey spectra were recorded at pass energy of 160 eV with 0.5 eV step size and high resolution spectra were recorded at pass energy of 40 eV with step size of 0.1 eV. The pass energy 20 eV in the 700×300 μm analysis area is referred to the FWHM of 0.65 eV for Ag 3d5/2. The charge neutralizer with low energy electrons was used to exclude the surface charging effects and the binding energy of C 1s at 285 eV was used as the charge reference. A clear peak in the F 1s region at ~686 eV of the sorbed sample and a lack of this peak at this binding energy in the pristine sample further confirmed the capture of PFOA by NiFe.

The working electrode consisted of a glass slide coated with a conductive layer of glass, onto which the NiFe capture probe was deposited in-situ from aqueous solution. Briefly, a carefully measured area of the conductive surface was submerged in a stirring 50 mL (of 50 mM) aqueous solution containing dissolved nickel nitrate (Soln. A). The remaining area of the slide was masked with tape. After equilibration with the submerged glass slide for ~15 min, 50 mL (of 50 mM) aqueous solution containing K₃Fe(CN)₆ (Soln. B) was added dropwise slowly into Soln. A while continuing to stir. The combined 100 mL solution mixture was further stirred at room temperature for 24 hours. Subsequently, the slide was taken out of solution and rinsed with DI water (×3) and methanol (×3). The resultant slide was allowed to air dry for 1 hour. The tape was removed, and the non-coated areas were carefully wiped clean with isopropyl alcohol. The resultant slide was carefully stored in vials for use.

Figure 54A:
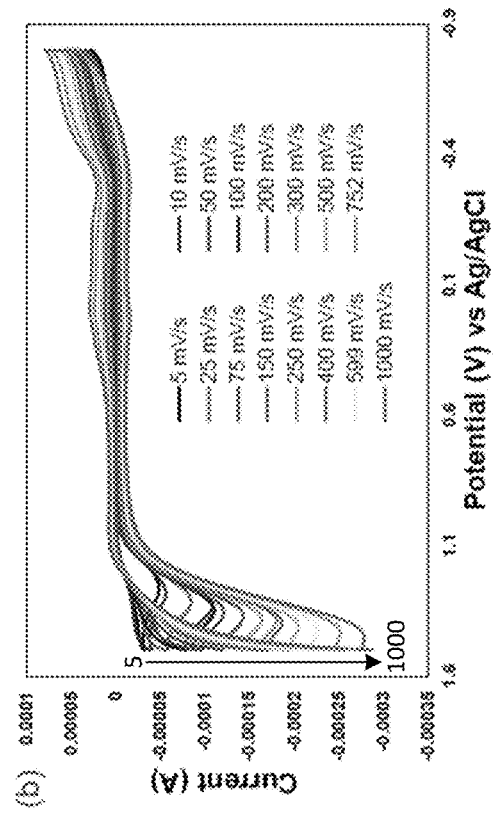
FIGS. 54A-54B show scan rate dependence of cyclic voltammograms of (54A) 7 ng/L PFOA and (54B) 7 mg/L PFOA versus Ag/AgCl in 1 M $KNO_3$. The interrogated scan rates varied from 5 mV/s to 1000 mV/s.
Figure 54B:
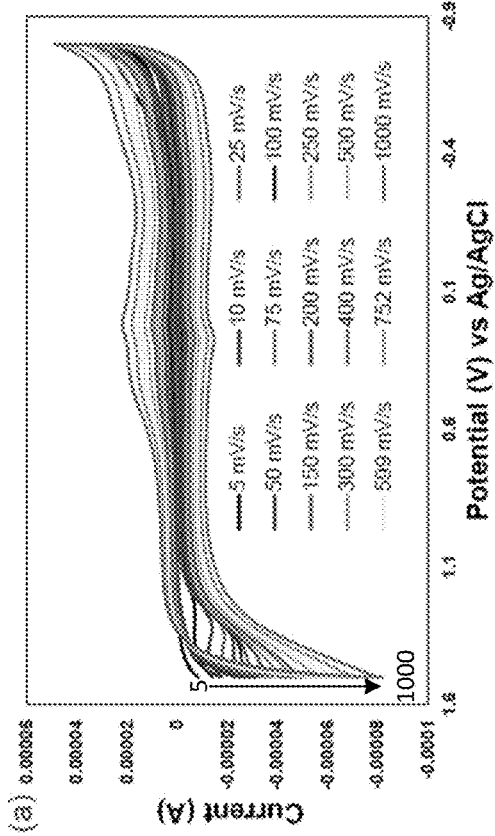
Figure 55:
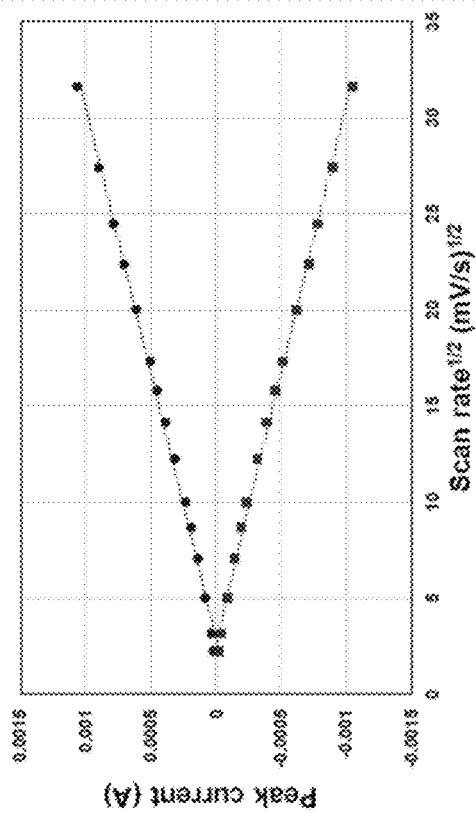
FIG. 55 shows scan rate dependence of cyclic voltammograms of NiFe coated ITO electrode versus Ag/AgCl in 1 M $KNO_3$. The interrogated scan rates varied from 5 mV/s to 1000 mV/s.

Cyclic voltammetry (CV) and differential pulse voltammetry (DPV) studies were conducted with a BASi EC Epsilon potentiostat. Cyclic voltammograms of PFOA were recorded in a solution of 1 M KNO₃, with PFOA concentrations ranging from 7 ng/L to 7 mg/L in presence of exact equivalents of KOH. The cyclic voltammograms were conducted using a standard three-component electrode system with ITO or NiFe modified ITO as the working electrode, an Ag/AgCl (1 M KCl as the reference electrode solution) as the reference electrode and a platinum wire counter electrode over a scan rate range of 5 mV/s to 1000 mV/s, scanning the range of −800 mV to 1500 mV for both the ITO electrode (area 200 mm²) and NiFe electrode (area 100 mm²). The PFOA solutions exhibited no discernible redox signal (FIGS. 54A-54B), confirming the need for a secondary redox-active probe in order to detect it electrochemically. At the slowest scan rate of 5 mV/s at which measurements were conducted, the peak-to-peak separation between the anodic and cathodic peak potential was 13 mV. This is significantly lower than the peak-to-peak separation of 59 mV expected for a process with an electron-transfer stoichiometry of one, namely $Fe(CN)_6^{3-/4-}$. Assuming the unit cell composition of NiFe to comprise two $Fe(CN)_6^{3-/4-}$ units, the peak separation was still lower than anticipated for a 2-electron process, based on the same number of cumulative $Fe(CN)_6^{3-/4-}$ units with no discernible electronic communication between them. This was suggestive of a thin-layer behavior. However, it was observed that as scan rate is increased, the peak-to-peak separation progressively increased, as shown in FIG. 55. This is indicative of diffusion playing a role in the process; this dependence on diffusion is further illustrated by the fact that holding the potential at 0.90 V results in complete stripping of the NiFe from the electrode surface.

Figure 56:
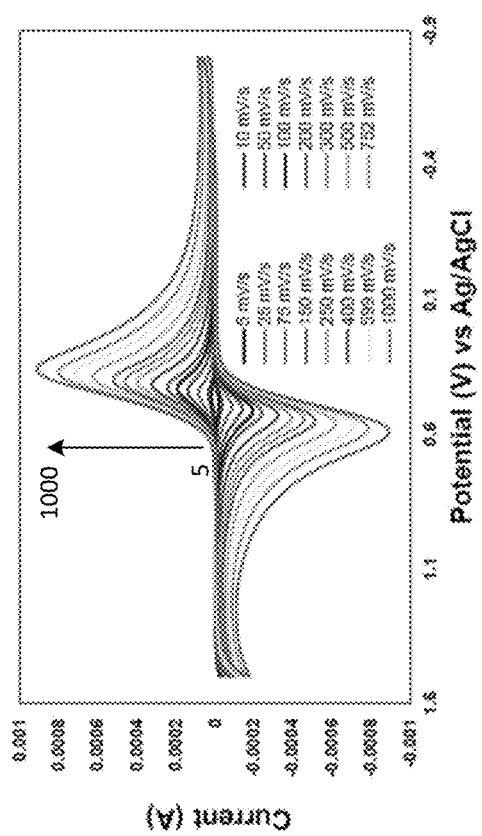
FIG. 56 is a plot of cathodic and anodic peak currents of FIG. 55 as a function of the square root of the scan rates. The line equations are: $i_{pc}=0.036v^{1/2}-0.102$; $R^2=0.996$; and $i_{pa}=-0.0357v^{1/2}=0.098$; $R^2=0.997$.
Figure 57:
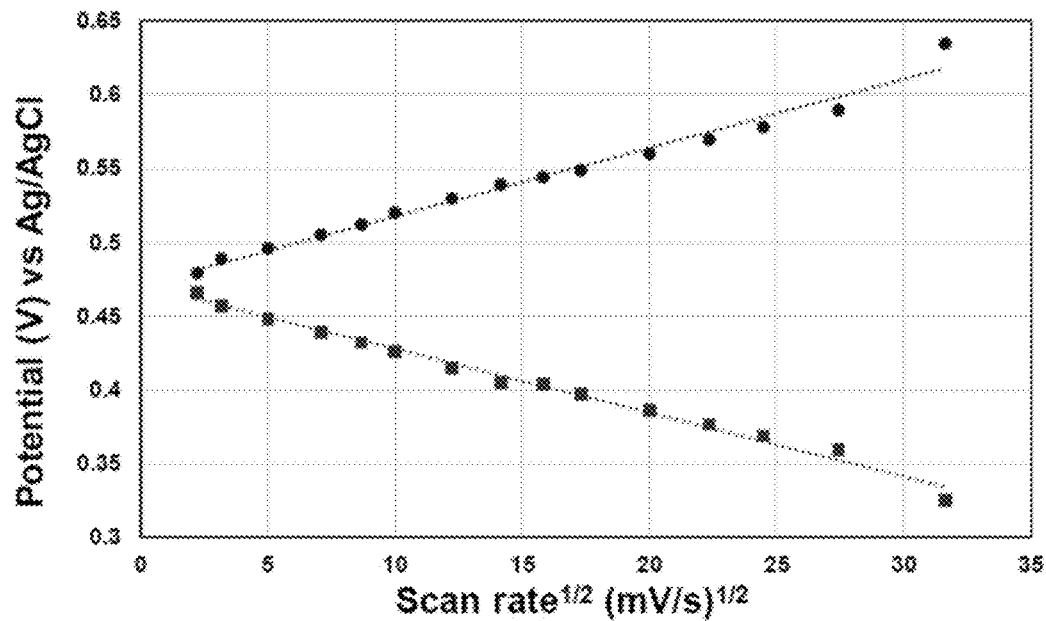
FIG. 57 is a plot of the peak potentials of FIG. 55 versus the square roots of the scan rates.

A Randle-Sevcik analysis was conducted on the peak current which follows the relation:

$$i_p = 0.4663 nFAC\left(\frac{nFvD}{RT}\right)^{\frac{1}{2}}$$

where $i_p$ is the peak current, n is the number of electrons transferred, A is the electrode area, F is Faraday's constant, D is the diffusion coefficient, C is the concentration, v is the scan rate, R is the ideal gas constant, and T is temperature. Based on this equation, a plot of peak currents for the respective anodic and cathodic peak currents against their respective square root of scan rates yielded well-fitting regression lines, as seen in FIG. 56 with $R^2$ values of 0.996 for fits of the cathodic peaks and 0.997 for the anodic peaks respectively, confirming the process is controlled by diffusion. A similar plot of the peak potentials versus the square roots of scan rates as shown in FIG. 57 displayed a similar linearity, further demonstrating the role of diffusion in the process.

Figure 58:
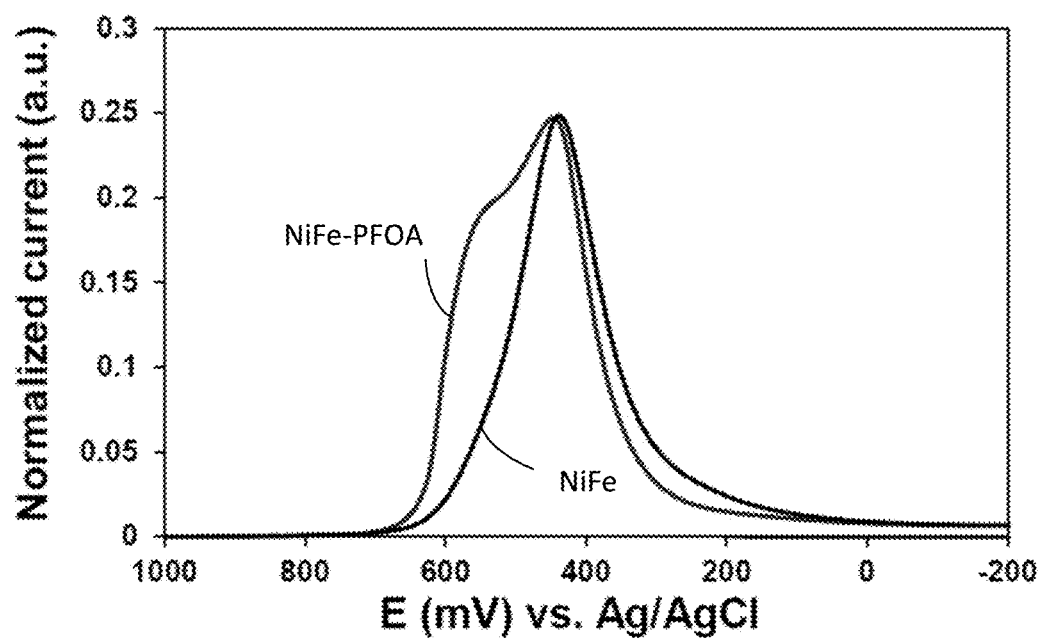
FIG. 58 shows linear sweep voltammograms (sweep rate=50 mV/s) of NiFe coated ITO electrode (vs. Ag/AgCl) in 1 M $KNO_3$ in the absence and presence of 7 mg/L PFOA.

To see if the introduction of PFOA resulted in any discernible changes in the redox behavior of NiFe, pristine ITO electrodes loaded with approximately equivalent quantities of NiFe were exposed to different concentrations of PFOA, and the electrochemical behavior was interrogated through voltammetric studies. Exposure of the NiFe coated electrode to a solution of 7 mg/L of PFOA was observed to show a new redox process in the linear sweep voltammetry profile in addition to the NiFe processes, and at more positive voltages (~0.58 V vs Ag/AgCl at a sweep rate of 50 mV/s as shown in FIG. 58. Considering that PFOA by itself did not show any such processes when being interrogated electrochemically with an ITO electrode, this suggested that this process may be due to the interaction (i.e. sorption) of PFOA with NiFe.

However, since this concentration of PFOA is impractical and enormously larger than that anticipated in practical drinking or groundwater matrices, the electrochemical behavior was interrogated at environment relevant concentrations. Impressively, introduction of PFOA at concentrations as low as 10 ng/L to the system was observed to still result in a discernible change in the redox behavior. The linear sweep voltammetry shown in FIG. 55A illustrates the redox behavior of NiFe in presence of PFOA, showing the generation of a new redox process at more positive voltages (~0.58 V vs Ag/AgCl at a sweep rate of 50 mV/s). This direct observation of a PFOA signal at 10 ng/L that was clearly distinguishable from the NiFe signal, indicated a limit of quantification of 10 ng/L for this system, which is far below the EPA HAL of 70 ng/L.

Increasing the PFOA concentrations from 10 ng/L to 700 ng/L was observed to enhance this second process as reflected in the progressive increase of the peak current of the similar process observed at a similar scan rate; a simultaneous shift of the $Fe(CN)_6^{3-/4-}$ redox process to more positive voltages was also observed, as shown in FIG. 59A, indicating the dependence of the two processes on each other. It is to be noted that while attempts were made to maintain the thickness and quantity of NiFe on the electrode surface similar, there were slight variations, and therefore, the peak currents were normalized with respect to the $Fe(CN)_6^{3-/4-}$ cathodic peak current for comparison purposes. As the sweep rates were increased, the distinction between the processes became smaller till they merged into a single broad process. To determine whether there was a correlation between the peak current of the second process with the PFOA concentration, a working calibration curve was constructed, as shown in FIG. 59B. It was desired to focus in the PFOA concentration range of 0-700 ng/L, as this is the general PFOA concentration range observed in clean or expectedly contaminated ground or drinking water streams. A plot of the net magnitude of peak current intensities in presence PFOA (calculated as the difference between the intensity in presence of PFOA and in the absence of it) against the logarithm of PFOA concentration in solution, showed a linear correlation. This allowed calculation of the limit of detection. The limit of detection (LOD) was calculated from the plot based on the IUPAC recommended equation reported by Long et al. (*Anal Chem* 1983, 55(7):A712).

$$Dl = \frac{k \square S_b}{m}$$

where DL is the detection limit, k is a numerical constant, m is the slope of the linear region of the plot, and Sb is the standard error for the blank measurements, respectively. In accordance with IUPAC recommendations, a k value of 3 was applied, which corresponds to a 99.87% confidence level. Based on this, a detection limit of 1.6 ng/L is obtained which is sufficiently lower than the health advisory limit of 70 ng/L set by US-EPA.

Differential pulse voltammetry measurements were also performed using the NiFe coated ITO electrodes due to their greater sensitivity at lower concentrations, where the behavior of the electrode was studied both in the absence of PFOA as well as in presence of 0-700 ng/L PFOA. In the absence of PFOA, the electrodes showed a single redox process at 0.45 V, as shown in FIG. 60A. Exposure to PFOA showed a second process at a higher potential (~0.55 V vs Ag/AgCl), which was initially observed as a shoulder at lower concentrations, but subsequently gained prominence. A plot of the net magnitude of peak current intensities of this second process observed in presence of PFOA (calculated as the difference between the intensity in presence of PFOA and in the absence of it) against the logarithm of PFOA concentration in solution, showed a linear correlation (FIG. 60B). Using the above equation, a detection limit of 1.3 ng/L was obtained which is comparable to that obtained under linear sweep voltammetry conditions.

In conclusion, batch contact experiments with bulk quantities of powder sorbent NiFe material confirmed capture of PFOA via 1) presence of characteristic IR susceptible vibration frequencies corresponding to the fluorocarbon structure, 2) elemental mapping via high resolution microscopy, 3) alterations in binding energies of key framework metal nodes and corresponding fluorine species of PFOA as well as 4) a reduction in apparent available surface area all while maintaining structural integrity. Importantly, linear sweep and differential pulse voltammetry experiments were used to probe extremely low concentration solutions of PFOA after growth of the porous material on an electrode surface. These electrochemistry experiments revealed significant and discernable peak current intensities at more positive voltages which are attributed to the redox process as a result of electrostatic interactions during sorption. This speculation was further supported by increasing peak current intensities of this redox peak as a function of bulk phase PFOA concentration observed at a voltage of ~0.7V. Overall, the incorporation of a redox active NiFe sorbent material on an electrode surface was shown to be sensitive for both the capture and subsequent detection of low concentrations of PFOA with detection limits calculated to be as low as ~1.3 ng/L.

Example 7

PFAS Capture and Photocatalytic Degradation

Figure 61:
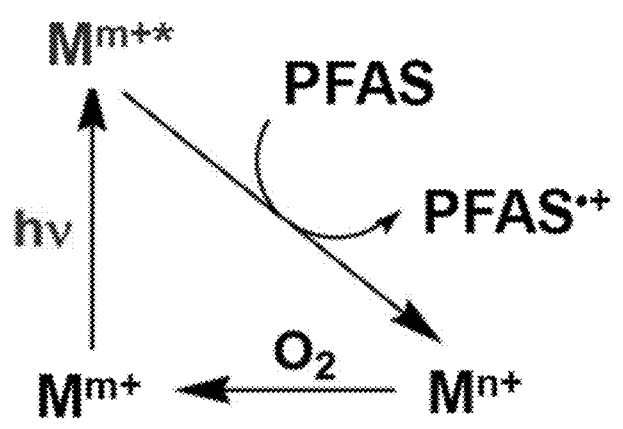
FIG. 61 is a schematic diagram showing interconversion between nonreactive, photoactive, and excited states of a photocatalyst with oxidative destruction of a PFAS.

A PFAS-containing sample is combined with a composite sorbent comprising a MOF and a photocatalyst, whereby the PFAS binds to the MOF to form a PFAS-sorbent complex. The PFAS-sorbent complex is exposed to a wavelength effective to excite the photocatalyst, thereby oxidatively destroying the PFAS as the photocatalyst returns to its ground state (FIG. 61).

Figure 62:
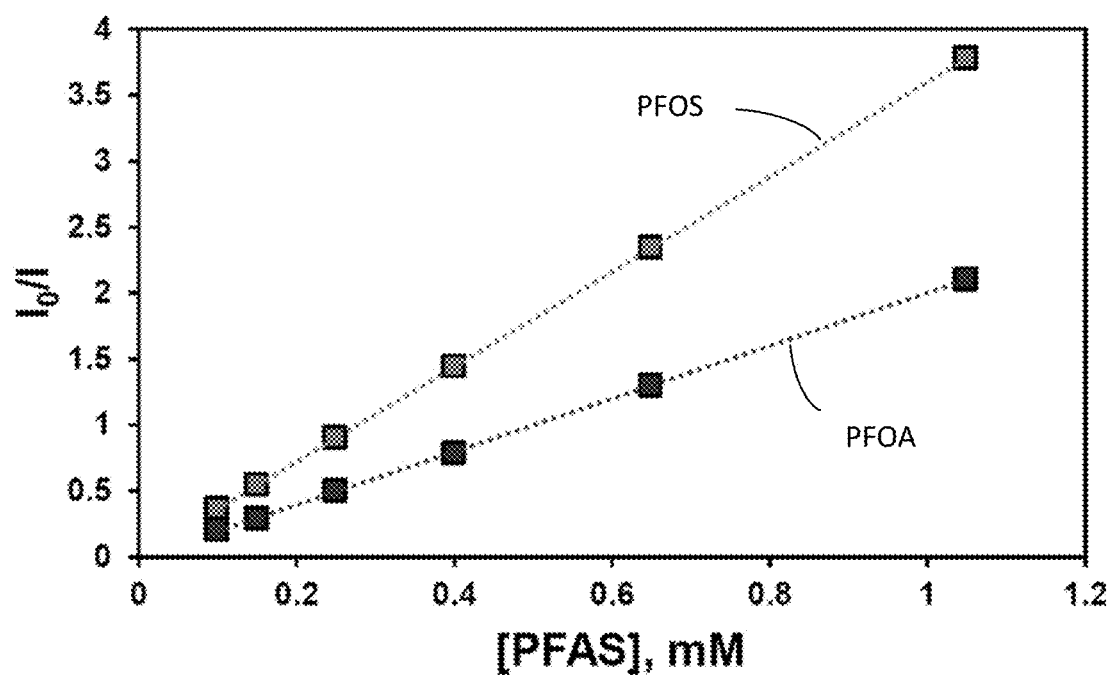
FIG. 62 is a graph showing Stern-Volmer quenching of rhenium (II) dimethylphosphinoethane emission intensity due to degradation of PFOA and PFOS.

Rhenium (II) dimethylphosphinoethane was demonstrated to catalyze PFOS and PFOA photodegradation. The experiment consisted of the following steps. A given amount of rhenium (II) dimethylphosphinoethane hexafluorophosphate salt was taken in water, and it was degassed by blowing argon for 30 minutes. Its emission intensity was recorded at an excitation at 532 nm, given by I0. To the same solution an aqueous solution of PFAS (PFOS or PFOA) was added; the solution was degassed by blowing argon for 30 minutes, and the emission of the resultant solution was recorded. This process was repeated multiple times, and it was observed that with incremental PFAS concentration, the emission intensity was reduced, due to the rhenium (II) dimethylphosphinoethane complex reacting with the PFAS, inducing its photocatalytic degradation, and itself getting reduced to rhenium (I) dimethylphosphinoethane. FIG. 62 shows Stern-Volmer quenching of rhenium (II) dimethylphosphinoethane emission intensity due to degradation of PFOA and PFOS.

Example 8

Pore Surface Engineering

Pore surface engineering was performed during synthesis of a MOF or by post-synthetic modifications.

UiO-66 pores were functionalized during MOF synthesis. Briefly, a mixture of 3:1 benzene dicarboxylic acid (BDC) and OH/COOH/SO$_3$H/NH$_2$ functionalized BDC was dissolved in N,N-dimethylformamide (DMF) containing hydrochloric acid. To this solution, ZrCl$_4$ was added and sonicated for 15 minutes to obtain a homogenous reaction mixture. The mixture was then heated at 80° C. for 18 hours after which a white precipitate powder was obtained, such as UIO-66-SO$_3$H or UIO-66-NH$_2$. The as-synthesized material was washed using fresh DMF and methanol for several days to remove unreacted reagents and exchanged the solvent from the pore volume.

In another examples, UiO-66 was modified post-synthesis. Briefly, activated UiO-66 was suspended in dichloromethane and stirred at 0° C. To this solution, a known amount of functional group was added dropwise and allowed to equilibrate for 1 h, after which the product was filtered, rinsed with fresh dichloromethane, and reactivated under vacuum at 150° C. overnight. For example, to functionalize with SO$_3$H, chlorosulfonic acid was added to the UiO-66 to obtain UiO-66-SO$_3$H.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method, comprising:
capturing a per- or polyfluoroalkyl substance (PFAS) from a sample by
combining the sample with a composite sorbent, thereby sorbing the PFAS to the composite sorbent to form a PFAS-sorbent, the composite sorbent comprising at least two different materials, (a) and (b), wherein (a) is a metal-organic framework (MOF), a covalent organic framework (COF), a covalent organic polymer (COP), a zeolite, mesoporous silica, or hierarchical porous carbon, and (b) is at least one of a polymer, a zeolite, a covalent organic framework, mesoporous silica, a hierarchical porous carbon, a photocatalyst, a carbon nanotube, graphite, graphene, graphene oxide, a Prussian blue analog, or a metal oxide, wherein
(i) the MOF, if present, does not comprise [Zr$_6$O$_4$(OH)$_4$] and 1,4-benzodicarboxylic acid (UiO-66), and/or
(ii) the polymer, if present, is not poly(ethylene-co-vinyl acetate).

2. The method of claim 1, wherein combining the sample with the composite sorbent comprises flowing the sample through a bed of a column, the bed comprising the composite sorbent.

3. The method of claim 2, wherein the composite sorbent comprises particulates having a size of from 100 μm to 500 μm.

4. The method of claim 2, wherein a flow rate through the bed is from 0.5 bed volumes/minute to 10 bed volumes/minute.

5. The method of claim 1, wherein the sample has a contact time with the composite sorbent of from 1 minute to 24 hours.

6. The method of claim 1, further comprising heating the PFAS-sorbent to a temperature $T_1$ sufficient to thermally degrade the PFAS.

7. The method of claim 6, wherein the PFAS-sorbent is heated to the temperature $T_1$ for a time period of from 1 hour to 24 hours.

8. The method of claim 6, wherein the temperature $T_1$ is less than a temperature $T_2$ sufficient to thermally degrade the PFAS when not sorbed to the composite sorbent.

9. The method of claim 6, wherein the temperature $T_1$ sufficient to thermally degrade the PFAS is from 50° C. to 200° C.

10. The method of claim 6, further comprising heating the PFAS-sorbent in a solution comprising H$_2$SO$_4$, NaHSO$_5$, Na$_2$S$_2$O$_8$, FeSO$_4$, H$_2$O$_2$, Na$_2$S$_2$O$_4$, NaClO$_3$, NaClO$_4$, Na$_2$S$_2$O$_5$, HCl, KI, NaNO$_3$, HNO$_3$, Fe(0), Zn, Ni, Na$_2$SO$_3$, NaClO, Ca(OH)$_2$, K$_2$CrO$_4$, Na$_2$S$_2$O$_3$, Na$_2$CO$_3$, KMNO$_4$, K$_2$FeO$_4$, NaBH$_4$, NaOH, KOH, or any combination thereof.

11. The method of claim 1, wherein the MOF comprises M$_3$X(H$_2$O)$_2$O(BDC)$_3$·nH$_2$O where M is Cr or Fe, X is OH or F, BDC is 1,4-benzenedicarboxylate, and n is about 25.

12. The method of claim 1, wherein the sample comprises groundwater, and the MOF comprises Fe$_3$X(H$_2$O)$_2$O(BDC)$_3$·nH$_2$O where X is OH or F, BDC is 1,4-benzenedicarboxylate, and n is about 25.

13. The method of claim 1, wherein the composite sorbent comprises a MOF and the MOF is redox-active.

14. The method of claim 1, wherein the composite sorbent comprises a photocatalyst and the method further comprises exposing the PFAS-sorbent to light having a wavelength effective to excite the photocatalyst, thereby degrading the PFAS.

15. The method of claim 14, wherein the photocatalyst comprises rhenium (II) dimethylphosphinoethane or a salt thereof.

16. The method of claim 14, where the photocatalyst comprises a polyoxometalate.

17. The method of claim 16, where the polyoxometalate comprises α-HP$_3$M$_{12}$O$_{40}$·6 H$_2$O, where M is W, Mo, V, Nb, Ta, or any combination thereof.

18. The method of claim 1, wherein the PFAS comprises a PFAS of Table 1 or any combination thereof.

19. The method of claim 1, wherein the composite sorbent is attached to a support.

20. The method of claim 19, wherein the support is a carbon nanotube, a carbon fiber, a polymer particulate, granular carbon, or a zeolite.

\* \* \* \* \*